US010308620B2

(12) United States Patent
Nirogi et al.

(10) Patent No.: US 10,308,620 B2
(45) Date of Patent: Jun. 4, 2019

(54) MUSCARINIC M1 RECEPTOR POSITIVE ALLOSTERIC MODULATORS

(71) Applicant: SUVEN LIFE SCIENCES LIMITED, Banjara Hills, Hyderabad (IN)

(72) Inventors: Ramakrishna Nirogi, Hyderabad (IN); Abdul Rasheed Mohammed, Hyderabad (IN); Anil Karbhari Shinde, Hyderabad (IN); Shankar Reddy Gagginapally, Hyderabad (IN); Venkateswarlu Jasti, Hyderabad (IN)

(73) Assignee: SUVEN LIFE SCIENCES LIMITED, Banjara Hills, Hyderabad (IN)

( * ) Notice: Subject to any disclaimer, the term of this patent is extended or adjusted under 35 U.S.C. 154(b) by 0 days.

(21) Appl. No.: 15/580,632

(22) PCT Filed: Jun. 8, 2016

(86) PCT No.: PCT/IB2016/000771
§ 371 (c)(1),
(2) Date: Dec. 7, 2017

(87) PCT Pub. No.: WO2016/198937
PCT Pub. Date: Dec. 15, 2016

(65) Prior Publication Data
US 2018/0155302 A1    Jun. 7, 2018

(30) Foreign Application Priority Data

Jun. 8, 2015  (IN) .......................... 2851/CHE/2015

(51) Int. Cl.
*C07D 265/36* (2006.01)
*C07D 413/14* (2006.01)
*C07D 413/06* (2006.01)
*C07D 417/06* (2006.01)
*C07D 279/16* (2006.01)
*A61P 25/28* (2006.01)
*A61P 25/18* (2006.01)
*C07D 413/12* (2006.01)
*C07D 498/04* (2006.01)

(52) U.S. Cl.
CPC ............ *C07D 265/36* (2013.01); *A61P 25/18* (2018.01); *A61P 25/28* (2018.01); *C07D 279/16* (2013.01); *C07D 413/06* (2013.01); *C07D 413/12* (2013.01); *C07D 413/14* (2013.01); *C07D 417/06* (2013.01); *C07D 498/04* (2013.01)

(58) Field of Classification Search
CPC .................................................... C07D 265/36
USPC ...................................................... 544/105
See application file for complete search history.

(56) References Cited

FOREIGN PATENT DOCUMENTS

| WO | 2007067489 A1 | 6/2007 |
| WO | 2011149801 A1 | 12/2011 |
| WO | 2015028483 A1 | 3/2015 |
| WO | 2015049574 A1 | 4/2015 |
| WO | 2015080904 A1 | 6/2015 |

OTHER PUBLICATIONS

International Preliminary Report on Patentability for PCT/IB2016/000771.
Wess J. "Molecular biology of muscarinic acetylcholine receptors," Critical Reviews in Neurobiology, 1996, 10:69-99.
Langmead CJ et al. "Muscarinic acetylcholine receptors as CNS drug targets," Pharmacology & Therapeutics, 2008,117:232-243.
Levey AI "Immunological localization of m1-m5 muscarinic acetylcholine receptors in peripheral tissues and brain," Life Sciences, 1993, 52:441-448.
Levey AI "Chronically mad as a hatter: anticholinergics and Alzheimer's disease pathology," Annals of Neurology, 2003, 54:144-146.
Veroff AE et al. "Efficacy of xanomeline in Alzheimer disease: cognitive improvement measured using the Computerized Neuropsychological Test Battery (CNTB)," Alzheimer Disease and Associated Disorders, 1998, 12 (4):304-12.
Uslaner JM et al. "The muscarinic M1 receptor positive allosteric modulator PQCA improves cognitive measures in rat, cynomolgus macaque, and rhesus macaque," Psychopharmacology, 2013, 225(1), 21-30.
Shirey JK et al. "A selective allosteric potentiator of the M1 muscarinic acetylcholine receptor increases activity of medial prefrontal cortical neurons and restores impairments in reversal learning," The Journal of Neuroscience, 2009, 29:14271-14286.
Fisher A "Cholinergic treatments with emphasis on m1 muscarinic agonists as potential disease-modifying agents for Alzheimer's disease," Neurotherapeutics, 2008, 5:433-442.
Caccamo A et al. "M1 agonists as a potential disease-modifying therapy for Alzheimer's disease," Current Alzheimer Research, 2009, 6:112-117.

(Continued)

*Primary Examiner* — Kahsay Habte
(74) *Attorney, Agent, or Firm* — K&L Gates LLP; Louis C. Cullman; Michelle Glasky Bergman

(57) ABSTRACT

The present invention relates to compound of formula (I), or stereoisomers and pharmaceutically acceptable salts as muscarinic M1 receptor positive allosteric modulators. This invention also relates to methods of preparing such compounds and pharmaceutical compositions comprising such compounds. The compounds of this invention are useful in the treatment of various disorders that are related to muscarinic M1 receptor.

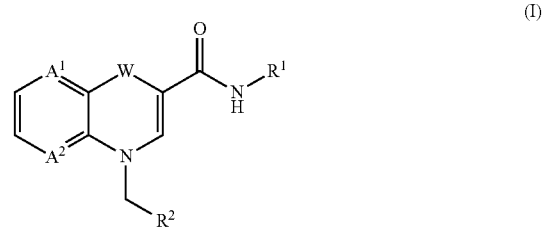

(I)

16 Claims, 4 Drawing Sheets

(56) References Cited

OTHER PUBLICATIONS

Lanz TA et al. "The gamma-secretase inhibitor N-[N-(3,5-difluorophenacetyl)-L-alanyl]-S-phenylglycine t-butyl ester reduces A beta levels in vivo in plasma and cerebrospinal fluid in young (plaque-free) and aged (plaque-bearing) Tg2576 mice," Journal of Pharmacology and Experimental Therapeutics, 2003, 305:864-871.

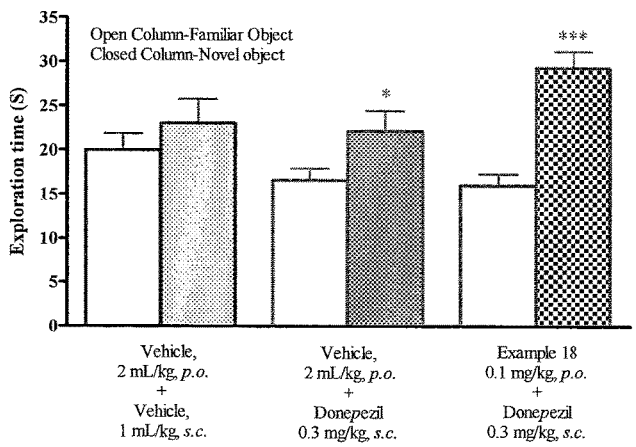
*p<0.05, ***p<0.001 vs familiar object
Figure 1: Effect of example 18 with donepezil in time induced memory deficit
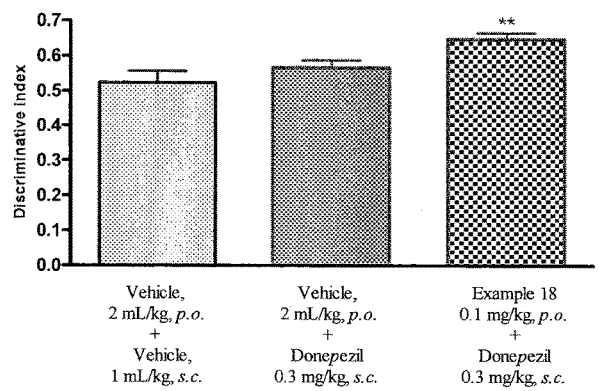
**p<0.01 vs vehicle
Figure 2: The discriminative index showing effect of example 18 with donepezil in time induced memory deficit

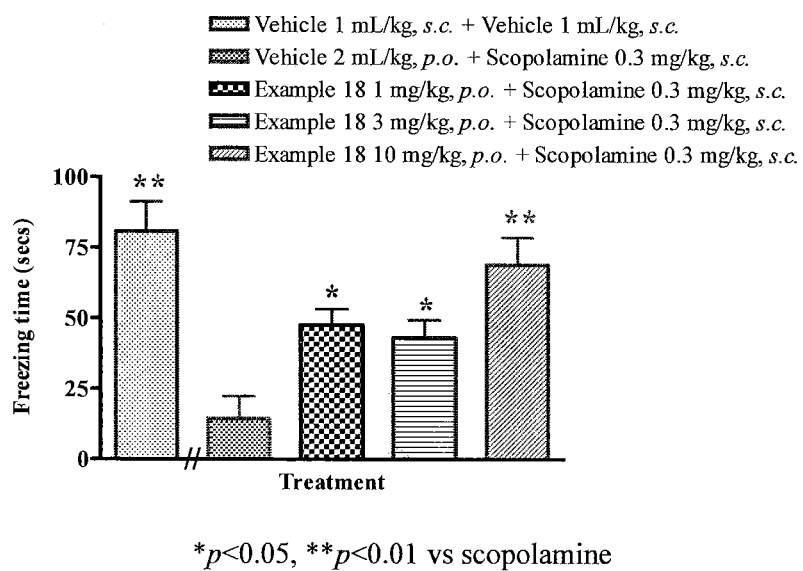
Figure 3: Example 18 reversed the scopolamine induced memory deficit

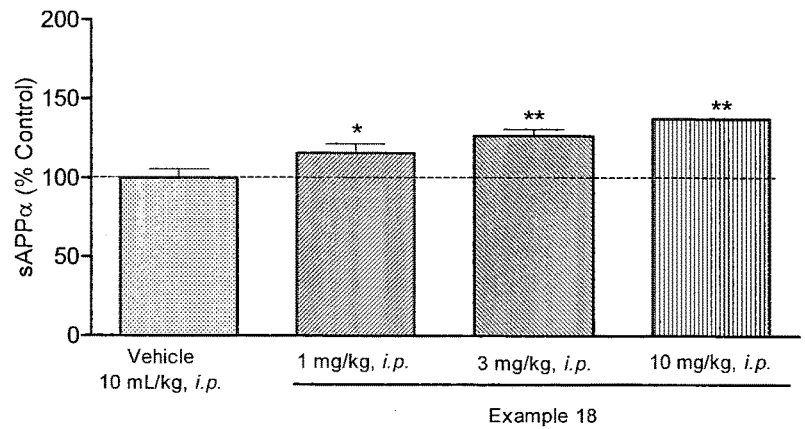
Values are mean ± SEM (n=8/ group). *$p<0.05$, **$p<0.01$ Vs Vehicle (Dunnett's post test).
Figure 4: Effect of the example 18 on cortical sAPPα levels in male C57BL/6J mice.
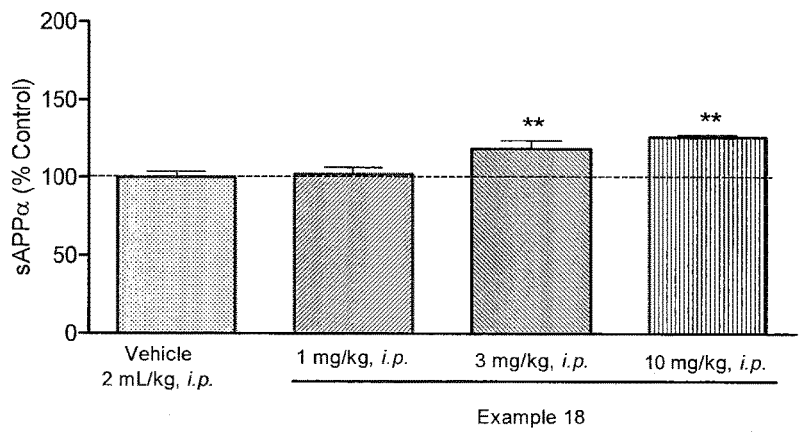
Values are mean ± SEM (n=8/ group). **$p<0.01$ Vs Vehicle (Dunnett's post test).
Figure 5: Effect of the example 18 on cortical sAPPα levels in male Wistar rats.

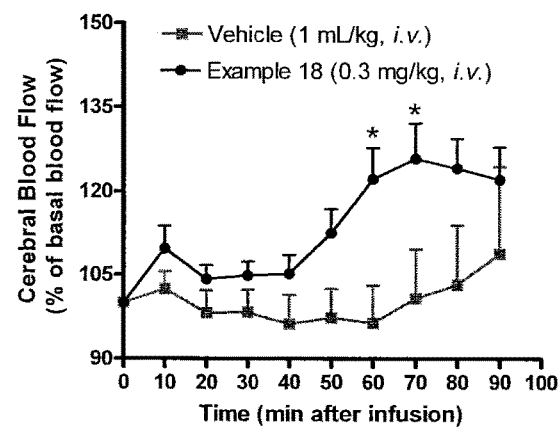
*p<0.05 vs. vehicle, Two-way ANOVA followed by Bonferroni post test, n = 6 - 9
Figure 6: Effect of example 18 on cerebral blood flow in the frontal cortex

MUSCARINIC M1 RECEPTOR POSITIVE ALLOSTERIC MODULATORS

FIELD OF THE INVENTION

The present invention relates to compounds of formula (I), or their isotopic forms, stereoisomers, or pharmaceutically acceptable salts as muscarinic M1 receptor positive allosteric modulators (M1 PAMs). The present invention also describes method of making such compounds, pharmaceutical compositions comprising such compounds and their use.

BACKGROUND OF THE INVENTION

Muscarinic acetylcholine receptors (mAChRs), which belong to the class A family of G protein-coupled receptors (GPCRs). They are widely expressed throughout the body. Five subtypes termed M1 through M5 that respond to the endogenous neurotransmitter acetylcholine (ACh) have been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The M1 muscarinic receptor is predominantly expressed in the brain regions such as cortex, hippocampus and amygdala which involved in cognition, and therefore selective activation of the M1 receptor would be expected to boost cognitive performance (*Annals of Neurology*, 2003, 54, 144-146).

Xanomeline, a muscarinic acetylcholine receptor agonist with reasonable selectivity for the M1 and M4 subtypes, produced significant effects on cognition in a clinical Alzheimer's disease (AD) trial (*Alzheimer Disease and Associated Disorders*, 1998, 12(4), 304-12) although gastrointestinal side effects led to a high dropout rate in clinical trials. There is a high degree of conservation between muscarinic receptor subtypes at their orthosteric acetylcholine ligand binding sites which makes it difficult to identify a M1 selective agonist.

To circumvent this issue of selectivity and safety, an alternative approach consists of developing M1 PAMs that act at the less conserved allosteric binding site. Merck reported the development of M1 positive allosteric modulator, PQCA (1-{[4-cyano-4-(pyridine-2-yl)piperidin-1-yl]methyl}-4-oxo-4H-quinolizine-3-carboxylic acid). This compound is highly selective for M1 over the other muscarinic receptor sub types and found to be efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies it was demonstrated that M1 activation increases neurotransmitter acetylcholine concentration in brain. Moreover, the M1 activation has potential as disease-modifying therapy for AD by both shifting the APP processing towards the non-amyloidogenic α-secretase pathway and by decreasing the tau hyper-phosphorylation. Positive allosteric modulators at M1 receptor have demonstrated to increase the generation of sAPPα in-vitro (*The Journal of Neuroscience*, 2009, 29, 14271-14286). Therefore, M1 PAMs provide an approach to target both symptomatic and disease-modifying treatment of cognitive deficits in AD and schizophrenia.

PCT patent application publications, WO2015049574, WO2015028483, WO2007067489 and WO2011149801 have disclosed some M1 PAM compounds. While several M1 PAMs have been disclosed in the literature till date, no drug acting as M1 PAM is launched in the market. Therefore, there is an un-met need and scope to discover and develop new M1 PAMs with novel chemical structures devoid of any side effects for the treatment of disorders, which are regulated by M1 receptors.

SUMMARY OF THE INVENTION

In first aspect, the present invention relates to M1 PAMs of compound of formula (I),

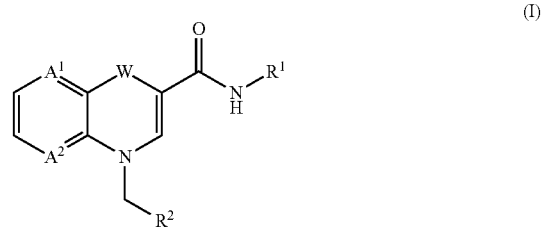

(I)

wherein:
$A^1$ and $A^2$ are each independently represents CH, CF or N;
W is O, S, S(O) or S(O)$_2$;
$R^1$ is

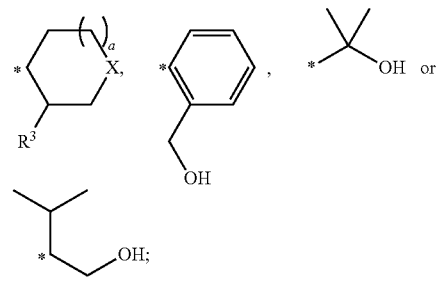

$R^2$ is

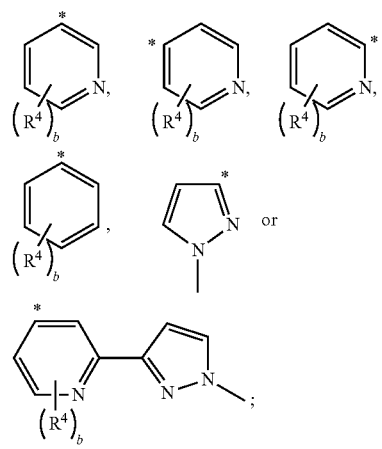

wherein: * represents point of attachment;
R³ is OH, F, NH₂ or H;
R⁴ at each occurrence is independently selected from halogen, —O—CH₃; —S—CH₃, —N(CH₃)₂, —CH₃, —CF₃, —CHF₂, —CH₂F, —OH, —CN, phenyl, pyridyl and hydrogen; wherein phenyl and pyridyl are optionally substituted with one or more substituents selected from the group consisting of halogen or CH₃;
X is CH₂, O or NH;
a is 0 or 1; and b is 1 or 2;
or an isotopic form, a stereoisomer, a tautomer or a pharmaceutically acceptable salt thereof.

In another aspect, the present invention relates to the processes for preparing the compound of formula (I), or a stereoisomer and a pharmaceutically acceptable salt thereof.

In yet another aspect, the present invention relates to pharmaceutical composition containing a therapeutically effective amount of at least one compound of formula (I), or a stereoisomer and a pharmaceutically acceptable salt thereof and pharmaceutically acceptable excipients or carriers.

In yet another aspect, the present invention relates to compound of formula (I), or a stereoisomer and a pharmaceutically acceptable salt thereof, for use as M1 PAM.

In yet another aspect, the present invention relates to compound of formula (I), or a stereoisomer and a pharmaceutically acceptable salt thereof, for use in the treatment of various disorders selected from AD, schizophrenia, cognitive disorders, pain or sleep disorders.

In another aspect, the present invention relates to a method for the treatment of disorders related to muscarinic M1 receptor, comprising administering to a patient in need thereof, a therapeutically effective amount of a compound of formula (I), or a stereoisomer and a pharmaceutically acceptable salt thereof.

In yet another aspect, the present invention relates to use of the compound of formula (I), or a stereoisomers and pharmaceutically acceptable salts thereof, for the manufacture of a medicament for the treatment of disorders related to muscarinic M1 receptor.

BRIEF DESCRIPTION OF THE DRAWINGS

FIG. 1: Effect of example 18 with donepezil in time induced memory deficit
FIG. 2: The discriminative index showing effect of example 18 with donepezil in time induced memory deficit
FIG. 3: Effect of example 18 on the scopolamine induced memory deficit
FIG. 4: Effect of example 18 on cortical sAPPα levels in male C57BL/6J mice
FIG. 5: Effect of example 18 on cortical sAPPα levels in male Wistar rats
FIG. 6: Effect of example 18 on cerebral blood flow in the frontal cortex

DETAILED DESCRIPTION OF THE INVENTION

Unless otherwise stated, the following terms used in the specification and claims have the meanings given below:
The term "halogen" means fluorine, chlorine, bromine or iodine.
The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include ²H (deuterium) and ³H (tritium).

The term, "stereoisomers" as used herein refers to isomers of compound of formula (I) that differ in the arrangement of their atoms in space. Compounds disclosed herein may exist as single stereoisomers, racemates and/or mixtures of enantiomers and/or diastereomers. All such single stereoisomers, racemates and mixtures thereof are intended to be within the scope of the present invention.

The term, "pharmaceutically acceptable salt" as used herein refers to salts of the active compound i.e. the compound of formula I, and are prepared by reaction with the appropriate acid or acid derivative, depending on the particular substituents found on the compounds described herein.

Embodiments

The present invention encompasses all the compounds described by the compound of formula (I) without limitation, however, preferred aspects and elements of the invention are discussed herein in the form of the following embodiments.

In one embodiment, the present invention relates to the compound of formula (I), wherein: W is O; or an isotopic form, a stereoisomer or a pharmaceutically acceptable salt thereof.

In another embodiment, the present invention relates to the compound of formula (I), wherein: W is S or S(O); or an isotopic form, a stereoisomer or a pharmaceutically acceptable salt thereof.

In another embodiment, the present invention relates to the compound of formula (I), wherein: A¹ is CH or CF; or an isotopic form, a stereoisomer or a pharmaceutically acceptable salt thereof.

In another embodiment, the present invention relates to the compound of formula (I), wherein: A¹ is N; or an isotopic form, a stereoisomer or a pharmaceutically acceptable salt thereof.

In another embodiment, the present invention relates to the compound of formula (I), wherein: A² is CH or CF; or an isotopic form, a stereoisomer or a pharmaceutically acceptable salt thereof.

In another embodiment, the present invention relates to the compound of formula (I), wherein: A² is N; or an isotopic form, a stereoisomer or a pharmaceutically acceptable salt thereof.

In yet another embodiment, the present invention relates to the compound of formula (I), wherein: W is O; A¹ is CH or CF; or an isotopic form, a stereoisomer or a pharmaceutically acceptable salt thereof.

In yet another embodiment, the present invention relates to the compound of formula (I), wherein: W is O; A² is CH or CF; or an isotopic form, a stereoisomer or a pharmaceutically acceptable salt thereof.

In another embodiment, the present invention relates to the compound of formula (I), wherein:
$R^1$ is

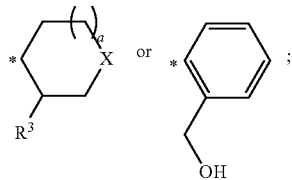

wherein * represents point of attachment; X, $R^3$ and a are as defined in first aspect; or an isotopic form, a stereoisomer or a pharmaceutically acceptable salt thereof.

In another embodiment, the present invention relates to the compound of formula (I), wherein:
$R^1$ is

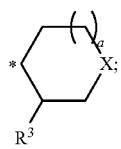

wherein * represents point of attachment; X, $R^3$ and a are as defined in first aspect; or an isotopic form, a stereoisomer or a pharmaceutically acceptable salt thereof.

In another embodiment, the present invention relates to the compound of formula (I), wherein:
$R^1$ is

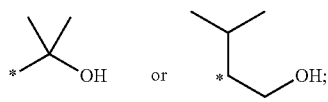

wherein * represents point of attachment; or an isotopic form, a stereoisomer or a pharmaceutically acceptable salt thereof.

In another embodiment, the present invention relates to the compound of formula (I), wherein:
$R^2$ is

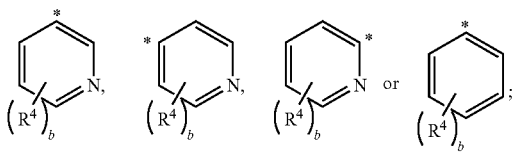

wherein * represents point of attachment; $R^4$ and b are as defined in the first aspect or an isotopic form, a stereoisomer or a pharmaceutically acceptable salt thereof.

In another embodiment, the present invention relates to the compound of formula (I), wherein:
$R^2$ is

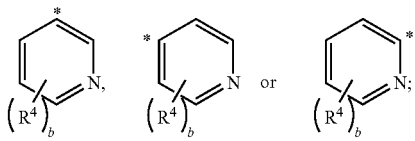

wherein * represents point of attachment; $R^4$ and b are as defined in the first aspect or an isotopic form, a stereoisomer or a pharmaceutically acceptable salt thereof.

In another embodiment, the present invention relates to the compound of formula (I), wherein:
$R^2$ is

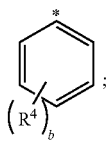

wherein * represents point of attachment; $R^4$ and b are as defined in the first aspect or an isotopic form, a stereoisomer or a pharmaceutically acceptable salt thereof.

In another embodiment, the present invention relates to the compound of formula (I), wherein:
$R^1$ is

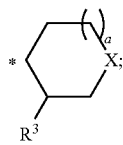

$R^2$ is

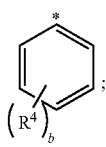

wherein * represents point of attachment; X is $CH_2$; $R^3$, $R^4$, a and b are as defined in the first aspect; or an isotopic form, a stereoisomer or a pharmaceutically acceptable salt thereof.

In another embodiment, the present invention relates to the compound of formula (I), wherein:
$R^1$ is

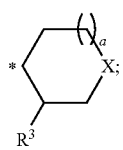

$R^2$ is

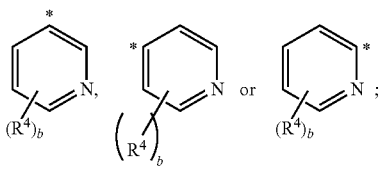

wherein * represents point of attachment; X is $CH_2$; $R^3$, $R^4$, a and b are as defined in the first aspect, or an isotopic form, a stereoisomer or a pharmaceutically acceptable salt thereof.

In another embodiment, the present invention relates to the compound of formula (I), wherein:
$R^1$ is

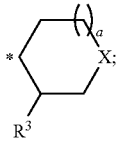

$R^2$ is

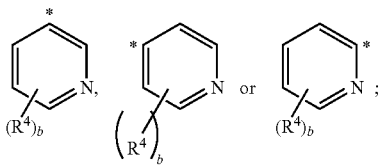

wherein * represents point of attachment; X is NH; $R^3$, $R^4$, a and b are as defined in the first aspect, or an isotopic form, a stereoisomer or a pharmaceutically acceptable salt thereof.

In another embodiment, the present invention relates to the compound of formula (I), wherein:
W is O;
$A^1$ and $A^2$ are CH;
$R^1$ is

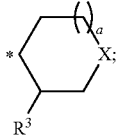

$R^2$ is

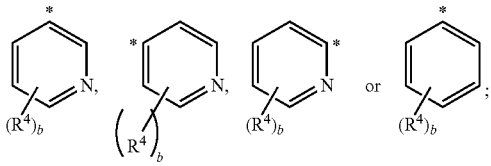

wherein * represents point of attachment; $R^3$, $R^4$, X, a and b are as defined in the first aspect; or an isotopic form, a stereoisomer or a pharmaceutically acceptable salt thereof.

In another embodiment, the present invention relates to the compound of formula (I), wherein:
W is S;
$A^1$ and $A^2$ are CH;
$R^1$ is

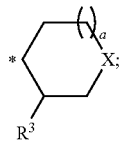

$R^2$ is

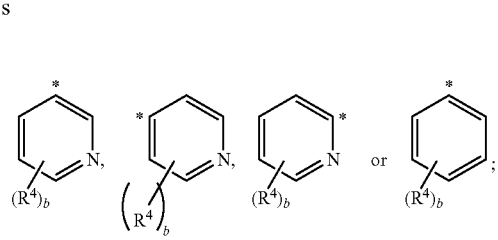

wherein * represents point of attachment; $R^3$, $R^4$, X, a and b are as defined in the first aspect; or an isotopic form, a stereoisomer or a pharmaceutically acceptable salt thereof.

In another embodiment, the present invention relates to the compound of formula (I), wherein:
W is O;
$A^1$ and $A^2$ are CH;
$R^1$ is

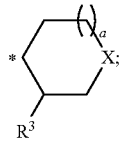

$R^2$ is

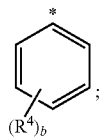

wherein * represents point of attachment; X is $CH_2$; $R^3$, $R^4$, a and b are as defined in the first aspect; or an isotopic form, a stereoisomer or a pharmaceutically acceptable salt thereof.

In another embodiment, the present invention relates to the compound of formula (I), wherein:
W is S;
$A^1$ and $A^2$ are CH;
$R^1$ is

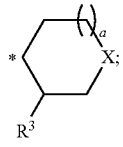

R² is

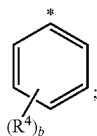

wherein * represents point of attachment; X is CH₂; R³, R⁴, a and b are as defined in the first aspect; or an isotopic form, a stereoisomer or a pharmaceutically acceptable salt thereof.

In yet another embodiment the representative compounds of the present invention includes but not limited to, N-(cis-1S,2S-2-Hydroxycyclohexyl)-4-(2-fluorobenzyl)-4H-benzo[1,4]oxazine-2-carboxamide;
N-(cis-1S,2S-2-Hydroxycyclohexyl)-4-(2-fluorobenzyl)-8-fluoro-4H-benzo[1,4]oxazine-2-carboxamide;
N-(cis-1S,2S-2-Hydroxycyclohexyl)-4-{2-fluorobenzyl}-4H-pyrido[3,2-b][1,4]oxazine-2-carboxamide;
N-(cis-1S,2S-2-Hydroxycyclohexyl)-4-benzyl-4H-benzo[1,4]oxazine-2-carboxamide;
N-(cis-1S, 2S-2-Hydroxycyclohexyl)-4-(4-methoxybenzyl)-4H-benzo[1,4]oxazine-2-carboxamide;
N-(2-Hydroxy-2-methylpropyl)-4-(4-methoxybenzyl)-4H-benzo[1,4]oxazine-2-carboxamide;
N-(cis-1S, 2S-2-Hydroxycyclohexyl)-4-(3-fluorobenzyl)-4H-benzo[1,4]oxazine-2-carboxamide;
N-(2-Hydroxy-2-methylpropyl)-4-(3-fluorobenzyl)-4H-benzo[1,4]oxazine-2-carboxamide;
N-(cis-1S, 2S-2-Hydroxycyclohexyl)-4-(3-methoxybenzyl)-4H-benzo[1,4]oxazine-2-carboxamide;
N-(2-Hydroxy-2-methylpropyl)-4-(3-methoxybenzyl)-4H-benzo[1,4]oxazine-2-carboxamide;
N-(cis-1S,2S-2-Hydroxycyclohexyl)-4-(2-methoxypyridin-4-ylmethyl)-4H-benzo[1,4]oxazine-2-carboxamide;
N-(2-Hydroxy-2-methylpropyl)-4-(2-methoxypyridin-4-ylmethyl)-4H-benzo[1,4]oxazine-2-carboxamide;
N-(cis-1S,2S-2-Hydroxycyclohexyl)-4-(4-fluorobenzyl)-4H-benzo[1,4]oxazine-2-carboxamide;
N-(2-Hydroxy-2-methylpropyl)-4-(4-fluorobenzyl)-4H-benzo[1,4]oxazine-2-carboxamide;
N-(cis-1S,2S-2-Hydroxycyclohexyl)-4-(2-methoxypyridin-5-ylmethyl)-4H-benzo[1,4]oxazine-2-carboxamide;
N-(2-Hydroxy-2-methylpropyl)-4-(2-methoxypyridin-5-ylmethyl)-4H-benzo[1,4]oxazine-2-carboxamide;
N-(cis-1S, 2S-2-Hydroxycyclohexyl)-4-(3-trifluoromethylbenzyl)-4H-benzo[1,4]oxazine-2-carboxamide;
N-(cis-1S, 2S-2-Hydroxycyclohexyl)-4-(2,3-difluorobenzyl)-4H-benzo[1,4]oxazine-2-carboxamide;
N-(cis-1S,2S-2-Hydroxycyclohexyl)-4-(3,4-difluorobenzyl)-4H-benzo[1,4]oxazine-2-carboxamide;
N-(3-Hydroxytetrahydrpyran-4-yl)-4-(2,3-difluorobenzyl)-4H-benzo[1,4]oxazine-2-carboxamide;
N-(cis-1S,2S-2-Hydroxycyclohexyl)-4-(2-chloropyridin-5-ylmethyl)-4H-benzo[1,4]oxazine-2-carboxamide;
N-(cis-1S,2S-2-Hydroxycyclohexyl)-4-(pyridin-3-ylmethyl)-4H-benzo[1,4]oxazine-2-carboxamide;
N-(cis-1S,2S-2-Hydroxycyclohexyl)-4-(pyridin-4-ylmethyl)-4H-benzo[1,4]oxazine-2-carboxamide;
N-(cis-1S,2S-2-Hydroxycyclohexyl)-4-(2-chloropyridin-4-ylmethyl)-4H-benzo[1,4]oxazine-2-carboxamide;
N-(cis-1S,2S-2-Hydroxycyclohexyl)-4-(pyridin-2-ylmethyl)-4H-benzo[1,4]oxazine-2-carboxamide;
N-(cis-1S, 2S-2-Hydroxycyclohexyl)-4-(3,4-dichlorobenzyl)-4H-benzo[1,4]oxazine-2-carboxamide;
N-(cis-1S,2S-2-Hydroxycyclohexyl)-4-(2-methylpyridin-3-ylmethyl)-4H-benzo[1,4]oxazine-2-carboxamide;
N-(cis-1S, 2S-2-Hydroxycyclohexyl)-4-(2,4-dichlorobenzyl)-4H-benzo[1,4]oxazine-2-carboxamide;
N-(cis-1S,2S-2-Hydroxycyclohexyl)-4-(2,3-difluorobenzyl)-8-fluoro-4H-benzo[1,4]oxazine-2-carboxamide;
N-(cis-1S, 2S-2-Hydroxycyclohexyl)-4-benzyl-4H-pyrido[3,2-b][1,4]oxazine-2-carboxamide;
N-(cis-1S,2S-2-Hydroxycyclohexyl)-1-benzyl-1H-pyrido[2,3-b][1,4]oxazine-3-carboxamide;
N-(cis-1S,2S-2-Hydroxycyclohexyl)-1-{2,3-difluorobenzyl}-1H-pyrido[2,3-b][1,4]oxazine-3-carboxamide;
N-(cis-1S,2S-2-Hydroxycyclohexyl)-4-(2,3-difluorobenzyl)-4H-pyrido[3,2-b][1,4]oxazine-2-carboxamide;
N-(cis-1S,2S-2-Hydroxycyclohexyl)-4-(3-fluoropyridin-4-ylmethyl)-4H-benzo[1,4]oxazine-2-carboxamide;
N-(cis-1S,2S-2-Hydroxycyclohexyl)-4-(4-fluorobenzyl)-4H-pyrido[3,2-b][1,4]oxazine-2-carboxamide;
N-(cis-1S,2S-2-Hydroxycyclohexyl)-1-(3-fluorobenzyl)-1H-pyrido[2,3-b][1,4]oxazine-3-carboxamide;
N-(cis-1S, 2S-2-Hydroxycyclohexyl)-4-(2-trifluoromethylbenzyl)-4H-benzo[1,4]oxazine-2-carboxamide;
N-(cis-1S, 2S-2-Hydroxycyclohexyl)-4-(2-chlorobenzyl)-8-fluoro-4H-benzo[1,4]oxazine-2-carboxamide;
N-(trans-1R,2R-2-Hydroxycyclopentyl)-4-(2,3-difluorobenzyl)-4H-benzo[1,4]oxazine-2-carboxamide;
N-(trans-1R,2R-2-Hydroxycyclopentyl)-4-(2-fluorobenzyl)-4H-benzo[1,4]oxazine-2-carboxamide;
N-(cis-1S, 2S-2-Hydroxycyclohexyl)-4-(2-chlorobenzyl)-4H-benzo[1,4]oxazine-2-carboxamide;
N-(trans-1R,2R-2-Hydroxycyclopentyl)-4-(2,3-difluorobenzyl)-8-fluoro-4H-benzo[1,4]oxazine-2-carboxamide;
N-(2-Hydroxymethylphenyl)-4-(2-fluorobenzyl)-4H-benzo[1,4]oxazine-2-carboxamide;
N-(2-Hydroxymethylphenyl)-4-(2,3-difluorobenzyl)-8-fluoro-4H-benzo[1,4]oxazine-2-carboxamide;
N-(2-Hydroxymethylphenyl)-4-(2,3-difluorobenzyl)-4H-benzo[1,4]oxazine-2-carboxamide;
N-(2-Hydroxymethylphenyl)-4-(2-fluorobenzyl)-8-fluoro-4H-benzo[1,4]oxazine-2-carboxamide;
N-(1-Hydroxymethyl-2-methylpropyl)-4-(2-fluorobenzyl)-8-fluoro-4H-benzo[1,4]oxazine-2-carboxamide;
N-(cis-1S,2S-2-Hydroxycyclohexyl)-4-benzyl-8-fluoro-4H-benzo[1,4]oxazine-2-carboxamide;
N-(cis-1R, 2R-2-Hydroxycyclohexyl)-4-{2-fluorobenzyl}-4H-benzo[1,4]oxazine-2-carboxamide;
N-(cis-1R,2R-2-Hydroxycyclohexyl)-4-{2-fluorobenzyl}-8-fluoro-4H-benzo[1,4]oxazine-2-carboxamide;
N-(cis-1S,2S-2-Hydroxycyclohexyl)-4-{3-fluorobenzyl}-8-fluoro-4H-benzo[1,4]oxazine-2-carboxamide;
N-(cis-1S,2S-2-Hydroxycyclohexyl)-4-(2-phenylpyridin-4-ylmethyl)-4H-benzo[1,4]oxazine-2-carboxamide;
N-(cis-1S,2S-2-Hydroxycyclohexyl)-4-(2-phenylpyridin-4-ylmethyl)-8-fluoro-4H-benzo[1,4]oxazine-2-carboxamide;
N-(cis-1S,2S-2-Hydroxycyclohexyl)-4-(2-chloropyridin-4-ylmethyl)-8-fluoro-4H-benzo[1,4]oxazine-2-carboxamide;
N-(cis-1S,2S-2-Hydroxycyclohexyl)-4-(2-fluorobenzyl)-5-fluoro-4H-benzo[1,4]oxazine-2-carboxamide;
N-(cis-1S,2S-2-Hydroxycyclohexyl)-4-(pyridin-2-ylmethyl)-5-fluoro-4H-benzo[1,4]oxazine-2-carboxamide;
N-(cis-1S,2S-2-Hydroxycyclohexyl)-4-(pyridin-4-ylmethyl)-8-fluoro-4H-benzo[1,4]oxazine-2-carboxamide;

N-(cis-1S,2S-2-Hydroxycyclohexyl)-4-(6'-fluoro-5'-methyl-[2,3']bipyridinyl-4-ylmethyl)-4H-benzo[1,4]oxazine-2-carboxamide;
N-(cis-1S,2S-2-Hydroxycyclohexyl)-4-[12-(1-methyl-1H-pyrazol-3-yl)-pyridin-4-ylmethyl]-4H-benzo[1,4]oxazine-2-carboxamide;
N-(cis-1S,2S-2-Hydroxycyclohexyl)-4-(1-methyl-1H-pyrazol-3-ylmethyl)-4H-benzo[1,4]oxazine-2-carboxamide;
N-(cis-1S,2S-2-Hydroxycyclohexyl)-4-(2-fluorobenzyl)-5,8-difluoro-4H-benzo[1,4]oxazine-2-carboxamide;
N-(cis-1S,2S-2-Hydroxycyclohexyl)-4-(3-fluoropyridin-4-ylmethyl)-8-fluoro-4H-benzo[1,4]oxazine-2-carboxamide;
N-(cis-1S,2S-2-Hydroxycyclohexyl)-4-(2-methylpyridin-4-ylmethyl)-8-fluoro-4H-benzo[1,4]oxazine-2-carboxamide;
N-(cis-1S,2S-2-Hydroxycyclohexyl)-4-(2-methylpyridin-5-ylmethyl)-8-fluoro-4H-benzo[1,4]oxazine-2-carboxamide;
N-(cis-1S, 2S-2-Hydroxycyclohexyl)-4-(2-methylpyridin-4-ylmethyl)-4H-benzo[1,4]oxazine-2-carboxamide;
N-(cis-1S, 2S-2-Hydroxycyclohexyl)-4-(2-methylpyridin-5-ylmethyl)-4H-benzo[1,4]oxazine-2-carboxamide;
N-(cis-1S,2S-2-Hydroxycyclohexyl)-4-(pyridin-4-ylmethyl)-5,8-difluoro-4H-benzo[1,4]oxazine-2-carboxamide;
N-(3-Hydroxytetrahydropyran-4-yl)-4-(3-fluorobenzyl)-4H-benzo[1,4]oxazine-2-carboxamide;
N-(3-Hydroxytetrahydropyran-4-yl)-4-(4-fluorobenzyl)-8-fluoro-4H-benzo[1,4]oxazine-2-carboxamide;
N-(3-Hydroxytetrahydropyran-4-yl)-4-(3-trifluoromethylbenzyl)-4H-benzo[1,4]oxazine-2-carboxamide;
N-(3-Hydroxytetrahydropyran-4-yl)-4-(2-methoxypyridin-5-ylmethyl)-4H-benzo[1,4]oxazine-2-carboxamide;
N-(3-Hydroxytetrahydropyran-4-yl)-4-(pyridin-4-ylmethyl)-8-fluoro-4H-benzo[1,4]oxazine-2-carboxamide;
N-(3-Fluoropiperidin-4-yl)-4-(2-fluorobenzyl)-8-fluoro-4H-benzo[1,4]oxazine-2-carboxamide;
N-(3-Fluoropiperidin-4-yl)-4-(2,3-difluorobenzyl)-8-fluoro-4H-benzo[1,4]oxazine-2-carboxamide;
N-(3-Hydroxypiperidin-4-yl)-4-(2,3-difluorobenzyl)-8-fluoro-4H-benzo[1,4]oxazine-2-carboxamide;
N-(3-Hydroxypiperidin-4-yl)-4-(2-fluorobenzyl)-4H-benzo[1,4]oxazine-2-carboxamide;
N-(cis-1S,2S-2-Hydroxycyclohexyl)-4-(2,3-difluorobenzyl)-4H-benzo[1,4]thiazine-2-carboxamide;
N-(cis-1S,2S-2-Hydroxycyclohexyl)-4-(3-fluorobenzyl)-4H-benzo[1,4]thiazine-2-carboxamide;
N-(cis-1S,2S-2-Hydroxycyclohexyl)-4-benzyl-4H-benzo[1,4]thiazine-2-carboxamide;
N-(cis-1S,2S-2-Hydroxycyclohexyl)-4-{4-methoxybenzyl}-4H-benzo[1,4]thiazine-2-carboxamide;
N-(cis-1S,2S-2-Hydroxycyclohexyl)-4-{4-fluorobenzyl}-4H-benzo[1,4]thiazine-2-carboxamide;
N-(cis-1S,2S-2-Hydroxycyclohexyl)-4-{pyridin-4-ylmethyl}-4H-benzo[1,4]thiazine-2-carboxamide;
N-(cis-1S,2S-2-Hydroxycyclohexyl)-4-{2-chloropyridin-5-ylmethyl}-4H-benzo[1,4]thiazine-2-carboxamide;
N-(cis-1S,2S-2-Hydroxycyclohexyl)-4-{pyridin-2-ylmethyl}-4H-benzo[1,4]thiazine-2-carboxamide;
N-(cis-1 S, 2S-2-Hydroxycyclohexyl)-4-(2,3-difluorobenzyl)-1-oxo-4H-benzo[1,4]thiazine-2-carboxamide;
N-(cis-1S,2S-2-Hydroxycyclohexyl)-4-benzyl-1-oxo-4H-benzo[1,4]thiazine-2-carboxamide;
N-(cis-1S,2S-2-Hydroxycyclohexyl)-4-{3-fluorobenzyl}-1-oxo-4H-benzo[1,4]thiazine-2-carboxamide;
N-(cis-1 S, 2S-2-Hydroxycyclohexyl)-4-{pyridin-2-ylmethyl}-1-oxo-4H-benzo[1,4]thiazine-2-carboxamide;
N-(cis-1S, 2S-2-Hydroxycyclohexyl)-4-{2-chloropyridin-5-ylmethyl}-1-oxo-4H-benzo[1,4]thiazine-2-carboxamide;
N-(3-Hydroxypiperidin-4-yl)-4-(4-fluorobenzyl)-8-fluoro-4H-benzo[1,4]oxazine-2-carboxamide;
N-(3-Hydroxypiperidin-4-yl)-4-(4-fluorobenzyl)-4H-benzo[1,4]oxazine-2-carboxamide;
N-(3-Hydroxypiperidin-4-yl)-4-(2,3-difluorobenzyl)-4H-benzo[1,4]oxazine-2-carboxamide; and
N-(3-Hydroxypiperidin-4-yl)-4-(2-fluorobenzyl)-8-fluoro-4H-benzo[1,4]oxazine-2-carboxamide;
or their pharmaceutically acceptable salt thereof.

In yet another embodiment the representative compounds of pharmaceutically acceptable salt of the present invention includes but not limited to,
N-(3-Fluoropiperidin-4-yl)-4-(2-fluorobenzyl)-8-fluoro-4H-benzo[1,4]oxazine-2-carboxamide hydrochloride;
N-(3-Fluoropiperidin-4-yl)-4-(2,3-difluorobenzyl)-8-fluoro-4H-benzo[1,4]oxazine-2-carboxamide hydrochloride;
N-(3-Hydroxypiperidin-4-yl)-4-(2,3-difluorobenzyl)-8-fluoro-4H-benzo[1,4]oxazine-2-carboxamide trifluoroacetate;
N-(3-Hydroxypiperidin-4-yl)-4-(2-fluorobenzyl)-4H-benzo[1,4]oxazine-2-carboxamide trifluoroacetate;
N-(3-Hydroxypiperidin-4-yl)-4-(4-fluorobenzyl)-8-fluoro-4H-benzo[1,4]oxazine-2-carboxamide trifluoroacetate;
N-(3-Hydroxypiperidin-4-yl)-4-(4-fluorobenzyl)-4H-benzo[1,4]oxazine-2-carboxamide trifluoroacetate;
N-(3-Hydroxypiperidin-4-yl)-4-(2,3-difluorobenzyl)-4H-benzo[1,4]oxazine-2-carboxamide trifluoroacetate; and
N-(3-Hydroxypiperidin-4-yl)-4-(2-fluorobenzyl)-8-fluoro-4H-benzo[1,4]oxazine-2-carboxamide trifluoroacetate.

General Scheme-1 depicts processes for the preparation of the intermediates, wherein W is O and S; $A^1$, $A^2$, and $R^2$ are as defined in the first aspect.

General Scheme -1

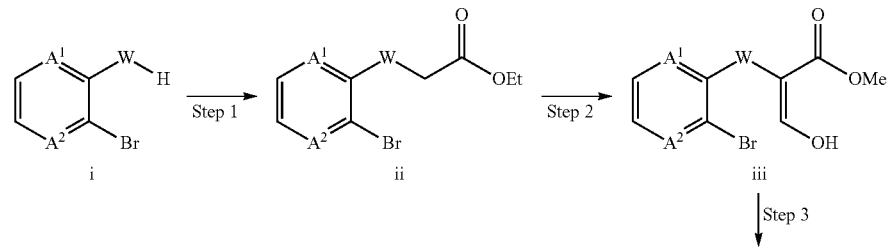

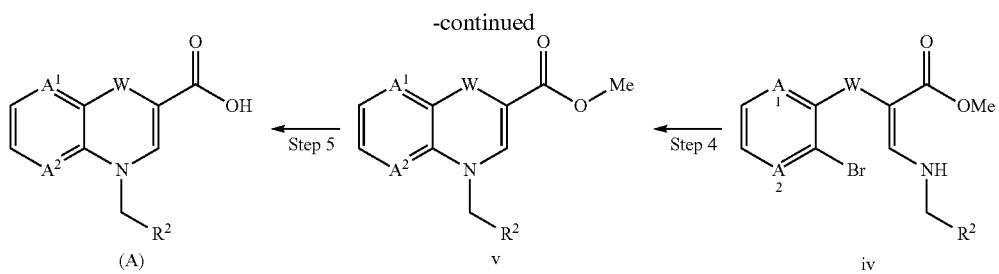

Step 1: Preparation of Compound of Formula (ii)

The compound of formula (i) is reacted with ethyl bromoacetate in presence of base selected from cesium carbonate, potassium carbonate, sodium carbonate, sodium bicarbonate, sodium hydroxide and potassium hydroxide in a solvent selected from acetonitrile, DCM, DCE, acetone, THF, DMF and DMSO at a temperature range of 80-100° C. for 15-17 hours to obtain the compound of formula (ii).

Step 2: Preparation of Compound of Formula (iii)

The compound of formula (ii) obtained in step 1 is reacted with methyl formate in presence of sodium hydride, sodium tert-butoxide, potassium tert-butoxide, lithium diisopropylamide (LDA) or lithium hexamethyldisilazide (LiHMDS) at 0° C. to RT for 3-5 hours to obtain the compound of formula (iii).

Step 3: Preparation of Compound of Formula (iv)

The compound of formula (iii) obtained in step 2 is reacted with amine, $R^2$—$CH_2$—$NH_2$ in a solvent selected from methanol, ethanol and isopropanol at the temperature range of 25-30° C., for 10-14 hours to obtain the compound of formula (iv). The amines, $R^2$—$CH_2$—$NH_2$ were either procured from commercial sources or prepared from either by their respective halides/mesylates/tosylates through azides or by reduction of respective nitriles. The halides/mesylates/tosylates were displaced with azide using sodium azide in solvents selected from DMSO, DMF, DMA and NMP at the temperature range of from RT to 110° C. The azides and nitriles were reduced to amines using reducing agents selected from $PPh_3/H_2O$, $Pd/C/H_2$, Raney nickel and $NaBH_4/NiCl_2$ in solvents selected from THF, MeOH, EtOH and $H_2O$ at temperature range of 0° C. to RT.

Step 4: Preparation of Compound of Formula (v)

The compound of formula (iv) obtained in step 3 is reacted with copper iodide, copper chloride or copper bromide in presence of base selected from cesium carbonate, potassium carbonate or potassium phosphate in a solvent selected from DMF, NMP, DMA, DMSO, THF and DCE at temperature ranging from RT to 90° C. for 5-7 hours to obtain the compound of formula (v).

Step 5: Preparation of Compound of Formula (A)

The compound of formula (v) obtained in step 4 is reacted with sodium hydroxide in a 1:1 mixture of water and methanol under reflux for 3-5 hours to obtain the compound of formula (A).

General Scheme-2 depicts processes for the preparation of compound of formula (I), wherein $A^1$, $A^2$, W, $R^1$, $R^2$, $R^3$ and $R^4$ are as defined above.

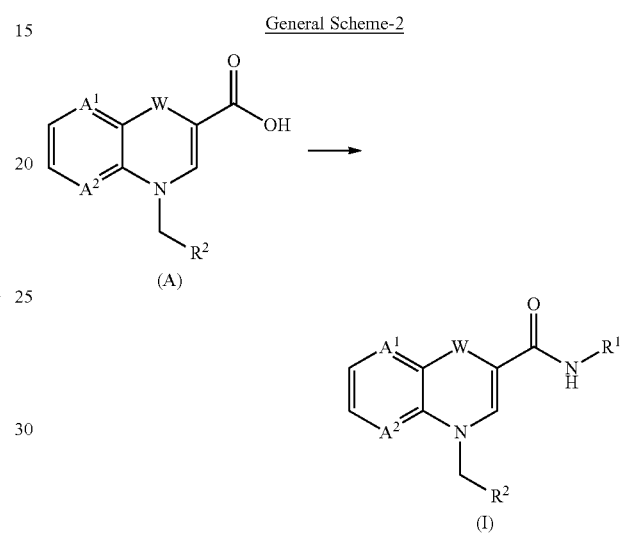

General Scheme-2

Preparation of Compound of Formula (I)

The compound of formula (A) is coupled with amine, $R^1$—$NH_2$ in presence of coupling reagents such as HATU, DCC, DIC, TBTU or EDC and organic base such as DIPEA, TEA, DABCO and DBU in a solvent selected from DCM, DMF, DMA, NMP and THF at a temperature range of 25-30° C. for 15-17 hours to obtain the compound of formula (I). The amines of $R^1$—$NH_2$, such as (1S,2S)-2-aminocyclohexanol (CAS No. 13374-30-6), (1R,2R)-2-aminocyclohexanol (CAS No. 931-16-8), 1-amino-2-methyl-2-propanol, 2-amino-3-methyl-1-butanol, 2-aminobenzyl alcohol, (1R,2R)-trans-2-aminocyclopentanol (CAS No. 68327-11-7) and trans 4-amino tetrahydropyran-3-ol (CAS No. 215940-92-4) were procured from commercial sources, whereas tert-butyl 4-amino-3-hydroxy piperidine-1-carboxylate was prepared using the procedures as disclosed in EP0076530A2 and tert-butyl 4-amino-3-fluoro piperidine-1-carboxylate was prepared using the procedures as disclosed in WO2012108490A1.

Preparation of Compound of Formula (I) (Wherein W is S(=O))

The compound of formula (I) (wherein W is S) is reacted with $NaIO_4$ in a solvent selected from 1:1:2 mixture of methanol, THF and water at a temperature range of 25-30° C. for 14-17 hours to obtain the compound of formula (I) (wherein W is S(=O)). Preparation of pharmaceutically acceptable salt of compound of formula (I)

The compound of formula (I) can be optionally converted into its pharmaceutically acceptable salt by reaction with the appropriate acid or acid derivative.

Suitable pharmaceutically acceptable salts will be apparent to those skilled in the art. The salts are formed with inorganic acids e. g. hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing same are well known in the art.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

In yet another aspect, the present invention relates to method of treatment of disorders related to muscarinic M1 receptors.

In another embodiment, the disorders related to muscarinic M1 receptors are selected from the group consisting of AD, schizophrenia, cognitive disorders, pain or sleep disorders.

In yet another embodiment, the present invention relates to method of treatment of disorders related to muscarinic M1 receptors comprising the compound of formula (I) in combination with other therapeutic agents selected from cholinesterase inhibitors e.g., donepezil, and NMDA receptor antagonist e.g., memantine.

Commercial reagents were used without further purification. RT is defined as an ambient temperature range, typically from 25° C. to 35° C. All mass spectra were obtained using ESI conditions unless otherwise stated. $^1$H-NMR spectra were recorded at 400 MHz on a Bruker instrument. Deuterated chloroform, methanol or dimethyl sulfoxide was used as solvent. TMS was used as internal reference standard. Chemical shift values are expressed in parts per million (δ) values. The following abbreviations are used for the multiplicity of the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The stereoisomers as a rule are generally obtained as racemates that can be separated into the optically active isomers in a manner known per se. In the case of the compounds of general formula (I) having an asymmetric carbon atom the present invention relates to the D-form, the L-form and D, L-mixtures and in the case of compound of general formula (I) containing a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines. (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative.
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

The following abbreviations are used herein:
CuI: Copper Iodide
$Cs_2CO_3$: Cesium Carbonate
DCM: Dichloromethane
DCE: Dichloroethane
DCC: N,N'-Dicyclohexylcarbodiimide
DIC: N,N'-Diisopropylcarbodiimide
DIPEA: N,N-Diisopropylethylamine
DBU: 1,8-Diazabicyclo[5.4.0]undec-7-ene
DABCO: 1,4-Diazabicyclo[2.2.2]octane
DMA: Dimethylacetamide
DMF: N,N-Dimethylformamide
DMSO: Dimethyl sulfoxide
EDC: Ethylene dichloride
$H_2$: Hydrogen gas
HATU: 2-(7-Aza-1H-benzotriazole-1-yl)-1,1,3,3-tetramethyluronium hexafluorophosphate
HCl: Hydrochloric acid
IPA: Isopropyl alcohol
$K_3PO_4$: Potassium phosphate
MeOH: Methanol
$NaHCO_3$: Sodium bicarbonate
$NaIO_4$: Sodium metaperiodate
NaOH: Sodium hydroxide
$Na_2SO_4$: Sodium sulfate
NMP: N-Methyl-2-pyrrolidinone
$NiCl_2$: Nickel chloride
$NaBH_4$: Sodium borohydride
$PPh_3$: Triphenylphosphine
RT: Room temperature (25-30° C.)
TBTU: O-(Benzotriazol-1-yl)-N,N,N',N'-tetramethyluronium tetrafluoroborate TEA: Triethylamine
THF: Tetrahydrofuran
TMS: Tetramethylsilane

INTERMEDIATES PREPARATION

Intermediate 1

2,3-Difluorobenzylamine (I-1)

Step 1: Preparation of 1-azidomethyl-2,3-difluorobenzene

To a stirred solution of 1-bromomethyl-2,3-difluorobenzene (50.0 g, 241.5 mmol) in DMF (483.0 mL) at RT, sodium azide (23.5 g, 362.3 mmol) was added over a period of 15 minutes and the reaction mixture was stirred at RT for 16 hours. The reaction mixture was diluted with ether and washed with water. The organic layer was dried over anhydrous $Na_2SO_4$ and the volatiles were removed under reduced pressure to obtain the title compound.

Yield: 43.4 g. $^1$H-NMR (400 MHz, $CDCl_3$): δ 7.22-7.05 (m, 3H), 4.44 (s, 2H).

Step 2: Preparation of 2,3-difluorobenzylamine

To a stirred solution of 1-azidomethyl-2,3-difluorobenzene (41.3 g, 244.3 mmol) obtained in the above step in THF (490.0 mL) at 0° C., triphenylphosphine (70.4 g, 268.8 mmol) and water (13.2 mL, 733.0 mmol) were added. The reaction mixture was stirred at RT for 16 hours and diluted with ethyl acetate. The reaction mass was washed with water and brine, dried over anhydrous $Na_2SO_4$ and the solvent was removed under reduced pressure. The crude mass obtained was purified by silica gel column chromatography to obtain the title compound.

Yield: 23.1 g; $^1$H-NMR (400 MHz, $CDCl_3$): δ 7.15-7.0 (m, 3H), 3.93 (s, 2H); Mass (m/z): 144.1 $(M+H)^+$.

Using the above experimental procedure, the following substituted benzyl amines were prepared starting from the respective commercially available benzyl halides through azide intermediates.

Intermediate 2

3-Trifluoromethylbenzylamine (I-2)

$^1$H-NMR (400 MHz, $CDCl_3$): δ 7.60 (s, 1H), 7.58-7.43 (m, 3H), 3.95 (s, 2H); Mass (m/z): 176.4 $(M+H)^+$.

Intermediate 3

4-Pyrazol-1-yl benzylamine (I-3)

$^1$H-NMR (400 MHz, $CDCl_3$): δ 7.92 (d, J=2.1 Hz, 1H), 7.72 (s, 1H), 7.67 (d, J=8.3 Hz, 2H), 7.41 (d, J=8.3 Hz, 2H), 6.46 (d, J=2.1 Hz, 1H), 3.91 (s, 2H); Mass (m/z): 174.0 $(M+H)^+$.

Intermediate 4

3,4-Difluorobenzylamine (I-4)

$^1$H-NMR (400 MHz, $CDCl_3$): δ 7.22-7.08 (m, 2H), 7.08-7.03 (m, 1H), 3.85 (s, 2H); Mass (m/z): 144.1 $(M+H)^+$.

Intermediate 5

2,4-Dichlorobenzylamine (I-5)

$^1$H-NMR (400 MHz, $CDCl_3$): δ 7.70-7.50 (m, 3H), 3.75 (s, 2H). Mass (m/z): 176.2, 178.1 $(M+H)^+$.

Intermediate 6

4-Pyridylmethylamine (I-6)

To a stirred solution of 4-cyanopyridine (100.0 mg, 0.96 mmol) in methanol (4.0 mL) at RT, 10% Pd/C (50.0 mg) was added and stirred for 3 hours under hydrogen atmosphere. The reaction mass was filtered through a pad of celite and the volatiles were removed under reduced pressure to obtain the title compound.

Yield: 63.6 mg; $^1$H-NMR (400 MHz, $CDCl_3$): δ 8.52 (d, J=4.7 Hz, 2H), 7.23 (d, J=4.7 Hz, 2H), 3.88 (s, 2H); Mass (m/z): 109.2 $(M+H)^+$.

Using the above experimental procedure, the following substituted pyridyl amines were prepared starting from the respective commercially available pyridyl nitriles.

Intermediate 7

3-Aminomethylpyridine (I-7)

$^1$H-NMR (400 MHz, $CDCl_3$): δ 8.58 (s, 1H), 8.52 (d, J=4.0 Hz, 1H), 7.70 (d, J=7.5 Hz, 1H), 7.30 (t, J=5.9 Hz, 1H), 3.92 (s, 2H); Mass (m/z): 109.1 $(M+H)^+$.

Intermediate 8

2-Aminomethyl-6-methylpyridine (I-8)

$^1$H-NMR (400 MHz, $CDCl_3$): δ 7.62-7.51 (m, 1H), 7.20-7.0 (m, 2H), 4.12-4.0 (m, 2H), 2.54 (s, 3H); Mass (m/z): 123.0 $(M+H)^+$.

Intermediate 9

3-Fluoro-4-aminomethylpyridine (I-9)

$^1$H-NMR (400 MHz, $CDCl_3$): δ 7.43-7.36 (m, 2H), 7.35-7.26 (m, 1H), 3.91 (s, 2H); Mass (m/z): 127.1 $(M+H)^+$.

Intermediate 10

2-Phenyl-4-aminomethylpyridine (I-10)

Step 1: Preparation of 2-phenyl-4-cyanopyridine

To a stirred solution of 2-chloro-4-cyanopyrdine (500 mg, 3.61 mmol) in a 1:1 mixture of DMF and water (18 mL) at RT, phenylboronic acid (524.1 mg, 4.33 mmol), $PPh_3$ (2.8 mg, 0.01 mmol), $Pd_2(dba)_3$ (16.5 mg, 0.018 mmol) were sequentially added. The reaction temperature was then raised to 110° C. and stirred the contents at this temperature for 1 hour. The reaction mass was diluted with ether, washed with water, brine, dried over anhydrous $Na_2SO_4$ and the solvent was removed under reduced pressure to obtain the title compound.

Yield: 43.4 g; $^1$H-NMR (400 MHz, $CDCl_3$): δ 8.86 (d, J=4.9 Hz, 1H), 8.01 (d, J=7.8 Hz, 2H), 7.94 (s, 1H), 7.58-7.48 (m, 3H), 7.45 (d, J=4.9 Hz, 1H); Mass (m/z): 181.2 $(M+H)^+$.

Step 2: Preparation of 2-phenyl-4-aminomethylpyridine

To a stirred solution of 2-phenyl-4-cyanopyridine (625.0 mg, 3.4 mmol) in methanol (17.0 mL) at RT, 10% Pd/C (312.0 mg) was added and stirred for 3 hours under hydrogen atmosphere. The reaction mass was filtered through a pad of celite and the volatiles were removed under reduced pressure to obtain the title compound.

Yield: 63.6 mg; $^1$H-NMR (400 MHz, CDCl$_3$): δ 8.63 (d, J=5.0 Hz, 1H), 7.71 (s, 1H), 7.50-7.36 (m, 5H), 7.15 (d, J=7.6 Hz, 1H), 3.97 (s, 2H); Mass (m/z): 185.1 (M+H)$^+$.

Using the above experimental procedure, the following intermediate was prepared with some non-critical variation.

Intermediate 11

2-(2-Fluoro-3-methylpyridine-5-yl)-4-aminomethyl-pyridine (I-11)

$^1$H-NMR (400 MHz, CDCl$_3$): δ 8.63 (dd, J=5.0, 7.6 Hz, 1H), 8.58 (d, J=6.2 Hz, 1H), 8.32-8.26 (m, 1H), 7.74-7.70 (m, 1H), 7.35-7.25 (m, 1H), 3.99 (s, 2H), 2.36 (s, 3H); Mass (m/z): 218.1 (M+H)$^+$.

Intermediate 12

Ethyl 2-bromophenoxy acetate (I-12)

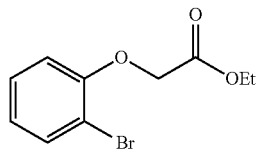 [SMILES: CCOC(=O)COc1ccccc1Br]

To a solution of 2-bromophenol (30.2 g, 174.6 mmol), Cs$_2$CO$_3$ (85.3 g 261.8 mmol) in acetonitrile (350 mL), ethyl bromoacetate (23.2 mL, 209.5 mmol) was added over a period of 15 minutes at RT and reaction mixture was stirred at RT for 15 minutes.

The temperature of the reaction mixture was gradually raised to reflux and stirred for 16 hours under refluxing until the starting phenol was consumed as indicated by TLC. The reaction mass was cooled to RT, filtered through a pad of celite and the filtrate was concentrated under vacuum to dryness. The residue was dissolved in ethyl acetate, washed with water and brine, dried over anhydrous Na$_2$SO$_4$ and the solvent was evaporated under reduced pressure to obtain the title compound.

Yield: 43.8 g; $^1$H-NMR (400 MHz, CDCl$_3$): δ 7.57 (d, J=8.0 Hz, 1H), 7.24 (t, J=8.9 Hz, 1H), 6.88 (t, J=7.8 Hz, 1H), 6.82 (d, J=8.3 Hz, 1H), 4.69 (s, 2H), 4.27 (q, 2H), 1.29 (t, J=7.1 Hz, 3H); Mass (m/z): 281.1, 283.1 (M+Na)$^+$.

Using the above experimental procedure, the following intermediates, I-13 to I-17 were prepared.

Intermediate 13

Ethyl 2-bromo-6-fluoro phenoxy acetate (I-13)

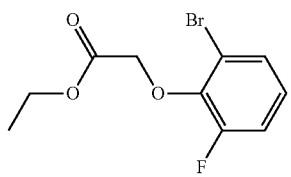

$^1$H-NMR (400 MHz, CDCl$_3$): δ 7.34 (d, J=7.7 Hz, 1H), 7.15-7.05 (m, 1H), 7.0-6.91 (m, 1H), 4.72 (s, 2H), 4.28 (q, 2H), 1.30 (t, J=7.0 Hz, 3H); Mass (m/z): 299.0, 301.1 (M+Na)$^+$.

Intermediate 14

Ethyl 3-bromo pyridin-2-yloxy acetate (I-14)

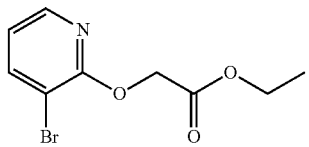

$^1$H-NMR (400 MHz, CDCl$_3$): δ 8.36 (d, J=1.0 Hz, 1H), 7.95 (d, J=6.3 Hz, 1H), 7.15-7.05 (m, 1H), 4.94 (s, 2H), 4.25 (q, 2H), 1.29 (t, J=6.9 Hz, 3H); Mass (m/z): 260.1, 262.1 (M+H)$^+$.

Intermediate 15

Ethyl 2-fluoro pyridin-3-yloxy acetate (I-15)

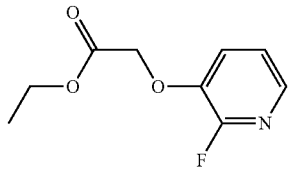

$^1$H-NMR (400 MHz, CDCl$_3$): δ 7.82 (d, J=3.6 Hz, 1H), 7.29 (d, J=10.8 Hz, 1H), 7.12 (t, J=2.8 Hz, 1H), 4.71 (s, 2H), 4.24 (q, 2H), 1.27 (t, J=7.1 Hz, 3H); Mass (m/z): 200.2 (M+H)$^+$.

Intermediate 16

Ethyl 2-bromo-3-fluoro phenoxy acetate (I-16)

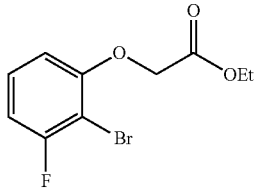 [SMILES: CCOC(=O)COc1cccc(F)c1Br]

$^1$H-NMR (400 MHz, CDCl$_3$): δ7.25-7.0 (m, 1H), 6.81 (t, J=8.0 Hz, 1H), 6.60 (d, J=8.3 Hz, 1H), 4.71 (s, 2H), 4.27 (q, 2H), 1.30 (t, J=6.9 Hz, 3H); Mass (m/z): 277.0, 279.0 (M+H)$^+$.

Intermediate 17

Ethyl 2-bromo-3,6-difluoro phenoxy acetate (I-17)

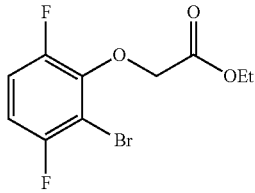 [SMILES: CCOC(=O)COc1c(F)ccc(F)c1Br]

$^1$H-NMR (400 MHz, CDCl$_3$): δ 7.10-7.0 (m, 1H), 6.90-6.82 (m, 1H), 4.78 (s, 2H), 4.27 (q, 2H), 1.30 (t, J=6.9 Hz, 3H); Mass (m/z): 294.0, 296.0 (M+H)$^+$.

Intermediate 18

Ethyl 2-bromophenylsulfanyl acetate (I-18)

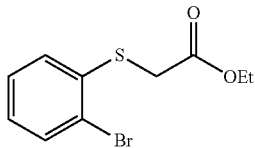

To a solution of 2-bromothiophenol (10.0 g, 52.9 mmol), Cs$_2$CO$_3$ (25.8 g, 79.4 mmol) in acetonitrile (210 mL) at RT, ethyl bromoacetate (7.0 mL, 63.5 mmol) was added over a period of 15 minutes. The reaction mixture was stirred at RT for 15 minutes and the reaction mixture was refluxed (80-85° C.) for 16 hours until the starting phenol was consumed as indicated by TLC. The reaction mixture was cooled to RT, filtered through a pad of celite and the filtrate was concentrated under vacuum to dryness. The residue was dissolved in ethyl acetate, washed with water, brine, dried over anhydrous Na$_2$SO$_4$ and the solvent was evaporated under reduced pressure to obtain the title compound.

Yield: 13.8 g; $^1$H-NMR (400 MHz, CDCl$_3$): δ 7.61 (d, J=5.5 Hz, 1H), 7.42 (d, J=7.9 Hz, 1H), 7.30 (t, J=7.2 Hz, 1H), 7.10 (t, J=8.0 Hz, 1H), 4.21 (q, 2H), 3.70 (s, 2H), 1.26 (t, J=7.1 Hz, 3H); Mass (m/z): 275.0, 277.1 (M+H)$^+$.

Intermediate 19

Methyl 2-(2-bromophenoxy)-3-hydroxy acrylate (I-19)

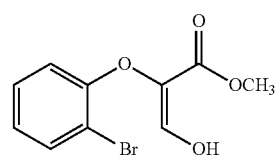 [SMILES: COC(=O)/C(=C\O)Oc1ccccc1Br]

To a stirred solution of the intermediate, I-12 (18.02 g, 69.5 mmol) in methyl formate (105.3 mL) cooled at 0° C., a suspension of sodium hydride (11.1 g, 278.0 mmol, 60% oil dispersion) was slowly added over 0.5 hour and stirred for 4 hours. The reaction mixture was treated with ice cold water (400 mL) and separated aqueous layer. The aqueous layer was acidified with 1N HCl and then extracted with ethyl acetate. The organic layers were combined, washed with water, saturated solution of NaHCO$_3$ and finally with brine. The organic layer was dried over anhydrous Na$_2$SO$_4$ and the solvent was removed under reduced pressure to obtain a crude product (18.9 g) as a mixture of isomers with sufficient purity for use in the next reactions without additional purification.

$^1$H-NMR (400 MHz, DMSO-d$_6$): δ 11.1 (bs, 1H), 7.64 (s, 1H), 7.58 (d, J=7.7 Hz, 1H), 7.25 (t, J=7.8 Hz, 1H), 6.90 (t, J=7.5 Hz, 1H), 6.82 (d, J=8.2 Hz, 1H), 3.61 (s, 3H); Mass (m/z): 271.2, 273.1 (M–H)$^+$.

Using the above reaction procedure the following intermediates, I-20 to I-24 were prepared using the intermediates I-13 to I-17.

Intermediate 20

Methyl 2-(2-bromo-6-fluorophenoxy)-3-hydroxy acrylate (I-20)

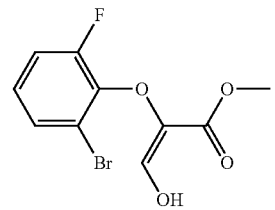 [SMILES: COC(=O)/C(=C\O)Oc1c(F)cccc1Br]

$^1$H-NMR (400 MHz, CDCl$_3$): δ 7.45-7.32 (m, 2H), 7.18-6.95 (m, 2H), 3.68 (s, 3H); Mass (m/z): 313.0, 315.1 (M+Na)$^+$.

Intermediate 21

Methyl 2-(3-bromopyridin-2-yloxy)-3-hydroxy acrylate (I-21)

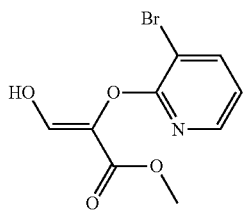

$^1$H-NMR (400 MHz, CDCl$_3$): δ 8.04 (d, J=1.2 Hz, 1H), 7.05 (d, J=6.5 Hz, 1H), 6.84 (t, 1H), 3.78 (s, 3H); Mass (m/z): 246.0, 248.1 (M+H)$^+$.

Intermediate 22

Methyl 2-(2fluoro pyridin-3-yloxy)-3-hydroxy acrylate (I-22)

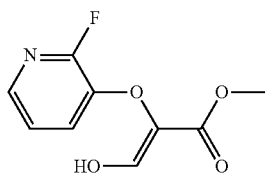

Mass (m/z): 213.2 (M+H)$^+$.

Intermediate 23

Methyl 2-(2-bromo-3-fluorophenoxy)-3-hydroxy acrylate (I-23)

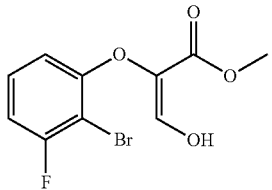 [SMILES: COC(=O)/C(=C\O)Oc1cccc(F)c1Br]

$^1$H-NMR (400 MHz, CDCl$_3$): δ 7.26-7.15 (m, 2H), 6.90-6.80 (m, 1H), 6.70-6.60 (m, 1H), 3.82 (s, 3H); Mass (m/z): 289.0, 291.2 (M–H)$^+$.

Intermediate 24

Methyl 2-(2-bromo-3,6-difluorophenoxy)-3-hydroxy acrylate (I-24)

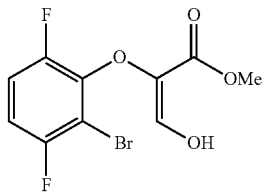 [SMILES: COC(=O)/C(=C\O)Oc1c(F)ccc(F)c1Br]

$^1$H-NMR (400 MHz, CDCl$_3$): δ 7.15-6.80 (m, 3H), 3.90 (s, 3H); Mass (m/z): 307.0, 309.0 (M–H)$^+$.

Intermediate 25

Methyl 2-(2-bromophenylsulfanyl)-3-hydroxy acrylate (I-25)

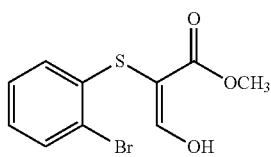 [SMILES: COC(=O)/C(=C\O)Sc1ccccc1Br]

To a stirred solution of the intermediate, I-18 (16.0 g, 58.2 mmol) in methyl formate (88.1 mL) cooled at 0° C., a suspension of sodium hydride (9.3 g 232.7 mmol, 60% oil dispersion) was slowly added over 0.5 h. The reaction mixture was stirred for 4 hours and treated with ice cold water (400 mL). The two layers were separated. The aqueous layer was acidified with 1N HCl and then extracted with ethyl acetate. The organic layers were combined, washed successively with water, saturated solution of NaHCO$_3$ and brine. The organic layer was dried over anhydrous Na$_2$SO$_4$; the solvent was removed under reduced pressure to obtain the title compound. $^1$H-NMR (400 MHz, CDCl$_3$): δ 12.49 (bs, 1H), 7.73 (s, 1H), 7.51 (d, J=7.7 Hz, 1H), 7.23 (d, J=7.2 Hz, 1H), 7.01 (t, J=7.3 Hz, 1H), 6.95 (d, J=7.6 Hz, 1H), 3.79 (s, 3H), 2.62 (bs, 1H); Mass (m/z): 287.1, 289.1 (M+H)$^+$.

Intermediate 26

Methyl 4-(2-fluorobenzyl)-4H-benzo[1,4]oxazine-2-carboxylate (I-26)

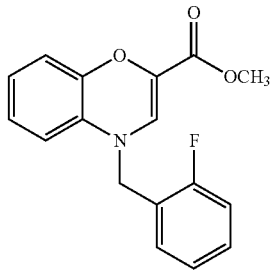 [SMILES: COC(=O)C1=CN(Cc2ccccc2F)c2ccccc2O1]

To a solution of the intermediate, I-19 (1.2 g, 4.4 mmol) in MeOH (18 mL) was added 2-fluorobenzylamine (0.55 g, 4.4 mmol) and stirred for 12 hours at ambient temperature. The volatiles were evaporated to dryness. The crude residue (1.79 g) was redissolved in DMF (4.4 mL) and CuI (175.6 mg, 0.92 mmol) and $Cs_2CO_3$ (3.1 g, 9.2 mmol) were added. The reaction mixture was allowed to stir vigorously at 85-90° C. for 6 hours. After completion of the reaction, the mixture was cooled to room temperature and diluted with water and the mixture was extracted with ethyl acetate. The combined organic extracts were washed with 10% solution of HCl, with brine and dried over anhydrous $Na_2SO_4$. The solvent was evaporated under reduced pressure to afford the title compound.

Yield: 1.48 g; $^1$H-NMR (400 MHz, $CDCl_3$): δ 7.46 (t, J=7.7 Hz, 1H), 7.40-7.25 (m, 1H), 7.20-7.0 (m, 3H), 6.70-6.60 (m, 2H), 6.58 (s, 1H), 6.24 (d, J=7.3 Hz, 1H), 4.45 (s, 2H), 3.75 (s, 3H); Mass (m/z): 300.2 (M+H)$^+$.

Using the above reaction procedure, the following intermediates, I-27 to I-31 were prepared by reacting the intermediates I-20 to I-24 with appropriate benzyl amines.

Intermediate 27

Methyl 8-fluoro-4-(2-fluorobenzyl)-4H-benzo[1,4]oxazine-2-carboxylate (I-27)

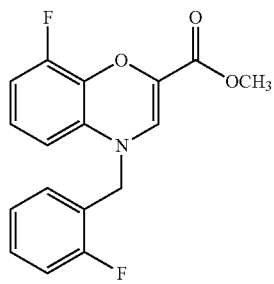 [SMILES: COC(=O)C1=CN(Cc2ccccc2F)c2cccc(F)c2O1]

$^1$H-NMR (400 MHz, $CDCl_3$): δ 7.45 (t, J=7.3 Hz, 1H), 7.36-7.27 (m, 1H), 7.16 (s, 1H), 7.09 (t, J=8.9 Hz, 1H), 6.60-6.50 (m, 3H), 6.04 (d, J=7.5 Hz, 1H), 4.45 (s, 2H), 3.77 (s, 3H); Mass (m/z): 318.2 (M+H)$^+$.

Intermediate 28

Methyl 1-benzyl-1H-pyrido[2,3-b][1,4]oxazine-3-carboxylate (I-28)

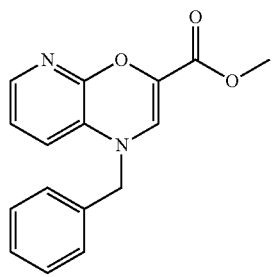 [SMILES: COC(=O)C1=CN(Cc2ccccc2)c2cccnc2O1]

$^1$H-NMR (400 MHz, $CDCl_3$): δ 7.54 (d, J=4.2 Hz, 1H), 7.40-7.27 (m, 5H), 6.73 (d, J=7.5 Hz, 1H), 6.60-6.50 (m, 2H), 4.64 (s, 2H), 3.72 (s, 3H); Mass (m/z): 283.2 (M+H)$^+$.

Intermediate 29

Methyl 4-(2-fluorobenzyl)-4H-pyrido[3,2-b][1,4]oxazine-2-carboxylate (I-29)

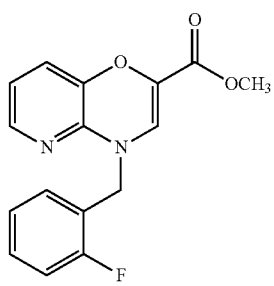 [SMILES: COC(=O)C1=CN(Cc2ccccc2F)c2ncccc2O1]

$^1$H-NMR (400 MHz, $CDCl_3$): δ 7.54 (d, J=4.9 Hz, 1H), 7.47 (t, J=7.5 Hz, 1H), 7.38 (t, J=7.0 Hz, 1H), 7.35-7.20 (m, 1H), 7.10-7.0 (m, 1H), 6.72 (d, J=7.4 Hz, 1H), 6.61 (s, 1H), 6.54 (dd, J=5.1, 7.5, Hz, 1H), 4.68 (s, 2H), 3.73 (s, 3H); Mass (m/z): 301.1 (M+H)$^+$.

Intermediate 30

Methyl 5-fluoro-4-(2-fluorobenzyl)-4H-benzo[1,4]oxazine-2-carboxylate (I-30)

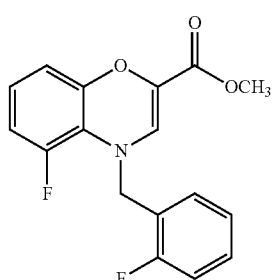

$^1$H-NMR (400 MHz, $CDCl_3$): δ 7.49 (t, J=7.3 Hz, 1H), 7.17 (t, J=6.0 Hz, 1H), 7.08 (t, J=9.4 Hz, 1H), 6.70-6.62 (m, 1H), 6.55-6.40 (m, 3H), 4.64 (s, 2H), 3.77 (s, 3H); Mass (m/z): 318.3 (M+H)$^+$.

Intermediate 31

Methyl 5,8-difluoro-4-(2-fluorobenzyl)-4H-benzo[1,4]oxazine-2-carboxylate (I-31)

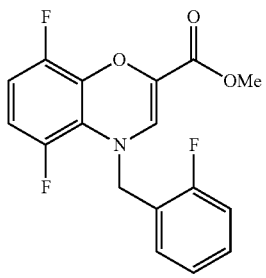 [SMILES: COC(=O)C1=CN(Cc2ccccc2F)c2c(F)ccc(F)c2O1]

¹H-NMR (400 MHz, CDCl₃): δ 7.47 (t, J=7.2 Hz, 1H), 7.36-7.29 (m, 1H), 7.15 (t, J=7.4 Hz, 1H), 7.09 (t, J=9.4 Hz, 1H), 6.56-6.38 (m, 3H), 4.64 (s, 2H), 3.76 (s, 3H); Mass (m/z): 336.2 (M+H)⁺.

Intermediate 32

Methyl 4-(2,3-difluorobenzyl)-4H-benzo[1,4]thiazine-2-carboxylate (I-32)

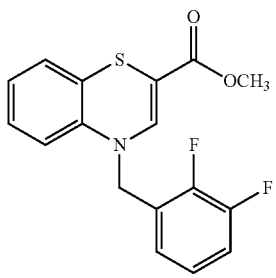 [SMILES: COC(=O)C1=CN(Cc2cccc(F)c2F)c2ccccc2S1]

To a solution of the intermediate, I-25 (0.8 g, 2.77 mmol) in MeOH (11 mL) was added 2,3-difluorobenzylamine, (I-1, 0.4 g, 2.77 mmol). The reaction mixture was stirred for 12 hours at ambient temperature. The volatiles were evaporated to dryness. The crude residue (1.21 g) was redissolved in DMF (5.4 mL) and to the solution CuI (55.6 mg, 0.29 mmol) and K₃PO₄ (1.24 g, 5.86 mmol) were added. The reaction mixture was allowed to stir vigorously at 100-110° C. for 16 hours. After completion of the reaction, the mixture was cooled to room temperature and diluted with water and the mixture was extracted with ethyl acetate. The combined organic extracts were washed with 10% solution of HCl, with brine and dried over anhydrous Na₂SO₄. The solvent was evaporated under reduced pressure and the crude thus obtained was purified by silica gel column chromatography to afford the title compound.

Yield: 0.55 g; ¹H-NMR (400 MHz, CDCl₃): δ 7.20 (t, J=5.9 Hz, 1H), 7.15 (s, 1H), 7.14-7.08 (m, 2H), 6.90-6.78 (m, 3H), 6.35 (d, J=7.5 Hz, 1H), 4.70 (s, 2H), 3.74 (s, 3H); Mass (m/z): 333.0 (M+H)⁺.

Intermediate 33

4-(2-Fluorobenzyl)-4H-benzo[1,4]oxazine-2-carboxylic acid (I-33)

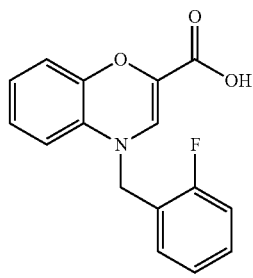 [SMILES: O=C(O)C1=CN(Cc2ccccc2F)c2ccccc2O1]

To a stirred solution of the intermediate, I-26 (1.45 g, 4.86 mmol) in a 1:1 mixture of methanol and water (24 mL), NaOH (0.39 g, 9.7 mmol) was added. The reaction mixture was refluxed (85-90° C.) for 4 hours. After cooling the reaction mass to RT the volatiles were evaporated to one half of its volume under reduced pressure. The obtained reaction mass was washed once with ether, cooled to 5° C., acidified with 1N HCl and extracted with dichloromethane. The combined organic layer was dried over anhydrous Na₂SO₄ and the solvent was evaporated under reduced pressure to obtain the title compound.

Yield: 0.4 g; ¹H-NMR (400 MHz, DMSO-d₆): δ 12.1 (bs, 1H), 7.50 (t, J=7.8 Hz, 1H), 7.36 (dd, J=6.7, 13.8 Hz, 1H), 7.25 (d, J=9.7 Hz, 1H), 7.21 (d, J=6.8 Hz, 1H), 6.88 (s, 1H), 6.70-6.62 (m, 2H), 6.50-6.42 (m, 1H), 6.42-6.36 (m, 1H), 4.61 (s, 2H); Mass (m/z): 286.2 (M+H)⁺.

Using the above reaction procedure, the following intermediates, I-34 to I-38 were prepared by using the intermediates, I-27 to I-31.

Intermediate 34

8-Fluoro-4-(2-fluorobenzyl)-4H-benzo[1,4]oxazine-2-carboxylic acid (I-34)

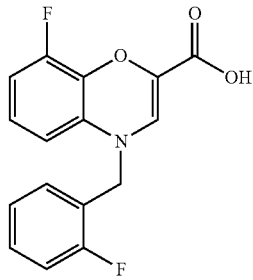 [SMILES: O=C(O)C1=CN(Cc2ccccc2F)c2cccc(F)c2O1]

¹H-NMR (400 MHz, DMSO-d₆): δ 12.33 (bs, 1H), 7.53 (t, J=7.6 Hz, 1H), 7.42-7.33 (m, 1H), 7.30-7.20 (m, 2H), 6.92 (s, 1H), 6.70-6.62 (m, 2H), 6.28-6.22 (m, 1H), 4.64 (s, 2H); Mass (m/z): 304.2 (M+H)⁺.

Intermediate 35

1-Benzyl-1H-pyrido[2,3-b][1,4]oxazine-3-carboxylic acid (I-35)

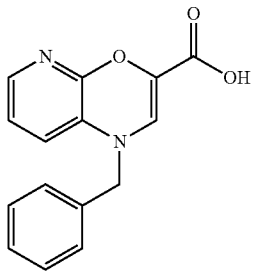 [SMILES: O=C(O)C1=CN(Cc2ccccc2)c2cccnc2O1]

¹H-NMR (400 MHz, DMSO-d₆): δ 12.33 (bs, 1H), 7.52 (t, J=4.2 Hz, 1H), 7.42-7.30 (m, 4H), 7.28 (t, J=6.7 Hz, 1H), 6.89 (s, 1H), 6.78 (d, J=7.0 Hz, 1H), 6.64 (dd, J=5.0, 7.7 Hz, 1H), 4.66 (s, 2H); Mass (m/z): 269.2 (M+H)⁺.

Intermediate 36

4-(2-Fluorobenzyl)-4H-pyrido[3,2-b][1,4]oxazine-2-carboxylic acid (I-36)

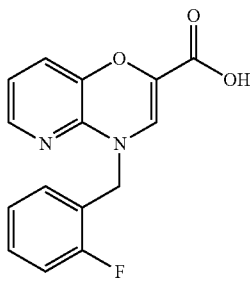 [SMILES: O=C(O)C1=CN(Cc2ccccc2F)c2ncccc2O1]

¹H-NMR (400 MHz, DMSO-d₆): δ 7.55 (d, J=5.2 Hz, 1H), 7.49 (t, J=7.4 Hz, 1H), 7.34-7.26 (m, 1H), 7.18-7.03 (m, 2H), 6.75 (s, 1H), 6.71 (d, J=8.2 Hz, 1H), 6.58 (dd, J=5.1, 7.6 Hz, 1H), 4.70 (s, 2H); Mass (m/z): 287.2 (M+H)⁺.

Intermediate 37

5-Fluoro-4-(2-fluorobenzyl)-4H-benzo[1,4]oxazine-2-carboxylic acid (I-37)

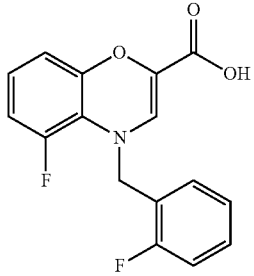 [SMILES: O=C(O)C1=CN(Cc2ccccc2F)c2c(F)cccc2O1]

¹H-NMR (400 MHz, DMSO-d₆): δ 12.42 (bs, 1H), 7.53 (t, J=7.4 Hz, 1H), 7.42-7.32 (m, 1H), 7.28-7.20 (m, 2H), 6.82 (s, 1H), 6.80-6.70 (m, 1H), 6.68-6.58 (m, 1H), 6.38 (d, J=7.9 Hz, 1H), 4.72 (s, 2H); Mass (m/z): 304.3 (M+H)⁺.

Intermediate 38

5,8-Difluoro-4-(2-fluorobenzyl)-4H-benzo[1,4]oxazine-2-carboxylic acid (I-38)

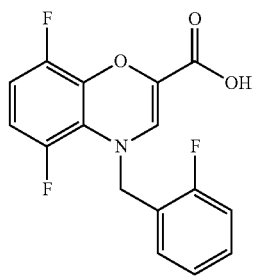 [SMILES: O=C(O)C1=CN(Cc2ccccc2F)c2c(F)ccc(F)c2O1]

¹H-NMR (400 MHz, DMSO-d₆): δ 12.45 (bs, 1H), 7.54 (t, J=7.2 Hz, 1H), 7.40-7.30 (m, 1H), 7.28-7.18 (m, 2H), 6.87 (s, 1H), 6.82-6.72 (m, 1H), 6.72-6.62 (m, 1H), 4.74 (s, 2H); Mass (m/z): 322.1 (M+H)⁺.

Intermediate 39

4-(2,3-Difluorobenzyl)-4H-benzo[1,4]thiazine-2-carboxylic acid (I-39)

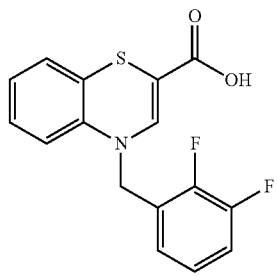 [SMILES: O=C(O)C1=CN(Cc2cccc(F)c2F)c2ccccc2S1]

To a stirred solution of the intermediate, I-32 (0.23 g, 0.69 mmol) in a 1:1 mixture of methanol and water (2.8 mL), NaOH (55.2 mg, 1.4 mmol) was added. The reaction mixture was refluxed (85-90° C.) for 6 hours. After cooling the reaction mass to RT, the volatiles were evaporated to one half of its volume under reduced pressure. The reaction mass obtained was washed with ether, cooled to 0-5° C., acidified with 1N HCl and extracted with dichloromethane. The combined organic layer was dried over anhydrous Na₂SO₄ and the solvent was evaporated under reduced pressure to obtain the title compound.

Yield: 0.21 g; ¹H-NMR (400 MHz, DMSO-d₆): δ 12.36 (bs, 1H), 7.50-7.40 (m, 1H), 7.28 (s, 1H), 7.27-7.20 (m, 2H), 7.40-7.30 (m, 1H), 7.30-7.25 (m, 2H), 6.54 (d, J=8.0 Hz, 1H), 4.87 (s, 2H); Mass (m/z): 318.3 (M−H)⁺.

Example 1

N-(cis-1S, 2S-2-Hydroxycyclohexyl)-4-(2-fluorobenzyl)-4H-benzo[1,4]oxazine-2-carboxamide

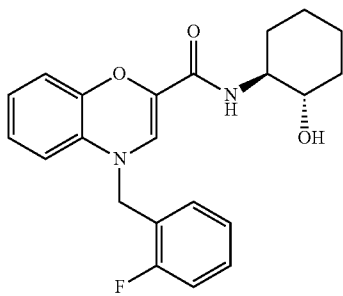 [SMILES: O=C(N[C@H]1CCCC[C@@H]1O)C1=CN(Cc2ccccc2F)c2ccccc2O1]

To a solution of the intermediate, I-33 (100.8 mg, 0.35 mmol) in dichloromethane (2.0 mL) at RT, DIPEA (0.15 mL, 0.88 mmol), HATU (0.15 g, 0.39 mmol) and (1S,2S) 2-aminocyclohexanol hydrochloride (53.5 mg, 0.35 mmol) was added sequentially while stirring vigorously. After completion of addition, the reaction mixture was stirred for 16 hours before diluted with dichloromethane. The reaction mass was washed with water, brine, dried over anhydrous $Na_2SO_4$ and the solvent was evaporated under vacuum. The crude mass obtained was purified on silica gel column to afford the title compound.

Yield: 106.4 mg; $^1$H-NMR (400 MHz, $CDCl_3$): δ 7.46 (t, J=7.4 Hz, 1H), 7.29 (t, J=6.2 Hz, 1H), 7.17-7.05 (m, 2H), 6.72-6.62 (m, 2H), 6.57 (s, 1H), 6.56-6.49 (m, 1H), 6.30-6.23 (m, 1H), 5.99 (d, J=6.7 Hz, 1H), 4.46 (s, 2H), 3.83 (t, J=3.7 Hz, 1H), 3.76-3.65 (m, 1H), 3.45-3.36 (m, 1H), 2.15-2.06 (m, 1H), 2.05-1.95 (m, 1H), 1.82-1.70 (m, 2H), 1.42-1.18 (m, 4H); Mass (m/z): 383.4 (M+H)⁺.

Examples 2 to 72

The compounds of Examples 2 to 72 were prepared by following the experimental procedures as described in the Example 1 given above, with some non-critical variations using appropriate acids, for example I-33 to I-38 with suitable $R^1NH_2$.

| Example Number | Chemical name and Structure | Characterization data |
|---|---|---|
| 2 | N-(cis-1S,2S-2-Hydroxycyclohexyl)-4-(2-fluorobenzyl)-8-fluoro-4H-benzo[1,4]oxazine-2-carboxamide | $^1$H-NMR (400 MHz, $CDCl_3$): δ 7.44 (t, J = 7.3 Hz, 1H), 7.33-7.25 (m, 2H), 7.14 (t, J = 7.4 Hz, 1H), 7.08 (t, J = 8.9 Hz, 1H), 6.63-6.48 (m, 3H), 6.08-6.02 (m, 1H), 4.46 (s, 2H), 3.78-3.64 (m, 2H), 3.46-3.36 (m, 1H), 2.15-2.07 (m, 1H), 2.02-1.94 (m, 1H), 1.80-1.72 (m, 2H), 1.42-1.20 (m, 4H); Mass (m/z): 401.3 (M + H)⁺. |
| 3 | N-(cis-1S,2S-2-Hydroxycyclohexyl)-4-{2-fluorobenzyl}-4H-pyrido[3,2-b][1,4]oxazine-2-carboxamide | $^1$H-NMR (400 MHz, $CDCl_3$): δ 7.58 (d, J = 4.9 Hz, 1H), 7.45 (t, J = 7.3 Hz, 1H), 7.12-7.03 (m, 3H), 6.64 (d, J = 7.7 Hz, 1H), 6.54 (t, J = 7.4 Hz, 2H), 5.93 (d, J = 6.7 Hz, 1H), 4.69 (s, 2H), 3.70-3.67 (m, 1H), 3.66-3.65 (m, 1H), 3.38-3.37 (m, 1H), 2.09 (m, 1H), 1.97-1.94 (m, 1H), 1.74-1.71 (m, 2H), 1.38-1.21 (m, 4H); Mass (m/z): 384.3 (M + H)⁺. |

| Example Number | Chemical name and Structure | Characterization data |
|---|---|---|
| 4 | N-(cis-1S,2S-2-Hydroxycyclohexyl)-4-benzyl-4H-benzo[1,4]oxazine-2-carboxamide 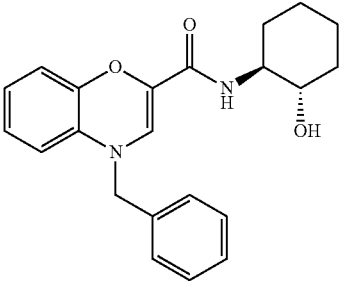 | $^1$H-NMR (400 MHz, CDCl$_3$): δ 7.40-7.32 (m, 4H), 7.32-7.28 (m, 1H), 6.70-6.58 (m, 2H), 6.58 (s, 1H), 6.52-6.48 (m, 1H), 6.23 (d, J = 6.7 Hz, 1H), 6.0 (d, J = 6.6 Hz, 1H), 4.41 (s, 2H), 3.89 (d, J = 3.5 Hz, 1H), 3.77-3.65 (m, 1H), 3.45-3.33 (m, 1H), 2.15-2.06 (m, 1H), 2.05-1.95 (m, 1H), 1.80-1.70 (m, 2H), 1.40-1.20 (m, 4H); Mass (m/z): 365.2 (M + H)$^+$. |
| 5 | N-(cis-1S,2S-2-Hydroxycyclohexyl)-4-(4-methoxybenzyl)-4H-benzo[1,4]oxazine-2-carboxamide 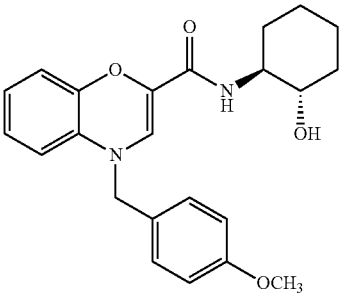 | $^1$H-NMR (400 MHz, CDCl$_3$): δ 7.28 (d, J = 8.0 Hz, 2H), 6.89 (d, J = 8.0 Hz, 2H), 6.68-6.61 (m, 2H), 6.56 (s, 1H), 6.53-6.48 (m, 1H), 6.30-6.24 (m, 1H), 5.98 (d, J = 6.5 Hz, 1H), 4.34 (s, 2H), 3.90 (bs, 1H), 3.79 (s, 3H), 3.75-3.62 (m, 1H), 3.43-3.36 (m, 1H), 2.15-2.06 (m, 1H), 2.05-1.95 (m, 1H), 1.80-1.70 (m, 2H), 1.42-1.18 (m, 4H); Mass (m/z): 395.1 (M + H)$^+$. |
| 6 | N-(2-Hydroxy-2-methylpropyl)-4-(4-methoxybenzyl)-4H-benzo[1,4]oxazine-2-carboxamide 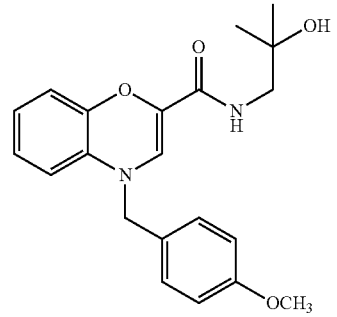 | $^1$H-NMR (400 MHz, CDCl$_3$): δ 7.28 (d, J = 8.4 Hz, 2H), 6.89 (d, J = 8.4 Hz, 2H), 6.68-6.62 (m, 2H), 6.55 (s, 1H), 6.54-6.49 (m, 1H), 6.49-6.42 (m, 1H), 6.30-6.23 (m, 1H), 4.34 (s, 2H), 3.79 (s, 3H), 3.35 (d, J = 6.1 Hz, 2H), 1.25 (s, 6H); Mass (m/z): 369.3 (M + H)$^+$. |

| Example Number | Chemical name and Structure | Characterization data |
|---|---|---|
| 7 | N-(cis-1S,2S-2-Hydroxycyclohexyl)-4-(3-fluorobenzyl)-4H-benzo[1,4]oxazine-2-carboxamide 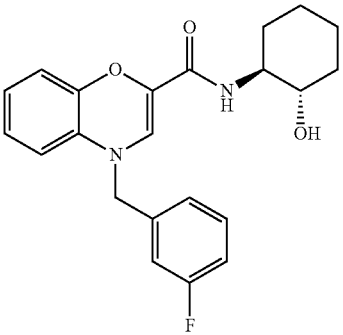 | $^1$H-NMR (400 MHz, CDCl$_3$): δ 7.48-7.30 (m, 1H), 7.15 (d, J = 7.4 Hz, 1H), 7.08 (d, J = 9.4 Hz, 1H), 6.98 (t, J = 8.2 Hz, 1H), 6.70-6.60 (m, 2H), 6.58-6.51 (m, 2H), 6.18 (d, J = 7.1 Hz, 1H), 6.01 (d, J = 6.4 Hz, 1H), 4.40 (s, 2H), 3.80 (bs, 1H), 3.78-3.66 (m, 1H), 3.47-3.35 (m, 1H), 2.15-2.05 (m, 1H), 2.05-1.95 (m, 1H), 1.80-1.70 (m, 2H), 1.43-1.18 (m, 4H); Mass (m/z): 383.4 (M + H)$^+$. |
| 8 | N-(2-Hydroxy-2-methylpropyl)-4-(3-fluorobenzyl)-4H-benzo[1,4]oxazine-2-carboxamide 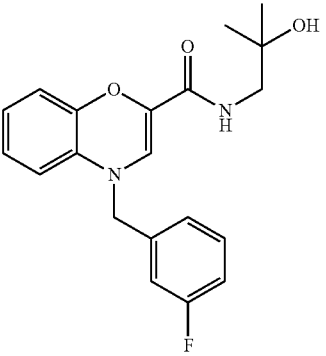 | $^1$H-NMR (400 MHz, CDCl$_3$): δ 7.38-7.28 (m, 1H), 7.15 (d, J = 7.3 Hz, 1H), 7.09 (d, J = 9.4 Hz, 1H), 6.98 (t, J = 8.1 Hz, 1H), 6.70-6.60 (m, 2H), 6.58-6.43 (m, 3H), 6.18 (d, J = 7.2 Hz, 1H), 4.40 (s, 2H), 3.36 d, (d, 6.1 Hz, 2H), 1.26 (s, 6H); Mass (m/z): 357.3 (M + H)$^+$. |
| 9 | N-(cis-1S,2S-2-Hydroxycyclohexyl)-4-(3-methoxybenzyl)-4H-benzo[1,4]oxazine-2-carboxamide 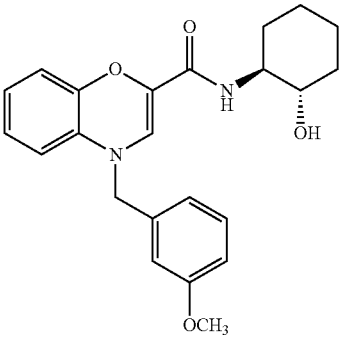 | $^1$H-NMR (400 MHz, CDCl$_3$): δ 7.32-7.26 (m, 1H), 6.96 (d, J = 7.6 Hz, 1H), 6.88 (s, 1H), 6.83 (d, J = 8.1 Hz, 1H), 6.68-6.60 (m, 2H), 6.57 (s, 1H), 6.52-6.48 (m, 1H), 6.76-6.72 (m, 1H), 5.99 (d, J = 6.9 Hz, 1H), 4.38 (s, 2H), 3.89 (d, J = 3.7 Hz, 1H), 3.79 (s, 3H), 3.76-3.65 (m, 1H), 3.46-3.37 (m, 1H), 2.15-2.06 (m, 1H), 2.05-1.95 (m, 1H), 1.81-1.72 (m, 2H), 1.41-1.20 (m, 4H); Mass (m/z): 395.2 (M + H)$^+$. |

| Example Number | Chemical name and Structure | Characterization data |
| --- | --- | --- |
| 10 | N-(2-Hydroxy-2-methylpropyl)-4-(3-methoxybenzyl)-4H-benzo[1,4]oxazine-2-carboxamide | $^1$H-NMR (400 MHz, CDCl$_3$): δ 7.32-7.25 (m, 1H), 6.96 (d, J = 7.5 Hz, 1H), 6.89 (s, 1H), 6.82 (d, J = 8.1 Hz, 1H), 6.68-6.60 (m, 2H), 6.55 (s, 1H), 6.55-6.50 (m, 1H), 6.50-6.43 (m, 1H), 6.26-6.21 (m, 1H), 4.37 (s, 2H), 3.80 (s, 3H), 3.35 (d, J = 6.1 Hz, 2H), 1.25 (s, 6H); Mass (m/z): 369.1 (M + H)$^+$. |
| 11 | N-(cis-1S,2S-2-Hydroxycyclohexyl)-4-(2-methoxypyridin-4-ylmethyl)-4H-benzo[1,4]oxazine-2-carboxamide | $^1$H-NMR (400 MHz, CDCl$_3$): δ 8.14 (d, J = 5.3 Hz, 1H), 6.88 (d, J = 5.3 Hz, 1H), 6.76 (s, 1H), 6.72-6.62 (m, 2H), 6.58-6.52 (m, 2H), 6.12 (d, J = 7.3 Hz, 1H), 6.01 (d, J = 7.0 Hz, 1H), 4.34 (s, 2H), 3.91 (s, 3H), 3.74 (bs, 1H), 3.74-3.65 (m, 1H), 3.58-3.48 (m, 1H), 2.18-2.08 (m, 1H), 2.05-1.95 (m, 1H), 1.80-1.70 (m, 2H), 1.42-1.20 (m, 4H); Mass (m/z): 396.1 (M + H)$^+$. |
| 12 | N-(2-Hydroxy-2-methylpropyl)-4-(2-methoxypyridin-4-ylmethyl)-4H-benzo[1,4]oxazine-2-carboxamide | $^1$H-NMR (400 MHz, CDCl$_3$): δ 8.14 (d, J = 5.2 Hz, 1H), 6.88 (d, J = 5.2 Hz, 1H), 6.77 (s, 1H), 6.72-6.60 (m, 2H), 6.58-6.43 (m, 3H), 6.12 (d, J = 7.4 Hz, 1H), 4.35 (s, 2H), 3.93 (s, 3H), 3.36 (d, J = 6.2 Hz, 2H), 2.68 (s, 1H), 1.26 (s, 6H); Mass (m/z): 370.3 (M + H)$^+$. |

| Example Number | Chemical name and Structure | Characterization data |
|---|---|---|
| 13 | N-(cis-1S,2S-2-Hydroxycyclohexyl)-4-(4-fluorobenzyl)-4H-benzo[1,4]oxazine-2-carboxamide 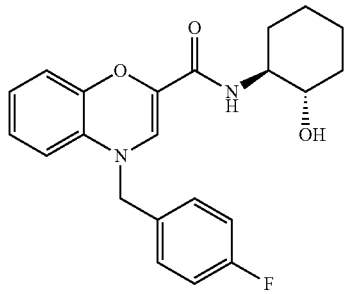 | $^1$H-NMR (400 MHz, CDCl$_3$): δ 7.38-7.32 (m, 2H), 7.04 (t, J = 8.5 Hz, 2H), 6.70-6.62 (m, 2H), 6.55 (s, 1H), 6.55-6.50 (m, 1H), 6.21 (d, J = 6.7 Hz, 1H), 5.99 (d, J = 6.8 Hz, 1H), 4.38 (s, 2H), 3.80 (d, J = 3.5 Hz, 1H), 3.78-3.65 (m, 1H), 3.45-3.34 (m, 1H), 2.15-2.05 (m, 1H), 2.05-1.96 (m, 1H), 1.80-1.70 (m, 2H), 1.43-1.18 (m, 4H); Mass (m/z): 383.4 (M + H)$^+$. |
| 14 | N-(2-Hydroxy-2-methylpropyl)-4-(4-fluorobenzyl)-4H-benzo[1,4]oxazine-2-carboxamide 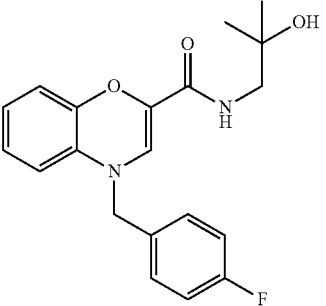 | $^1$H-NMR (400 MHz, CDCl$_3$): δ 7.33 (t, J = 7.6 Hz, 2H), 7.04 (t, J = 8.4 Hz, 2H), 6.70-6.50 (m, 2H), 6.60-6.38 (m, 3H), 6.19 (d, J = 6.8 Hz, 1H), 4.38 (s, 2H), 3.36 (d, J = 6.1 Hz, 1H), 2.75 (bs, 1H), 1.26 (s, 6H); Mass (m/z): 357.3 (M + H)$^+$. |
| 15 | N-(cis-1S,2S-2-Hydroxycyclohexyl)-4-(2-methoxypyridin-5-ylmethyl)-4H-benzo[1,4]oxazine-2-carboxamide 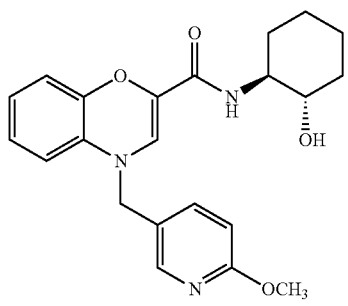 | $^1$H-NMR (400 MHz, CDCl$_3$): δ 8.18 (s, 1H), 7.64 (d, J = 8.5 Hz, 1H), 6.78 (d, J = 8.5 Hz, 1H), 6.74-6.66 (m, 2H), 6.57 (s, 1H), 6.56-6.52 (m, 1H), 6.36-6.30 (m, 1H), 6.01 (d, J = 6.8 Hz, 1H), 4.36 (s, 2H), 3.94 (s, 3H), 3.81 (bs, 1H), 3.80-3.68 (m, 1H), 3.48-3.38 (m, 1H), 2.18-2.10 (m, 1H), 2.08-1.98 (m, 1H), 1.83-1.73 (m, 2H), 1.41-1.20 (m, 4H); Mass (m/z): 396.1 (M + H)$^+$. |

| Example Number | Chemical name and Structure | Characterization data |
|---|---|---|
| 16 | N-(2-Hydroxy-2-methylpropyl)-4-(2-methoxypyridin-5-ylmethyl)-4H-benzo[1,4]oxazine-2-carboxamide | $^1$H-NMR (400 MHz, CDCl$_3$): δ 8.18 (s, 1H), 7.64 (d, J = 8.4 Hz, 1H), 6.78 (d, J = 8.4 Hz, 1H), 6.74-6.66 (m, 2H), 6.55 (s, 1H), 6.55-5.45 (m, 2H), 6.34-6.26 (m, 1H), 4.36 (s, 3H), 3.94 (s, 3H), 3.37 (d, J = 6.1 Hz, 1H), 2.76 (bs, 1H), 1.27 (m, 6H); Mass (m/z): 370.3 (M + H)$^+$. |
| 17 | N-(cis-1S,2S-2-Hydroxycyclohexyl)-4-(3-trifluoromethylbenzyl)-4H-benzo[1,4]oxazine-2-carboxamide | $^1$H-NMR (400 MHz, CDCl$_3$): δ 7.66-7.58 (m, 2H), 7.51 (t, J = 7.5 Hz, 1H), 6.76-6.62 (m, 2H), 6.62-6.53 (m, 2H), 6.18 (d, J = 6.7 Hz, 1H), 6.04 (d, J = 6.8 Hz, 1H), 4.48 (s, 2H), 3.77 (d, J = 3.2 Hz, 1H), 3.76-3.66 (m, 1H), 3.48-3.38 (m, 1H), 2.18-2.09 (m, 1H), 2.09-1.98 (m, 1H), 1.83-1.73 (m, 2H), 1.40-1.20 (m, 4H); Mass (m/z): 433.1 (M + H)$^+$. |
| 18 | N-(cis-1S,2S-2-Hydroxycyclohexyl)-4-(2,3-difluorobenzyl)-4H-benzo[1,4]oxazine-2-carboxamide | $^1$H-NMR (400 MHz, CDCl$_3$): δ 7.23 (t, J = 7.7 Hz, 1H), 7.16-7.03 (m, 2H), 6.72-6.63 (m, 2H), 6.55 (s, 1H), 6.55-6.50 (m, 1H), 6.26-6.18 (m, 1H), 6.01 (d, J = 6.9 Hz, 1H), 4.48 (s, 2H), 3.76 (bs, 1H), 3.75-3.64 (m, 1H), 3.43-3.36 (m, 1H), 2.15-2.06 (m, 1H), 2.05-1.96 (m, 1H), 1.80-1.70 (m, 2H), 1.40-1.20 (m, 4H); Mass (m/z): 401.3 (M + H)$^+$. |

| Example Number | Chemical name and Structure | Characterization data |
| --- | --- | --- |
| 19 | N-(cis-1S,2S-2-Hydroxycyclohexyl)-4-(3,4-difluorobenzyl)-4H-benzo[1,4]oxazine-2-carboxamide | $^1$H-NMR (400 MHz, CDCl$_3$): δ 7.25-7.08 (m, 3H), 6.72-6.62 (m, 2H), 6.58-6.52 (m, 2H), 6.16 (dd, J = 1.6, 7.2 Hz, 1H), 6.01 (d, J = 6.8 Hz, 1H), 4.36 (s, 2H), 3.73 (bs, 1H), 3.72-3.65 (m, 1H), 3.48-3.39 (m, 1H), 2.15-2.08 (m, 1H), 2.05-1.95 (m, 1H), 1.81-1.70 (m, 2H), 1.40-1.20 (m, 4H); Mass (m/z): 401.3 (M + H)$^+$. |
| 20 | N-(3-Hydroxytetrahydropyran-4-yl)-4-(2,3-difluorobenzyl)-4H-benzo[1,4]oxazine-2-carboxamide | $^1$H-NMR (400 MHz, CDCl$_3$): δ 7.23 (t, J = 6.0 Hz, 1H), 7.18-7.05 (m, 2H), 6.73-6.64 (m, 2H), 6.59 (s, 1H), 6.58-6.50 (m, 1H), 6.28-6.22 (m, 1H), 6.06 (d, J = 6.0 Hz, 1H), 4.55 (d, J = 2.5 Hz, 1H), 4.49 (s, 2H), 4.07 (dd, J = 5.0, 11.3 Hz, 1H), 3.99 (dd, J = 4.3, 11.6 Hz, 1H), 3.90-3.78 (m, 1H), 3.60-3.50 (m, 1H), 3.45 (dt, J = 1.7, 11.6 Hz, 1H), 3.16 (t, J = 10.7 Hz, 1H), 2.0-1.92 (m, 1H), 1.80-1.65 (m, 1H); Mass (m/z): 403.3 (M + H)$^+$. |
| 21 | N-(cis-1S,2S-2-Hydroxycyclohexyl)-4-(2-chloropyridin-5-ylmethyl)-4H-benzo[1,4]oxazine-2-carboxamide | $^1$H-NMR (400 MHz, CDCl$_3$): δ 8.39 (bs, 1H), 7.72 (d, J = 8.0 Hz, 1H), 7.34 (d, J = 8.2 Hz, 1H), 6.75-6.63 (m, 2H), 6.60-6.50 (m, 2H), 6.16 (d, J = 7.2 Hz, 1H), 6.03 (d, J = 6.7 Hz, 1H), 4.41 (s, 2H), 3.80-3.65 (m, 2H), 3.46-3.38 (m, 1H), 2.15-2.05 (m, 1H), 2.04-1.95 (m, 1H), 1.82-1.70 (m, 2H), 1.40-1.20 (m, 4H); Mass (m/z): 400.3, 402.3 (M + H)$^+$. |

| Example Number | Chemical name and Structure | Characterization data |
|---|---|---|
| 22 | N-(cis-1S,2S-2-Hydroxycyclohexyl)-4-(pyridin-3-ylmethyl)-4H-benzo[1,4]oxazine-2-carboxamide | $^1$H-NMR (400 MHz, CDCl$_3$): δ 8.62 (bs, 1H), 8.55 (bs, 1H), 7.80-7.75 (m, 1H), 7.38-7.30 (m, 1H), 6.70-6.60 (m, 2H), 6.56 (s, 1H), 6.56-6.50 (m, 1H), 6.21-6.18 (m, 1H), 6.07-6.0 (m, 1H), 4.44 (s, 2H), 3.78-3.65 (m, 1H), 3.45-3.35 (m, 1H), 2.99 (bs, 1H), 2.18-1.95 (m, 2H), 1.82-1.70 (m, 2H), 1.40-1.20 (m, 4H); Mass (m/z): 366.4 (M + H)$^+$. |
| 23 | N-(cis-1S,2S-2-Hydroxycyclohexyl)-4-(pyridin-4-ylmethyl)-4H-benzo[1,4]oxazine-2-carboxamide | $^1$H-NMR (400 MHz, CDCl$_3$): δ 8.59 (bs, 2H), 7.3 (bs, 2H), 6.75-6.60 (m, 2H), 6.59-6.52 (m, 2H), 6.15-6.0 (m, 2H), 4.14 (s, 2H), 3.78-3.65 (m, 1H), 3.47-3.37 (m, 1H), 3.05 (bs, 1H), 2.15-1.98 (m, 2H), 1.82-1.70 (m, 2H), 1.40-1.20 (m, 4H); Mass (m/z): 366.4 (M + H)$^+$. |
| 24 | N-(cis-1S,2S-2-Hydroxycyclohexyl)-4-(2-chloropyridin-4-ylmethyl)-4H-benzo[1,4]oxazine-2-carboxamide | $^1$H-NMR (400 MHz, CDCl$_3$): δ 8.38 (d, J = 5.0 Hz, 1H), 7.34 (s, 1H), 7.30-7.25 (m, 1H), 6.76-6.62 (m, 2H), 6.57 (d, J = 7.4 Hz, 1H), 6.52 (s, 1H), 6.10-6.0 (m, 2H), 4.39 (s, 2H), 3.80-3.70 (m, 1H), 3.60 (bs, 1H), 3.48-3.36 (m, 1H), 2.16-2.06 (m, 1H), 2.05-1.96 (m, 1H), 3.80-3.70 (m, 2H), 1.41-1.20 (m, 4H); Mass (m/z): 400.2, 402.2 (M + H)$^+$. |

| Example Number | Chemical name and Structure | Characterization data |
|---|---|---|
| 25 | N-(cis-1S,2S-2-Hydroxycyclohexyl)-4-(pyridin-2-ylmethyl)-4H-benzo[1,4]oxazine-2-carboxamide | $^1$H-NMR (400 MHz, CDCl$_3$): δ 8.59 (d, J = 4.4 Hz, 1H), 7.68 (t, J = 8.0 Hz, 1H), 7.48 (d, J = 7.7 Hz, 1H), 7.21 (t, J = 5.5 Hz, 1H), 6.72-6.60 (m, 3H), 6.53 (d, J = 7.2 Hz, 1H), 6.02 (d, J = 6.8 Hz, 1H), 5.46 (d, J = 9.1 Hz, 1H), 4.52 (s, 2H), 3.85 (bs, 1H), 3.78-3.68 (m, 1H), 3.60-3.50 (m, 1H), 2.15-1.94 (m, 2H), 1.80-1.70 (m, 2H), 1.40-1.20 (m, 4H); Mass (m/z): 366.4 (M + H)$^+$. |
| 26 | N-(cis-1S,2S-2-Hydroxycyclohexyl)-4-(3,4-dichlorobenzyl)-4H-benzo[1,4]oxazine-2-carboxamide | $^1$H-NMR (400 MHz, CDCl$_3$): δ 7.48-7.42 (m, 2H), 7.25-7.20 (m, 1H), 6.74-6.61 (m, 2H), 6.58-6.52 (m, 2H), 6.14 (d, J = 6.9 Hz, 1H), 6.01 (d, J = 6.5 Hz, 1H), 4.36 (s, 2H), 3.80-3.65 (m, 2H), 3.45-3.36 (m, 1H), 2.15-2.07 (m, 1H), 2.07-1.96 (m, 1H), 1.84-1.70 (m, 2H), 1.42-1.20 (m, 4H); Mass (m/z): 433.2, 435.2 (M + H)$^+$. |
| 27 | N-(cis-1S,2S-2-Hydroxycyclohexyl)-4-(2-methyl pyridin-3-ylmethyl)-4H-benzo[1,4]oxazine-2-carboxamide | $^1$H-NMR (400 MHz, CDCl$_3$): δ 7.56 (t, J = 7.6 Hz, 1H), 7.10-6.95 (m, 2H), 6.70-6.50 (m, 4H), 6.22 (d, J = 6.6 Hz, 1H), 6.01 (d, J = 6.2 Hz, 1H), 4.48 (s, 2H), 3.78-3.58 (m, 2H), 3.45-3.35, (m, 1H), 2.55 (s, 3H), 2.15-1.94 (m, 1H), 1.80-1.70 (m, 2H), 1.40-1.20 (m, 4H); Mass (m/z): 380.4 (M + H)$^+$. |

-continued

| Example Number | Chemical name and Structure | Characterization data |
|---|---|---|
| 28 | N-(cis-1S,2S-2-Hydroxycyclohexyl)-4-(2,4-dichlorobenzyl)-4H-benzo[1,4]oxazine-2-carboxamide | $^1$H-NMR (400 MHz, CDCl$_3$): δ 7.48-7.43 (m, 2H), 7.30-7.23 (m, 1H), 6.73-6.62 (m, 2H), 6.58-6.52 (m, 2H), 6.09 (d, 7.3 Hz, 1H), 6.02 (d, J = 7.0 Hz, 1H), 4.45 (s, 2H), 3.76-3.66 (m, 2H), 3.43-3.35 (m, 1H), 2.15-1.95 (m, 2H), 1.80-1.70 (m, 2H), 1.40-1.20 (m, 4H); Mass (m/z): 433.3, 435.3 (M + H)$^+$. |
| 29 | N-(cis-1S,2S-2-Hydroxycyclohexyl)-4-(2,3-difluorobenzyl)-8-fluoro-4H-benzo[1,4]oxazine-2-carboxamide | $^1$H-NMR (400 MHz, CDCl$_3$): δ 7.21 (t, J = 7.4 Hz, 1H), 7.18-7.05 (m, 2H), 6.65-6.50 (m, 3H), 6.08-6.0 (m, 2H), 4.48 (s, 2H), 4.30-4.20 (m, 1H), 3.61 (d, J = 3.6 Hz, 1H), 3.48-3.40 (m, 1H), 2.20-2.10 (m, 1H), 2.08-1.98 (m, 1H), 1.80-1.70 (m, 2H), 1.43-1.22 (m, 4H); Mass (m/z): 419.2 (M + H)$^+$. |
| 30 | N-(cis-1S,2S-2-Hydroxycyclohexyl)-4-benzyl-4H-pyrido[3,2-b][1,4]oxazine-2-carboxamide | $^1$H-NMR (400 MHz, CDCl$_3$): δ 7.58 (d, J = 4.8 Hz, 1H), 7.40-7.35 (m, 4H), 6.64 (d, J = 7.6 Hz, 1H), 7.29 (t, J = 8.6 Hz, 1H), 5.59 (d, J = 6.6 Hz, 1H), 6.53 (t, J = 5.4 Hz, 1H), 6.52 (s, 1H), 4.64 (s, 1H), 3.66-3.64 (m, 2H), 3.38-3.36 (m, 1H), 2.08 (d, 1H), 1.96-1.94 (m, 1H), 1.74-1.71 (m, 2H), 1.38-1.21 (m, 4H); Mass (m/z): 366.2 (M + H)$^+$. |

-continued

| Example Number | Chemical name and Structure | Characterization data |
|---|---|---|
| 31 | N-(cis-1S,2S-2-Hydroxycyclohexyl)-1-benzyl-1H-pyrido[2,3-b][1,4]oxazine-3-carboxamide | $^1$H-NMR (400 MHz, CDCl$_3$): δ 7.58 (d, J = 4.8 Hz, 1H), 7.40-7.35 (m, 4H), 6.64 (d, J = 7.6 Hz, 1H), 7.29 (t, J = 8.6 Hz, 1H), 5.59 (d, J = 6.6 Hz, 1H), 6.53 (t, J = 5.4 Hz, 1H), 6.52 (s, 1H), 4.64 (s, 2H), 3.66-3.64 (m, 2H), 3.38-3.36 (m, 1H), 2.08 (d, 1H), 1.96-1.94 (m, 1H), 1.74-1.71 (m, 2H), 1.38-1.21 (m, 4H); Mass (m/z): 419.2 (M + H)$^+$. |
| 32 | N-(cis-1S,2S-2-Hydroxycyclohexyl)-1-{2,3-difluorobenzyl}-1H-pyrido[2,3-b][1,4]oxazine-3-carboxamide | $^1$H-NMR (400 MHz, CDCl$_3$): δ 8.06 (bs, 1H), 7.57 (bs, 1H), 7.21 (t, 1H), 6.89 (m, 2H), 6.82 (d, 2H), 6.55 (s, 1H), 4.71 (s, 2H), 3.70-3.69 (m, 1H), 3.60-3.57 (m, 1H), 3.37 (m, 1H), 2.11 (m, 1H), 1.99 (m, 1H), 1.76-1.73 (m, 2H), 1.40-1.23 (m, 4H); Mass (m/z): 402.2 (M + H)$^+$. |
| 33 | N-(cis-1S,2S-2-Hydroxycyclohexyl)-4-(2,3-difluorobenzyl)-4H-pyrido[3,2-b][1,4]oxazine-2-carboxamide | $^1$H-NMR (400 MHz, CDCl$_3$): δ 7.57 (d, J = 4.7 Hz, 1H), 7.21 (t, J = 5.8 Hz, 1H), 7.08-7.03 (m, 2H), 6.66 (d, J = 7.6 Hz, 1H), 6.56 (s, 1H), 5.94 (d, J = 6.6 Hz, 2H), 4.72 (s, 2H), 3.70-3.58 (m, 2H), 3.38-3.36 (m, 1H), 2.09-2.06 (d, 1H), 1.98-1.96 (m, 1H), 1.82-1.70 (m, 2H), 1.39-1.21 (m, 4H); Mass (m/z): 402.2 (M + H)$^+$. |

-continued

| Example Number | Chemical name and Structure | Characterization data |
|---|---|---|
| 34 | N-(cis-1S,2S-2-Hydroxycyclohexyl)-4-(3-fluoro pyridin-4-ylmethyl)-4H-benzo[1,4]oxazine-2-carboxamide | $^1$H-NMR (400 MHz, CDCl$_3$): δ 8.47 (s, 1H), 8.40 (d, J = 4.5 Hz, 1H), 7.44 (t, J = 5.3 Hz, 1H), 6.73-6.60 (m, 2H), 6.56-6.52 (m, 2H), 6.13 (d, J = 7.1 Hz, 1H), 6.03 (d, J = 6.6 Hz, 1H), 4.49 (s, 2H), 3.70-3.58 (m, 2H), 3.45-3.30 (m, 1H), 2.15-2.06 (d, 1H), 2.05-1.95 (m, 1H), 1.80-1.70 (m, 2H), 1.42-1.21 (m, 4H); Mass (m/z): 384.3 (M + H)$^+$. |
| 35 | N-(cis-1S,2S-2-Hydroxycyclohexyl)-4-(4-fluorobenzyl)-4H-pyrido[3,2-b][1,4]oxazine-2-carboxamide | $^1$H-NMR (400 MHz, CDCl$_3$): δ 7.60-7.55 (m, 1H), 7.40-7.30 (m, 2H), 7.10-6.97 (m, 2H), 6.64 (d, J = 7.2 Hz, 1H), 6.60-6.50 (m, 2H), 5.97-5.90 (m, 1H), 4.59 (s, 2H), 3.72-3.62 (m, 2H), 3.40-3.30 (m, 1H), 2.13-2.03 (m, 1H), 2.0-1.90 (m, 1H), 1.80-1.70 (m, 2H), 1.39-1.20 (m, 4H); Mass (m/z): 384.2 (M + H)$^+$. |
| 36 | N-(cis-1S,2S-2-Hydroxycyclohexyl)-1-(3-fluorobenzyl)-1H-pyrido[2,3-b][1,4]oxazine-3-carboxamide | $^1$H-NMR (400 MHz, CDCl$_3$): δ 7.60-7.50 (m, 1H), 7.40-7.30 (m, 2H), 7.10-6.97 (m, 2H), 6.64 (d, J = 7.2 Hz, 1H), 6.60-6.50 (m, 2H), 6.05-5.90 (m, 1H), 4.61 (s, 2H), 3.72-3.62 (m, 2H), 3.40-3.30 (m, 1H), 2.13-2.03 (m, 1H), 2.0-1.90 (m, 1H), 1.80-1.70 (m, 2H), 1.39-1.20 (m, 4H); Mass (m/z): 384.3 (M + H)$^+$. |

| Example Number | Chemical name and Structure | Characterization data |
|---|---|---|
| 37 | N-(cis-1S,2S-2-Hydroxycyclohexyl)-4-(2-trifluoromethylbenzyl)-4H-benzo[1,4]oxazine-2-carboxamide | $^1$H-NMR (400 MHz, CDCl$_3$): δ 7.78-7.68 (m, 2H), 7.56 (t, J = 7.5 Hz, 1H), 7.39 (t, J = 7.5 Hz, 1H), 6.70-6.50 (m, 4H), 6.07 (d, J = 7.5 Hz, 1H), 6.02 (d, J = 6.7 Hz, 1H), 4.61 (s, 2H), 3.82-3.68 (m, 2H), 3.45-3.36 (m, 1H), 2.15-2.05 (m, 1H), 2.0-1.90 (m, 1H), 1.80-1.70 (m, 2H), 1.40-1.20 (m, 4H); Mass (m/z): 433.3 (M + H)$^+$. |
| 38 | N-(cis-1S,2S-2-Hydroxycyclohexyl)-4-(2-chlorobenzyl)-8-fluoro-4H-benzo[1,4]oxazine-2-carboxamide | $^1$H-NMR (400 MHz, CDCl$_3$): δ 7.48 (d, J = 5.6 Hz, 1H), 7.39 (d, J = 7.0 Hz, 1H), 7.33-7.25 (m, 2H), 6.62-6.47 (m, 3H), 6.06 (d, J = 6.3 Hz, 1H), 5.92 (d, J = 7.6 Hz, 1H), 4.48 (s, 2H), 3.78-3.65 (m, 2H), 3.46-3.36 (m, 1H), 2.15-2.05 (m, 1H), 2.02-1.95 (m, 1H), 1.80-1.70 (m, 2H), 1.45-1.22 (m, 4H); Mass (m/z): 417.2 (M + H)$^+$. |
| 39 | N-(trans-1R,2R-2-Hydroxycyclopentyl)-4-(2,3-difluorobenzyl)-4H-benzo[1,4]oxazine-2-carboxamide | $^1$H-NMR (400 MHz, CDCl$_3$): δ 7.22 (t, J = 7.8 Hz, 1H), 7.15-7.03 (m, 2H), 6.70-6.63 (m, 2H), 6.55-6.50 (m, 2H), 6.28-6.20 (m, 1H), 6.15-6.10 (m, 1H), 4.46 (s, 2H), 4.05-3.96 (m, 1H), 3.90-3.82 (m, 1H), 2.78 (s, 1H), 2.22-2.12 (m, 1H), 2.10-2.01 (m, 1H), 1.90-1.80 (m, 1H), 1.80-1.63 (m, 2H), 1.55-1.50 (m, 1H); Mass (m/z): 387.2 (M + H)$^+$. |

| Example Number | Chemical name and Structure | Characterization data |
|---|---|---|
| 40 | N-(trans-1R,2R-2-Hydroxycyclopentyl)-4-(2-fluorobenzyl)-4H-benzo[1,4]oxazine-2-carboxamide 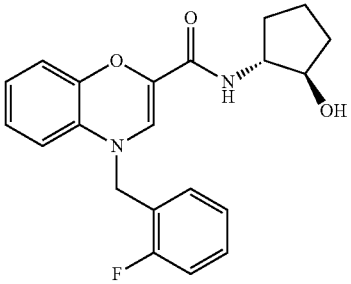 | ¹H-NMR (400 MHz, CDCl₃): δ 7.43 (t, J = 7.5 Hz, 1H), 7.32-7.25 (m, 2H), 7.09 (t, J = 9.5 Hz, 1H), 6.70-6.60 (m, 2H), 6.53 (s, 1H), 6.52-6.48 (m, 1H), 6.30-6.26 (m, 1H), 6.15-6.08 (m, 1H), 4.66 (bs, 1H), 4.46 (s, 2H), 4.02-3.96 (m, 1H), 3.90-3.80 (m, 1H), 2.23-2.13 (m, 1H), 2.10-2.0 (m, 1H), 1.88-1.80 (m, 1H), 1.80-1.65 (m, 2H), 1.55-1.50 (m, 1H); Mass (m/z): 369.3 (M + H)⁺. |
| 41 | N-(cis-1S,2S-2-Hydroxycyclohexyl)-4-(2-chlorobenzyl)-4H-benzo[1,4]oxazine-2-carboxamide 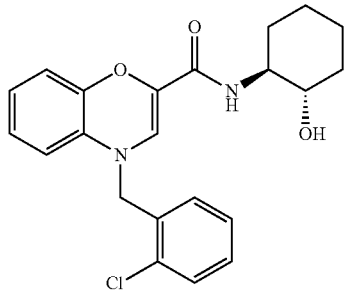 | ¹H-NMR (400 MHz, CDCl₃): δ 7.52-7.46 (m, 1H), 7.38-7.30 (m, 1H), 7.25-7.20 (m, 2H), 6.68-6.58 (m, 2H), 6.53-6.48 (m, 2H), 6.14-6.10 (m, 1H), 5.98 (d, J = 6.8 Hz, 1H), 4.47 (s, 2H), 3.74 (bs, 1H), 3.73-3.60 (m, 1H), 3.43-3.32 (m, 1H), 2.13-2.05 (m, 1H), 2.05-1.95 (m, 1H), 1.80-1.70 (m, 2H), 1.40-1.20 (m, 4H); Mass (m/z): 399.3 (M + H)⁺. |
| 42 | N-(trans-1R,2R-2-Hydroxycyclopentyl)-4-(2,3-difluorobenzyl)-8-fluoro-4H-benzo[1,4]oxazine-2-carboxamide 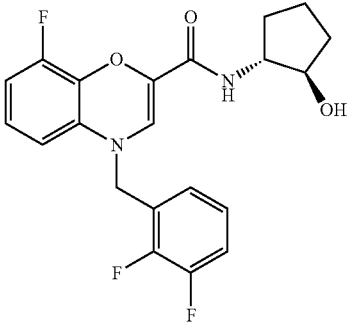 | ¹H-NMR (400 MHz, CDCl₃): δ 7.24-7.18 (m, 1H), 7.16-7.04 (m, 2H), 6.65-6.56 (m, 1H), 6.55-6.48 (m, 2H), 6.21-6.16 (m, 1H), 6.03 (d, J = 8.0 Hz, 1H), 4.88 (d, J = 7.6 Hz, 1H), 4.46 (s, 2H), 4.08-3.98 (m, 1H), 4.41-4.31 (m, 1H), 2.33-2.13 (m, 1H), 2.13-2.03 (m, 1H), 1.89-1.79 (m, 1H), 1.79-1.62 (m, 2H), 1.60-1.50 (m, 1H); Mass (m/z): 405.2 (M + H)⁺. |

| Example Number | Chemical name and Structure | Characterization data |
|---|---|---|
| 43 | N-(2-Hydroxymethylphenyl)-4-(2-fluorobenzyl)-4H-benzo[1,4]oxazine-2-carboxamide | $^1$H-NMR (400 MHz, CDCl$_3$): δ 9.0 (bs, 1H), 8.06 (d, J = 7.5 Hz, 1H), 7.58-7.50 (m, 1H), 7.42-7.25 (m, 3H), 7.22-7.05 (m, 3H), 6.75-6.62 (m, 3H), 6.62-6.57 (m, 1H), 6.36-6.27 (m, 1H), 4.72 (s, 2H), 4.50 (s, 2H), 2.35 (bs, 1H); Mass (m/z): 391.2 (M + H)$^+$. |
| 44 | N-(2-Hydroxymethylphenyl)-4-(2,3-difluorobenzyl)-8-fluoro-4H-benzo[1,4]oxazine-2-carboxamide | $^1$H-NMR (400 MHz, CDCl$_3$): δ 9.27 (bs, 1H), 8.12 (d, J = 8.0 Hz, 1H), 7.34 (t, J = 7.4 Hz, 1H), 7.30-7.20 (m, 2H), 7.19-7.10 (m, 3H), 6.70-6.55 (m, 3H), 6.07 (d, J = 7.9 Hz, 1H), 4.77 (s, 2H), 4.53 (s, 2H), 2.29 (bs, 1H); Mass (m/z): 427.2 (M + H)$^+$. |
| 45 | N-(2-Hydroxymethylphenyl)-4-(2,3-difluorobenzyl)-4H-benzo[1,4]oxazine-2-carboxamide | $^1$H-NMR (400 MHz, CDCl$_3$): δ 9.07 (bs, 1H), 8.08 (d, J = 7.9 Hz, 1H), 7.34 (t, J = 7.5 Hz, 1H), 7.20-7.02 (m, 4H), 6.70-6.55 (m, 5H), 6.30-6.25 (m, 1H), 4.73 (s, 2H), 4.53 (s, 2H), 2.31 (bs, 1H); Mass (m/z): 409.1 (M + H)$^+$. |

-continued

| Example Number | Chemical name and Structure | Characterization data |
|---|---|---|
| 46 | N-(2-Hydroxymethylphenyl)-4-(2-fluorobenzyl)-8-fluoro-4H-benzo[1,4]oxazine-2-carboxamide | $^1$H-NMR (400 MHz, CDCl$_3$): δ 9.24 (bs, 1H), 8.18-8.08 (m, 1H), 7.60-7.10 (m, 7H), 6.75-6.50 (m, 3H), 6.10 (d, J = 6.3 Hz, 1H), 4.76 (s, 2H), 4.43 (s, 2H), 2.32 (bs, 1H); Mass (m/z): 409.1 (M + H)$^+$. |
| 47 | N-(1-Hydroxymethyl-2-methylpropyl)-4-(2-fluorobenzyl)-8-fluoro-4H-benzo[1,4]oxazine-2-carboxamide | $^1$H-NMR (400 MHz, CDCl$_3$): δ 7.44 (t, J = 7.4 Hz, 1H), 7.35-7.26 (m, 1H), 7.14 (t, J = 7.5 Hz, 1H), 7.08 (t, J = 9.5 Hz, 1H), 6.65-6.50 (m, 3H), 6.26 (d, J = 7.3 Hz, 1H), 6.07 (d, J = 8.0 Hz, 1H), 4.46 (s, 2H), 3.86-3.76 (m, 2H), 3.76-3.64 (m, 1H), 2.89 (bs, 1H), 2.01-1.92 (m, 1H), 1.06-0.96 (m, 6H); Mass (m/z): 389.2 (M + H)$^+$. |
| 48 | N-(cis-1S,2S-2-Hydroxycyclohexyl)-4-benzyl-8-fluoro-4H-benzo[1,4]oxazine-2-carboxamide | $^1$H-NMR (400 MHz, CDCl$_3$): δ 7.43-7.36 (m, 5H), 7.36-7.26 (m, 2H), 6.62-6.46 (m, 2H), 6.10-6.02 (m, 1H), 4.41 (s, 2H), 3.80-3.70 (m, 1H), 3.48-3.38 (m, 1H), 2.80 (s, 1H), 2.18-2.10 (m, 1H), 2.10-1.96 (m, 1H), 1.85-1.72 (m, 2H), 1.42-1.20 (m, 4H); Mass (m/z): 383.3 (M + H)$^+$. |
| 49 | N-(cis-1R,2R-2-Hydroxycyclohexyl)-4-{2-fluorobenzyl}-4H-benzo[1,4]oxazine-2-carboxamide | $^1$H-NMR (400 MHz, CDCl$_3$): δ 7.45 (t, J = 7.4 Hz, 1H), 7.29 (t, J = 6.2 Hz, 1H), 7.17-7.05 (m, 2H), 6.72-6.62 (m, 2H), 6.56 (s, 1H), 6.56-6.49 (m, 1H), 6.30-6.23 (m, 1H), 5.99 (d, J = 6.7 Hz, 1H), 4.45 (s, 2H), 3.83 (bs, 1H), 3.76-3.65 (m, 1H), 3.45-3.36 (m, 1H), 2.15-2.06 (m, 1H), 2.05-1.95 (m, 1H), 1.82-1.70 (m, 2H), 1.42-1.18 (m, 4H); Mass (m/z): 383.4 (M + H)$^+$. |

| Example Number | Chemical name and Structure | Characterization data |
|---|---|---|
| 50 | N-(cis-1R,2R-2-Hydroxycyclohexyl)-4-{2-fluorobenzyl}-8-fluoro-4H-benzo[1,4]oxazine-2-carboxamide | $^1$H-NMR (400 MHz, CDCl$_3$): δ 7.44 (t, J = 7.3 Hz, 1H), 7.33-7.25 (m, 2H), 7.14 (t, J = 7.4 Hz, 1H), 7.08 (t, J = 8.9 Hz, 1H), 6.63-6.48 (m, 3H), 6.08-6.02 (m, 1H), 4.46 (s, 2H), 3.78-3.64 (m, 2H), 3.46-3.36 (m, 1H), 2.15-2.07 (m, 1H), 2.02-1.94 (m, 1H), 1.80-1.72 (m, 2H), 1.42-1.20 (m, 4H); Mass (m/z): 401.3 (M + H)$^+$. |
| 51 | N-(cis-1S,2S-2-Hydroxycyclohexyl)-4-{3-fluorobenzyl}-8-fluoro-4H-benzo[1,4]oxazine-2-carboxamide | $^1$H-NMR (400 MHz, CDCl$_3$): δ 7.40-7.30 (m, 1H), 7.14 (d, J = 7.6 Hz, 1H), 7.07 (d, J = 9.4 Hz, 1H), 6.98 (t, J = 8.3 Hz, 1H), 6.62-6.50 (m, 3H), 6.06 (d, J = 7.0 Hz, 1H), 5.98 (d, J = 7.8 Hz, 1H), 4.40 (s, 2H), 3.78-3.64 (m, 2H), 3.46-3.37 (m, 1H), 2.14-2.06 (m, 1H), 2.05-1.96 (m, 1H), 1.81-1.70 (m, 2H), 1.42-1.20 (m, 4H); Mass (m/z): 401.3 (M + H)$^+$. |
| 52 | N-(cis-1S,2S-2-Hydroxycyclohexyl)-4-(2-phenylpyridn-4-ylmethyl)-4H-benzo[1,4]oxazine-2-carboxamide | $^1$H-NMR (400 MHz, CDCl$_3$): δ 8.67 (d, J = 5.0 Hz, 1H), 7.98 (d, J = 7.3 Hz, 2H), 7.68 (s, 1H), 7.52-7.40 (m, 4H), 6.70-6.60 (m, 3H), 6.55 (dd, J = 1.2, 7.4 Hz, 1H), 6.14 (dd, J = 1.2, 7.3 Hz, 1H), 6.03 (d, J = 7.0 Hz, 1H), 4.47 (s, 2H), 3.80-3.63 (m, 1H), 3.49 (bs, 1H), 3.45-3.35 (m, 1H), 2.16-2.06 (m, 1H), 2.05-1.96 (m, 1H), 1.80-1.70 (m, 2H), 1.41-1.20 (m, 4H); Mass (m/z): 442.2 (M + H)$^+$. |

| Example Number | Chemical name and Structure | Characterization data |
|---|---|---|
| 53 | N-(cis-1S,2S-2-Hydroxycyclohexyl)-4-(2-phenylpyridin-4-ylmethyl)-8-fluoro-4H-benzo[1,4]oxazine-2-carboxamide<br />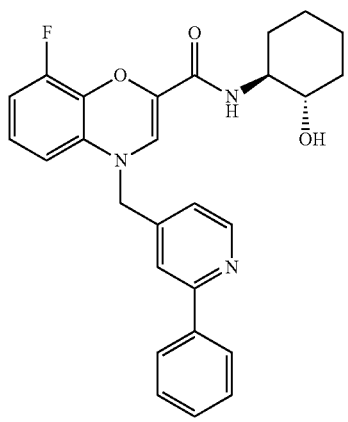 | $^1$H-NMR (400 MHz, CDCl$_3$): δ 8.68 (d, J = 4.7 Hz, 1H), 8.02-7.96 (m, 3H), 7.67 (s, 1H), 7.55-7.42 (m, 4H), 6.62-6.52 (m, 2H), 6.08 (d, J = 7.1 Hz, 1H), 5.93 (d, J = 7.3 Hz, 1H), 4.47 (s, 2H), 3.80-3.70 (m, 1H), 3.59 (bs, 1H), 3.48-3.38 (m, 1H), 2.16-2.06 (m, 1H), 2.05-1.96 (m, 1H), 1.80-1.70 (m, 2H), 1.41-1.20 (m, 4H); Mass (m/z): 460.1 (M + H)$^+$. |
| 54 | N-(cis-1S,2S-2-Hydroxycyclohexyl)-4-(2-chloropyridin-4-ylmethyl)-8-fluoro-4H-benzo[1,4]oxazine-2-carboxamide<br />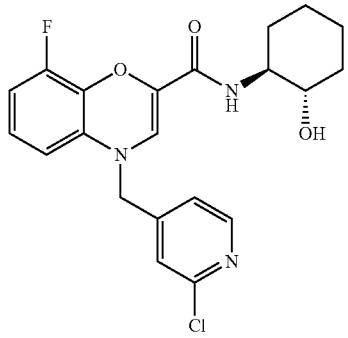 | $^1$H-NMR (400 MHz, CDCl$_3$): δ 8.39 (d, J = 5.0 Hz, 1H), 7.33 (s, 1H), 7.30-7.25 (m, 1H), 6.65-6.55 (m, 2H), 6.52 (s, 1H), 6.08 (d, J = 7.1 Hz, 1H), 5.85 (d, J = 7.4 Hz, 1H), 4.40 (s, 2H), 3.80-3.70 (m, 1H), 3.49 (bs, 1H), 3.48-3.38 (m, 1H), 2.16-2.06 (m, 1H), 2.05-1.96 (m, 1H), 3.80-3.70 (m, 2H), 1.41-1.20 (m, 4H); Mass (m/z): 418.2, 420.2 (M + H)$^+$. |
| 55 | N-(cis-1S,2S-2-Hydroxycyclohexyl)-4-(2-fluorobenzyl)-5-fluoro-4H-benzo[1,4]oxazine-2-carboxamide<br />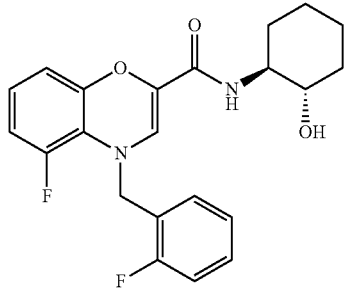 | $^1$H-NMR (400 MHz, CDCl$_3$): δ 7.48 (d, J = 7.4 Hz, 1H), 7.35-7.26 (m, 1H), 7.12 (t, J = 7.4 Hz, 1H), 7.06 (t, J = 9.4 Hz, 1H), 6.70-6.63 (m, 1H), 6.58-6.52 (m, 1H), 6.46 (s, 1H), 6.35 (d, J = 8.0 Hz, 1H), 5.95 (d, J = 6.7 Hz, 1H), 4.65 (s, 2H), 3.75-3.62 (m, 2H), 3.45-3.34 (m, 1H), 2.15-2.05 (m, 1H), 2.02-1.95 (m, 1H), 1.80-1.70 (m, 2H), 1.40-1.20 (m, 4H); Mass (m/z): 401.2 (M + H)$^+$. |

| Example Number | Chemical name and Structure | Characterization data |
|---|---|---|
| 56 | N-(cis-1S,2S-2-Hydroxycyclohexyl)-4-(pyridin-2-ylmethyl)-5-fluoro-4H-benzo[1,4]oxazine-2-carboxamide | $^1$H-NMR (400 MHz, CDCl$_3$): δ 8.58 (d, J = 4.1 Hz, 1H), 7.68 (t, J = 7.5 Hz, 1H), 7.46 (d, J = 7.7 Hz, 1H), 7.19 (t, J = 5.1 Hz, 1H), 6.70-6.62 (m, 1H), 6.55-6.45 (m, 2H), 6.37 (d, J = 7.9 Hz, 1H), 5.97 (d, J = 6.6 Hz, 1H), 4.69 (s, 2H), 3.75-3.62 (m, 2H), 3.42-3.35 (m, 1H), 2.15-2.05 (m, 1H), 2.02-1.95 (m, 1H), 1.80-1.70 (m, 2H), 1.40-1.20 (m, 4H); Mass (m/z): 384.3 (M + H)$^+$. |
| 57 | N-(cis-1S,2S-2-Hydroxycyclohexyl)-4-(pyridin-4-ylmethyl)-8-fluoro-4H-benzo[1,4]oxazine-2-carboxamide | $^1$H-NMR (400 MHz, CDCl$_3$): δ 8.60 (d, J = 4.0 Hz, 2H), 7.30 (d, J = 4.0 Hz, 2H), 6.62-6.52 (m, 3H), 6.07 (d, J = 6.7 Hz, 1H), 5.88 (d, J = 7.1 Hz, 1H), 4.42 (s, 2H), 3.78-3.65 (m, 1H), 3.56 (bs, 1H), 3.42-3.35 (m, 1H), 2.15-2.05 (m, 1H), 2.02-1.95 (m, 1H), 1.80-1.70 (m, 2H), 1.40-1.20 (m, 4H); Mass (m/z): 384.3 (M + H)$^+$. |
| 58 | N-(cis-1S,2S-2-Hydroxycyclohexyl)-4-(6'-fluoro-5'-methyl-[2,3']bipyridinyl-4-ylmethyl)-4H-benzo[1,4]oxazine-2-carboxamide | $^1$H-NMR (400 MHz, CDCl$_3$): δ 8.67 (d, J = 4.9 Hz, 1H), 8.05-8.0 (m, 1H), 8.27 (d, J = 8.8 Hz, 1H), 7.66 (s, 1H), 7.35-7.25 (m, 1H), 6.73-6.55 (m, 4H), 6.13 (d, J = 7.4 Hz, 1H), 6.04 (d, J = 6.5 Hz, 1H), 4.47 (s, 2H), 4.01 (bs, 1H), 3.80-3.63 (m, 1H), 3.45-3.35 (m, 1H), 2.36 (s, 3H), 2.16-2.06 (m, 1H), 2.05-1.96 (m, 1H), 1.80-1.70 (m, 2H), 1.41-1.20 (m, 4H); Mass (m/z): 475.2 (M + H)$^+$. |

| Example Number | Chemical name and Structure | Characterization data |
|---|---|---|
| 59 | N-(cis-1S,2S-2-Hydroxycyclohexyl)-4-[2-(1-methyl-1H-pyrazol-3-yl)-pyridin-4-ylmethyl]-4H-benzo[1,4]oxazine-2-carboxamide | $^1$H-NMR (400 MHz, CDCl$_3$): δ 8.51 (d, J = 5.0 Hz, 1H), 7.95 (d, J = 7.9 Hz, 2H), 7.40 (s, 1H), 7.13 (d, J = 4.7 Hz, 1H), 6.72-6.60 (m, 2H), 6.60-6.53 (m, 2H), 6.13 (d, J = 7.3 Hz, 1H), 6.03 (d, J = 6.4 Hz, 1H), 4.41 (s, 2H), 3.95 (s, 3H), 3.80-3.65 (m, 2H), 3.47-3.37 (m, 1H), 2.15-2.05 (m, 1H), 2.05-1.95 (m, 1H), 1.80-1.70 (m, 2H), 1.41-1.20 (m, 4H); Mass (m/z): 446.4 (M + H)$^+$. |
| 60 | N-(cis-1S,2S-2-Hydroxycyclohexyl)-4-(1-methyl-1H-pyrazol-3-ylmethyl)-4H-benzo[1,4]oxazine-2-carboxamide | $^1$H-NMR (400 MHz, CDCl$_3$): δ 7.29 (d, J = 2.0 Hz, 1H), 6.72-6.60 (m, 2H), 6.59 (s, 1H), 6.52-6.45 (m, 2H), 6.26 (d, J = 2.0 Hz, 1H), 5.96 (d, J = 6.6 Hz, 1H), 4.37 (s, 2H), 3.91 (bs, 1H), 3.86 (s, 3H), 3.72-3.60 (m, 21H), 3.42-3.32 (m, 1H), 2.12-2.07 (m, 1H), 2.02-1.93 (m, 1H), 1.80-1.70 (m, 2H), 1.40-1.20 (m, 4H); Mass (m/z): 369.3 (M + H)$^+$. |
| 61 | N-(cis-1S,2S-2-Hydroxycyclohexyl)-4-(2-fluorobenzyl)-5,8-difluoro-4H-benzo[1,4]oxazine-2-carboxamide | $^1$H-NMR (400 MHz, CDCl$_3$): δ 7.46 (t, J = 7.4 Hz, 1H), 7.32-7.27 (m, 1H), 7.13 (t, J = 7.3 Hz, 1H), 7.07 (t, J = 9.5 Hz, 1H), 6.56-6.42 (m, 3H), 6.01 (d, J = 6.8 Hz, 1H), 4.66 (s, 2H), 3.80-3.65 (m, 1H), 3.52 (d, J = 3.9 Hz, 1H), 3.45-3.34 (m, 1H), 2.15-2.05 (m, 1H), 2.02-1.95 (m, 1H), 1.80-1.70 (m, 2H), 1.40-1.20 (m, 4H); Mass (m/z): 419.2 (M + H)$^+$. |

| Example Number | Chemical name and Structure | Characterization data |
|---|---|---|
| 62 | N-(cis-1S,2S-2-Hydroxycyclohexyl)-4-(3-fluoropyridin-4-ylmethyl)-8-fluoro-4H-benzo[1,4]oxazine-2-carboxamide | $^1$H-NMR (400 MHz, CDCl$_3$): δ 8.48 (bs, 1H), 8.42 (bs, 1H), 7.44 (bs, 1H), 6.68-6.43 (m, 3H), 6.08 (d, J = 7.1 Hz, 1H), 5.93 (d, J = 7.8 Hz, 1H), 4.50 (s, 2H), 3.80-3.70 (m, 1H), 3.51 (bs, 1H), 3.48-3.38 (m, 1H), 2.15-2.08 (m, 1H), 2.05-1.95 (m, 1H), 1.80-1.72 (m, 2H), 1.42-1.21 (m, 4H); Mass (m/z): 402.2 (M + H)$^+$. |
| 63 | N-(cis-1S,2S-2-Hydroxycyclohexyl)-4-(2-methylpyridin-4-ylmethyl)-8-fluoro-4H-benzo[1,4]oxazine-2-carboxamide | $^1$H-NMR (400 MHz, CDCl$_3$): δ 8.37 (d, J = 7.6 Hz, 1H), 7.33 (d, J = 7.8 Hz, 1H), 7.28 (s, 1H), 6.68-6.43 (m, 3H), 6.08 (d, J = 7.3 Hz, 1H), 5.93 (d, J = 5.8 Hz, 1H), 4.48 (s, 2H), 3.80-3.70 (m, 1H), 3.51 (bs, 1H), 3.48-3.38 (m, 1H), 2.53 (s, 3H), 2.15-2.08 (m, 1H), 2.05-1.95 (m, 1H), 1.80-1.72 (m, 2H), 1.42-1.21 (m, 4H); Mass (m/z): 398.3 (M + H)$^+$. |
| 64 | N-(cis-1S,2S-2-Hydroxycyclohexyl)-4-(2-methylpyridin-5-ylmethyl)-8-fluoro-4H-benzo[1,4]oxazine-2-carboxamide | $^1$H-NMR (400 MHz, CDCl$_3$): δ 8.39 (s, 1H), 7.39 (d, J = 7.4 Hz, 1H), 7.33 (d, J = 7.4 Hz, 1H), 6.68-6.43 (m, 3H), 6.08 (d, J = 7.3 Hz, 1H), 5.93 (d, J = 5.8 Hz, 1H), 4.48 (s, 2H), 3.80-3.70 (m, 1H), 3.51 (bs, 1H), 3.48-3.38 (m, 1H), 2.56 (s, 3H), 2.15-2.08 (m, 1H), 2.05-1.95 (m, 1H), 1.80-1.72 (m, 2H), 1.42-1.21 (m, 4H); Mass (m/z): 398.2 (M + H)$^+$. |

| Example Number | Chemical name and Structure | Characterization data |
|---|---|---|
| 65 | N-(cis-1S,2S-2-Hydroxycyclohexyl)-4-(2-methylpyridin-4-ylmethyl)-4H-benzo[1,4]oxazine-2-carboxamide 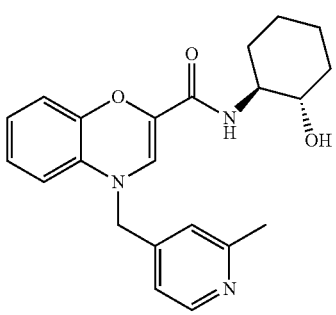 | $^1$H-NMR (400 MHz, CDCl$_3$): δ 8.35 (d, J = 7.5 Hz, 1H), 7.56 (d, J = 7.5 Hz, 1H), 7.35 (s, 1H), 7.10-6.95 (m, 2H), 6.70-6.50 (m, 3H), 6.01 (d, J = 5.2 Hz, 1H), 4.50 (s, 2H), 3.78-3.58 (m, 2H), 3.45-3.35, (m, 1H), 2.55 (s, 3H), 2.15-1.94 (m, 2H), 1.80-1.70 (m, 2H), 1.40-1.20 (m, 4H); Mass (m/z): 380.3 (M + H)$^+$. |
| 66 | N-(cis-1S,2S-2-Hydroxycyclohexyl)-4-(2-methylpyridin-5-ylmethyl)-4H-benzo[1,4]oxazine-2-carboxamide 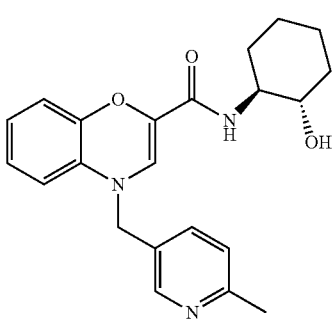 | $^1$H-NMR (400 MHz, CDCl$_3$): δ 8.41 (s, 1H), 7.52 (d, J = 7.4 Hz, 1H), 7.36 (d, J = 7.4 Hz, 1H), 7.10-6.95 (m, 2H), 6.70-6.50 (m, 3H), 6.01 (d, J = 5.2 Hz, 1H), 4.50 (s, 2H), 3.78-3.58 (m, 2H), 3.45-3.35, (m, 1H), 2.55 (s, 3H), 2.15-1.94 (m, 2H), 1.80-1.70 (m, 2H), 1.40-1.20 (m, 4H); Mass (m/z): 380.1 (M + H)$^+$. |
| 67 | N-(cis-1S,2S-2-Hydroxycyclohexyl)-4-(pyridin-4-ylmethyl)-5,8-difluoro-4H-benzo[1,4]oxazine-2-carboxamide 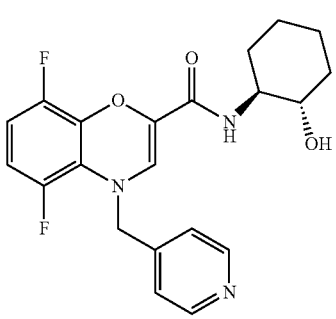 | $^1$H-NMR (400 MHz, CDCl$_3$): δ 8.60 (bs, 2H), 7.32 (d, J = 4.3 Hz, 2H), 6.62-6.42 (m, 3H), 6.04 (d, J = 7.1 Hz, 1H), 4.57 (s, 2H), 3.78-3.65 (m, 1H), 3.46-3.35 (m, 2H), 2.13-2.07 (m, 1H), 2.02-1.95 (m, 1H), 1.78-1.70 (m, 2H), 1.43-1.22 (m, 4H); Mass (m/z): 402.3 (M + H)$^+$. |

-continued

| Example Number | Chemical name and Structure | Characterization data |
|---|---|---|
| 68 | N-(3-Hydroxytetrahydropyran-4-yl)-4-(3-fluorobenzyl)-4H-benzo[1,4]oxazine-2-carboxamide | $^1$H-NMR (400 MHz, CDCl$_3$): δ 7.38-7.30 (m, 1H), 7.15 (d, J = 7.7 Hz, 1H), 7.08 (d, J = 9.3 Hz, 1H), 6.98 (t, J = 8.0 Hz, 1H), 6.72-6.62 (m, 2H), 6.58 (s, 1H), 6.55 (dd, J = 1.6, 7.4 Hz, 1H), 6.21 (dd, J = 1.6, 7.4 Hz, 1H), 6.05 (d, J = 5.7 Hz, 1H), 4.57 (d, J = 2.8 Hz, 1H), 4.41 (s, 2H), 4.08 (dd, J = 4.8, 11.2 Hz, 1H), 4.0 (dd, J = 4.1, 11.2 Hz, 1H), 3.90-3.80 (m, 1H), 3.60-3.50 (m, 1H), 3.45 (t, J = 10.2 Hz, 1H), 3.16 (t, J = 10.7 Hz, 1H), 2.01-1.93 (m, 1H), 1.78-1.70 (m, 1H); Mass (m/z): 385.3 (M + H)$^+$. |
| 69 | N-(3-Hydroxytetrahydropyran-4-yl)-4-(4-fluorobenzyl)-8-fluoro-4H-benzo[1,4]oxazine-2-carboxamide | $^1$H-NMR (400 MHz, CDCl$_3$): δ 7.38-7.32 (m, 2H), 7.12-7.03 (m, 2H), 6.63-6.51 (m, 3H), 6.10 (d, J = 5.8 Hz, 1H), 6.02 (d, J = 7.8 Hz, 1H), 4.45 (d, J = 2.8 Hz, 1H), 4.39 (s, 2H), 4.07 (dd, J = 4.9, 11.3 Hz, 1H), 3.99 (dd, J = 4.0, 11.3 Hz, 1H), 3.90-3.80 (m, 1H), 3.60-3.50 (m, 1H), 3.42 (t, J = 10.4 Hz, 1H), 3.15 (t, J = 10.4 Hz, 1H), 2.0-1.92 (m, 1H), 1.78-1.62 (m, 1H); Mass (m/z): 403.4 (M + H)$^+$. |
| 70 | N-(3-Hydroxytetrahydropyran-4-yl)-4-(3-trifluoromethylbenzyl)-4H-benzo[1,4]oxazine-2-carboxamide | $^1$H-NMR (400 MHz, CDCl$_3$): δ 7.64-7.56 (m, 3H), 7.55-7.48 (m, 1H), 6.75-6.63 (m, 2H), 6.59 (s, 1H), 6.56 (d, J = 7.3 Hz, 1H), 6.18 (d, J = 7.3 Hz, 1H), 6.07 (d, J = 5.5 Hz, 1H), 4.53 (d, J = 2.4 Hz, 1H), 4.47 (s, 2H), 4.08 (dd, J = 4.8, 11.3 Hz, 1H), 4.0 (dd, J = 3.4, 11.3 Hz, 1H), 3.90-3.80 (m, 1H), 3.60-3.50 (m, 1H), 3.42 (t, J = 11.9 Hz, 1H), 3.16 (t, J = 11.9 Hz, 1H), 2.02-1.93 (m, 1H), 1.80-1.65 (m, 1H); Mass (m/z): 435.3 (M + H)$^+$. |

| Example Number | Chemical name and Structure | Characterization data |
|---|---|---|
| 71 | N-(3-Hydroxytetrahydropyran-4-yl)-4-(2-methoxypyridin-5-ylmethyl)-4H-benzo[1,4]oxazine-2-carboxamide | $^1$H-NMR (400 MHz, CDCl$_3$): δ 8.16 (bs, 1H), 7.60 (d, J = 8.5 Hz, 1H), 6.76 (d, J = 8.5 Hz, 1H), 6.72-6.65 (m, 2H), 6.57 (s, 1H), 6.56-6.52 (m, 1H), 6.35-6.28 (m, 1H), 6.03 (d, J = 5.8 Hz, 1H), 4.57 (d, J = 2.3 Hz, 1H), 4.35 (s, 2H), 4.07 (dd, J = 4.9, 11.4 Hz, 1H), 3.99 (dd, J = 4.1, 11.4 Hz, 1H), 3.92 (s, 3H), 3.90-3.80 (m, 1H), 3.60-3.52 (m, 1H), 3.42 (t, J = 11.7 Hz, 1H), 3.15 (t, J = 11.7 Hz, 1H), 2.0-1.92 (m, 1H), 1.80-1.65 (m, 1H); Mass (m/z): 398.4 (M + H)$^+$. |
| 72 | N-(3-Hydroxytetrahydropyran-4-yl)-4-(pyridin-4-ylmethyl)-8-fluoro-4H-benzo[1,4]oxazine-2-carboxamide | $^1$H-NMR (400 MHz, CDCl$_3$): δ 8.61 (bs, 2H), 7.30 (bs, 2H), 6.65-6.52 (m, 3H), 6.12 (d, J = 6.0 Hz, 1H), 5.91 (d, J = 7.0 Hz, 1H), 4.43 (s, 2H), 4.36 (bs, 1H), 4.07 (dd, J = 4.9, 11.3 Hz, 1H), 4.0 (dd, J = 4.2, 11.3 Hz, 1H), 3.90-3.80 (m, 1H), 3.60-3.52 (m, 1H), 3.42 (t, J = 11.6 Hz, 1H), 3.16 (t, J = 11.6 Hz, 1H), 2.02-1.96 (m, 1H), 1.80-1.66 (m, 1H); Mass (m/z): 386.0 (M + H)$^+$. |

Example 73

N-(3-Fluoropiperidin-4-yl)-4-(2-fluorobenzyl)-8-fluoro-4H-benzo[1,4]oxazine-2-carboxamide hydrochloride

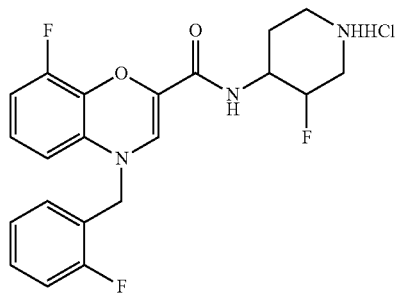

Step 1: Preparation of N-(1-tertbutoxycarbonyl-3-fluoropiperidin-4-yl)-4-(2-fluoro benzyl)-8-fluoro-4H-benzo[1,4]oxazine-2-carboxamide 4-(2-Fluorobenzyl)-8-fluoro-4H-benzo[1,4]oxazine-2-carboxylic acid (I-34) was treated with tert-butyl 4-amino-3-fluoropiperidine-1-carboxylate in presence of HATU by following the procedure as described in the preparation of example 1 to obtain the title compound.

$^1$H-NMR (400 MHz, CDCl$_3$): δ 7.44 (t, J=7.2 Hz, 1H), 7.36-7.28 (m, 1H), 7.14 (t, J=7.5 Hz, 1H), 7.08 (t, J=8.9 Hz, 1H), 6.67-6.50 (m, 3H), 6.49 (d, J=8.2 Hz, 1H), 6.05 (d, J=7.9 Hz, 1H), 4.74 (d, J=52.0 Hz, 1H), 4.46 (s, 2H), 4.38-4.10 (m, 3H), 3.10-2.80 (m, 2H), 1.91-1.72 (m, 2H), 1.47 (s, 9H); Mass (m/z): 504.4 (M+H)$^+$.

Step 2: Preparation of N-(3-Fluoropiperidin-4-yl)-4-(2-fluorobenzyl)-8-fluoro-4H-benzo[1,4]oxazine-2-carboxamide hydrochloride To a stirred solution of the compound obtained in the above step 1 (50.0 mg, 0.1 mmol) in IPA (1.0 mL) cooled at 0° C., a solution of 3N HCl in IPA (0.5 mL) was added. The reaction mixture was stirred for 1 hour and the volatiles were removed under reduced pressure to obtain a mass which was washed several times with ether to afford the title compound.

Yield: 43 mg; $^1$H-NMR (400 MHz, DMSO-d$_6$): δ 9.22 (bs, 1H), 8.63 (bs, 1H), 7.51 (t, J=7.2 Hz, 1H), 7.42-7.36 (m, 1H), 7.32-7.18 (m, 2H), 7.12 (d, J=7.6 Hz, 1H), 6.80 (s, 1H), 6.78-6.62 (m, 2H), 6.28 (d, J=7.3 Hz, 1H), 5.03 (d, J=47.6 Hz, 1H), 4.62 (s, 2H), 4.50-4.40 (m, 1H), 4.40-4.15 (m, 2H), 3.20-3.0 (m, 2H), 2.10-1.96 (m, 1H), 1.90-1.80 (m, 1H); Mass (m/z): 404.2 (M+H)$^+$.

Example 74

N-(3-Fluoropiperidin-4-yl)-4-(2,3-difluorobenzyl)-8-fluoro-4H-benzo[1,4]oxazine-2-carboxamide hydrochloride

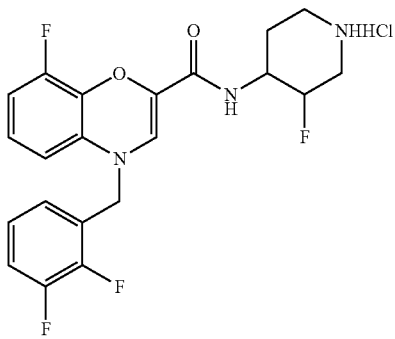

Step 1: Preparation of N-(1-tertbutoxycarbonyl-3-fluoropiperidin-4-yl)-4-(2,3-difluoro benzyl)-8-fluoro-4H-benzo[1,4]oxazine-2-carboxamide This compound was prepared using step 1 procedure of example 73.

$^1$H-NMR (400 MHz, CDCl$_3$): δ 7.28-7.20 (m, 1H), 7.20-7.06 (m, 2H), 6.68-6.50 (m, 3H), 6.34 (d, J=8.3 Hz, 1H), 6.02 (d, J=7.9 Hz, 1H), 4.73 (d, J=49.8 Hz, 1H), 4.48 (s, 2H), 4.40-4.10 (m, 3H), 3.12-2.78 (m, 2H), 1.92-1.78 (m, 2H), 1.46 (s, 9H); Mass (m/z): 522.3 (M+H)$^+$.

Step 2: Preparation of N-(3-fluoro piperidin-4-yl)-4-(2,3-difluorobenzyl)-8-fluoro-4H-benzo[1,4]oxazine-2-carboxamide hydrochloride This compound was prepared using step 2 procedure of example 73.

$^1$H-NMR (400 MHz, DMSO-d$_6$): δ 9.16 (bs, 1H), 8.62 (bs, 1H), 7.50-7.10 (m, 3H), 6.81 (s, 1H), 6.80-6.70 (m, 2H), 6.68-6.40 (m, 1H), 6.29 (d, J=7.1 Hz, 1H), 5.03 (d, J=48.3 Hz, 1H), 4.71 (s, 2H), 4.35-4.10 (m, 2H), 3.20-3.0 (m, 2H), 2.10-1.98 (m, 1H), 1.90-1.80 (m, 1H); Mass (m/z): 422.3 (M+H)$^+$.

Example 75

N-(3-Hydroxypiperidin-4-yl)-4-(2,3-difluorobenzyl)-8-fluoro-4H-benzo[1,4]oxazine-2-carboxamide trifluoroacetate

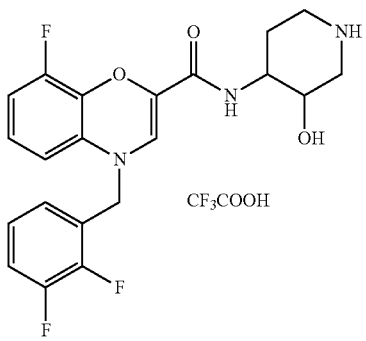

Step 1: Preparation of N-(1-tertbutoxycarbonyl-3-hydroxypiperidin-4-yl)-4-(2,3-difluoro benzyl)-8-fluoro-4H-benzo[1,4]oxazine-2-carboxamide The title compound was prepared using step 1 procedure of example 73.

$^1$H-NMR (400 MHz, CDCl$_3$): δ 7.25-7.16 (m, 1H), 7.16-7.05 (m, 2H), 6.70-6.50 (m, 3H), 6.12-6.02 (m, 2H), 4.49 (s, 2H), 4.40-4.10 (m, 3H), 3.88-3.78 (m, 1H), 3.50-3.38 (m, 1H), 2.80-2.70 (m, 1H), 2.70-2.55 (m, 1H), 1.98-1.90 (m, 1H), 1.60-1.50 (m, 1H), 1.45 (s, 9H); Mass (m/z): 520.2 (M+H)$^+$.

Step 2: Preparation of N-(3-hydroxypiperidin-4-yl)-4-(2,3-difluoro benzyl)-8-fluoro-4H-benzo[1,4]oxazine-2-carboxamide trifluoroacetate To the stirred solution of compound obtained in step 1 (75.0 mg, 0.14 mmol) in DCM (0.7 mL) cooled at 0° C. trifluoroacetic acid (0.7 mL) was added. The reaction mixture was stirred at RT for an hour and the volatiles were removed under reduced pressure to obtain a crude mass which was triturated several times with ether to obtain the title compound.

$^1$H-NMR (400 MHz, DMSO-d$_6$): δ 8.64 (bs, 2H), 7.50-7.10 (m, 3H), 6.80-6.70 (m, 3H), 6.35-6.25 (m, 1H), 5.60-5.50 (m, 1H), 4.70 (s, 2H), 3.90-3.70 (m, 2H), 3.60-3.20 (m, 3H), 3.20-3.0 (m, 2H), 2.10-1.98 (m, 1H), 1.90-1.80 (m, 1H); Mass (m/z): 420.3 (M+H)$^+$.

Example 76

N-(3-Hydroxypiperidin-4-yl)-4-(2-fluorobenzyl)-4H-benzo[1,4]oxazine-2-carboxamide trifluoroacetate

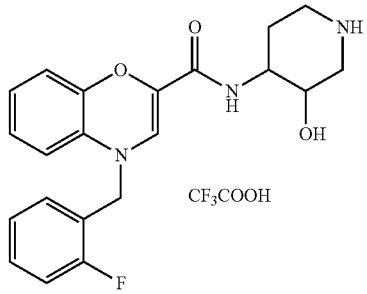

Step 1: Preparation of N-(1-tertbutoxycarbonyl-3-hydroxypiperidin-4-yl)-4-(2-fluoro benzyl)-4H-benzo[1,4]oxazine-2-carboxamide The title compound was prepared using step 1 procedure of example 73.

$^1$H-NMR (400 MHz, CDCl$_3$): δ 7.50-7.40 (m, 1H), 7.20-7.20 (m, 1H), 7.18-7.02 (m, 2H), 6.72-6.62 (m, 2H), 6.59 (s, 1H), 6.55-6.48 (m, 1H), 6.32-6.25 (m, 1H), 6.02 (d, J=5.9 Hz, 1H), 4.46 (s, 2H), 4.40-4.10 (m, 3H), 3.83-3.75 (m, 1H), 3.50-3.40 (m, 1H), 2.80-2.70 (m, 1H), 2.70-2.57 (m, 1H), 1.98-1.90 (m, 1H), 1.60-1.50 (m, 1H), 1.45 (s, 9H); Mass (m/z): 484.3 (M+H)$^+$.

Step 2: Preparation of N-(3-Hydroxypiperidin-4-yl)-4-(2-fluorobenzyl)-4H-benzo[1,4]oxazine-2-carboxamide trifluoroacetate The title compound was prepared using step 2 procedure of example 75.

$^1$H-NMR (400 MHz, DMSO-d$_6$): δ 8.61 (bs, 2H), 7.70-7.10 (m, 5H), 6.80-6.60 (m, 3H), 6.50-6.40 (m, 1H), 5.50 (d, J=3.9 Hz, 1H), 4.61 (s, 2H), 3.90-3.70 (m, 2H), 3.40-3.25 (m, 3H), 3.10-2.90 (m, 2H), 2.88-1.78 (m, 1H), 1.70-1.60 (m, 1H); Mass (m/z): 384.3 (M+H)$^+$.

Examples 77 to 80

The compounds of Example 77 to 80 were prepared by following the experimental procedures as described in the Examples 75 and 76 given above, with some non-critical variations.

| Example Number | Chemical name and Structure | Characterization data |
| --- | --- | --- |
| 77 | N-(3-Hydroxypiperidin-4-yl)-4-(4-fluorobenzyl)-8-fluoro-4H-benzo[1,4]oxazine-2-carboxamide trifluoroacetate | $^1$H-NMR (400 MHz, DMSO-d$_6$): δ 8.69 (bs, 1H), 8.53 (bs, 1H), 7.55-7.41 (m, 2H), 7.30-7.15 (m, 2H), 6.74 (s, 1H), 6.70-6.60 (m, 2H), 6.26 (d, J = 7.4 Hz, 1H), 5.53 (bs, 1H), 4.56 (s, 2H), 3.88-3.70 (m, 2H), 3.40-3.25 (m, 2H), 3.10-2.93 (m, 1H), 2.88-2.76 (m, 1H), 2.0-1.91 (m, 1H), 1.78-1.62 (m, 1H); Mass (m/z): 402.3 (M + H)$^+$. |
| 78 | N-(3-Hydroxypiperidin-4-yl)-4-(4-fluorobenzyl)-4H-benzo[1,4]oxazine-2-carboxamide trifluoroacetate | $^1$H-NMR (400 MHz, DMSO-d$_6$): δ 8.63 (bs, 1H), 8.52 (bs, 1H), 7.50-7.42 (m, 2H), 7.26 (d, J = 7.7 Hz, 1H), 7.22 (d, J = 9.8 Hz, 1H), 7.11 (t, J = 8.7 Hz, 1H), 6.70 (s, 1H), 6.70-6.65 (m, 2H), 6.62-6.57 (m, 1H), 6.42-6.37 (m, 1H), 5.51 (d, J = 4.9 Hz, 1H), 4.59 (s, 2H), 3.90-3.70 (m, 2H), 3.10-2.90 (m, 3H), 2.88-2.75 (m, 1H), 2.0-1.94 (m, 1H), 1.78-1.63 (m, 1H); Mass (m/z): 384.2 (M + H)$^+$. |
| 79 | N-(3-Hydroxypiperidin-4-yl)-4-(2,3-difluorobenzyl)-4H-benzo[1,4]oxazine-2-carboxamide trifluoroacetate | $^1$H-NMR (400 MHz, DMSO-d$_6$): δ 8.63 (bs, 1H), 8.50 (bs, 1H), 7.45 (d, J = 7.7 Hz, 1H), 7.43-7.33 (m, 1H), 7.30 (t, J = 7.1 Hz, 1H), 7.28-7.20 (m, 1H), 6.75-6.70 (m, 3H), 6.65-6.60 (m, 1H), 6.48-6.40 (m, 1H), 5.49 (bs, 1H), 4.59 (s, 2H), 3.88-3.72 (m, 2H), 3.40-3.25 (m, 2H), 3.05-2.92 (m, 1H), 2.85-2.75 (m, 1H), 1.98-1.92 (m, 1H), 1.72-1.62 (m, 1H); Mass (m/z): 402.3 (M + H)$^+$. |

| Example Number | Chemical name and Structure | Characterization data |
|---|---|---|
| 80 | N-(3-Hydroxypiperidin-4-yl)-4-(2-fluorobenzyl)-8-fluoro-4H-benzo[1,4]oxazine-2-carboxamide trifluoroacetate 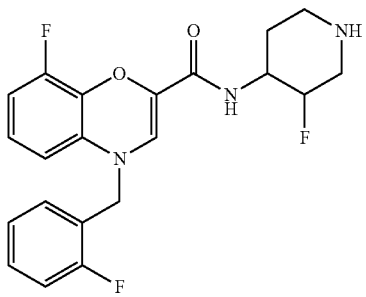 [SMILES: O=C(NC1CCNCC1F)C1=CN(Cc2ccccc2F)c2cccc(F)c2O1] CF$_3$COOH | $^1$H-NMR (400 MHz, DMSO-d$_6$): δ 8.64 (bs, 1H), 8.47 (bs, 1H), 7.52 (t, J = 7.5 Hz, 1H), 7.40-7.33 (m, 1H), 7.29-7.20 (m, 3H), 6.76-6.62 (m, 3H), 6.27 (d, J = 7.6 Hz, 1H), 5.53 (d, J = 4.7 Hz, 1H), 4.63 (s, 2H), 3.85-3.70 (m, 2H), 3.30-3.18 (m, 2H), 3.02-2.90 (m, 1H), 2.80-2.70 (m, 1H), 2.0-1.90 (m, 1H), 1.75-1.62 (m, 1H); Mass (m/z): 402.2 (M + H)$^+$. |

Example 81

N-(3-Fluoropiperidin-4-yl)-4-(2-fluorobenzyl)-8-fluoro-4H-benzo[1,4]oxazine-2-carboxamide To a stirred solution of N-(3-fluoropiperidin-4-yl)-4-(2-fluorobenzyl)-8-fluoro-4H-benzo[1,4]oxazine-2-carboxamide hydrochloride (example 73, 20.0 mg, 0.045 mmol) in ethyl acetate (2.0 mL), cooled at 0° C., a solution of NaOH (1N, 0.5 mL) was added. The reaction mixture was stirred for 5 minutes and the two layers were separated. The organic layer was washed with brine, dried over anhydrous Na$_2$SO$_4$ and the solvent was removed under reduced pressure to obtain the title compound.

Yield: 15.0 mg; $^1$H-NMR (400 MHz, CDCl$_3$): δ 7.44 (t, J=7.3 Hz, 1H), 7.35-7.25 (m, 1H), 7.13 (t, J=7.4 Hz, 1H), 7.08 (t, J=9.4 Hz, 1H), 6.63-6.43 (m, 3H), 6.33 (d, J=8.6 Hz, 1H), 6.05 (d, J=7.9 Hz, 1H), 4.70 (d, J=50.1 Hz, 1H), 4.46 (s, 2H), 4.23-4.10 (m, 1H), 3.40-3.28 (m, 1H), 3.20-3.10 (m, 1H), 2.90-2.65 (m, 2H), 1.70-1.60 (m, 2H); Mass (m/z): 404.3 (M+H)$^+$.

Examples 82 to 84

The compounds of Example 82 to 84 were prepared by following the experimental procedures as described in the Example 81 given above, with some non-critical variations.

| Example Number | Chemical name and Structure | Characterization data |
|---|---|---|
| 82 | N-(3-Fluoropiperidin-4-yl)-4-(2,3-difluorobenzyl)-8-fluoro-4H-benzo[1,4]oxazine-2-carboxamide | $^1$H-NMR (400 MHz, CDCl$_3$): δ 7.44-7.10 (m, 3H), 6.80 (s, 1H), 6.80-6.72 (m, 2H), 6.69-6.39 (m, 1H), 6.26 (d, J = 7.1 Hz, 1H), 5.03 (d, J = 48.6 Hz, 1H), 4.64 (s, 2H), 4.35-4.10 (m, 2H), 3.20-3.0 (m, 2H), 2.10-1.98 (m, 1H), 1.90-1.80 (m, 1H); Mass (m/z): 422.3 (M + H)$^+$. |

-continued

| Example Number | Chemical name and Structure | Characterization data |
|---|---|---|
| 83 | N-(3-Hydroxypiperidin-4-yl)-4-(2,3-difluorobenzyl)-8-fluoro-4H-benzo[1,4]oxazine-2-carboxamide | $^1$H-NMR (400 MHz, CDCl$_3$): δ 7.26-7.20 (m, 1H), 7.18-7.05 (m, 2H), 6.68-6.50 (m, 3H), 6.10 (d, J = 6.1 Hz, 1H), 6.04 (d, J = 7.8 Hz, 1H), 4.49 (s, 2H), 3.88-3.72 (m, 1H), 3.55-3.45 (m, 1H), 3.38-3.28 (m, 1H), 3.12-3.02 (m, 2H), 2.70-2.60 (m, 1H), 2.60-2.50 (m, 1H), 2.0-1.92 (m, 1H), 1.60-1.50 (m, 1H); Mass (m/z): 420.3 (M + H)$^+$. |
| 84 | N-(3-Hydroxypiperidin-4-yl)-4-(2-fluorobenzyl)-4H-benzo[1,4]oxazine-2-carboxamide | $^1$H-NMR (400 MHz, CDCl$_3$): δ 7.44 (t, J = 7.2 Hz, 1H), 7.32-7.27 (m, 1H), 7.12 (t, J = 7.4 Hz, 1H), 7.07 (t, J = 9.8 Hz, 1H), 6.70-6.62 (m, 2H), 6.58 (s, 1H), 6.55-6.48 (m, 1H), 6.30-6.24 (m, 1H), 6.06 (d, J = 5.6 Hz, 1H), 4.45 (s, 2H), 3.82-3.72 (m, 1H), 3.51-3.43 (m, 1H), 3.45-3.37 (m, 1H), 3.12-3.05 (m, 2H), 2.72-2.62 (m, 1H), 2.62-2.50 (m, 1H), 2.05-1.95 (m, 1H), 1.62-1.50 (m, 1H); Mass (m/z): 384.3 (M + H)$^+$. |

Example 85

N-(cis-1S,2S-2-Hydroxycyclohexyl)-4-(2,3-difluorobenzyl)-4H-benzo[1,4]thiazine-2-carboxamide

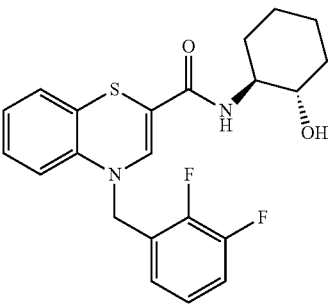 [SMILES: O=C(N[C@H]1CCCC[C@@H]1O)C1=CN(Cc2cccc(F)c2F)c2ccccc2S1]

To a solution of the intermediate, I-39 (200.8 mg, 0.63 mmol) in dichloromethane (2.0 mL) at RT, DIPEA (0.27 mL, 01.56 mmol), HATU (0.29 g, 0.75 mmol) and (1S,2S) 2-amino cyclohexanol hydrochloride (94.5 mg, 0.63 mmol) was added sequentially while stirring vigorously. After completion of addition, the reaction mixture was stirred for 16 hours and diluted with dichloromethane. The reaction mass was washed with water, brine, dried over anhydrous Na$_2$SO$_4$ and the solvent was evaporated under vacuum. The crude mass obtained was purified using silica gel column chromatography to afford the title compound.

Yield: 210.0 mg; $^1$H-NMR (400 MHz, CDCl$_3$): δ 7.39 (s, 1H), 7.18-7.03 (m, 3H), 7.03-6.91 (m, 3H), 6.55 (d, J=7.9 Hz, 1H), 6.0 (d, J=6.7 Hz, 1H), 4.83 (s, 2H), 3.77 (d, J=3.8 Hz, 1H), 3.80-3.67 (m, 1H), 3.45-3.35 (m, 1H), 2.17-2.08 (m, 1H), 2.05-1.98 (m, 1H), 1.82-1.72 (m, 2H), 1.43-1.22 (m, 4H); Mass (m/z): 417.3 (M+H)$^+$.

Examples 86 to 92

The compounds of Examples 86 to 92 were prepared by following the experimental procedures as described in the Example 85 given above, with some noncritical variations

| Example Number | Chemical name and Structure | Characterization data |
|---|---|---|
| 86 | N-(cis-1S,2S-2-Hydroxycyclohexyl)-4-(3-fluorobenzyl)-4H-benzo[1,4]thiazine-2-carboxamide | ¹H-NMR (400 MHz, CDCl₃): δ 77.42-7.30 (m, 2H), 7.20-6.85 (m, 6H), 6.53 (d, J = 6.1 Hz, 1H), 6.05-5.96 (m, 1H), 4.75 (s, 2H), 3.90-3.62 (m, 2H), 3.48-3.32 (m, 1H), 2.13-1.92 (m, 2H), 1.80-1.70 (m, 2H), 1.42-1.19 (m, 4H); Mass (m/z): 399.4 (M + H )⁺. |
| 87 | N-(cis-1S,2S-2-Hydroxycyclohexyl)-4-benzyl-4H-benzo[1,4]thiazine-2-carboxamide | ¹H-NMR (400 MHz, CDCl₃): δ 7.41 (s, 1H), 7.40-7.25 (m, 5H), 6.98-6.85 (m, 3H), 6.57 (d, J = 8.0 Hz, 1H), 5.99 (d, J = 6.5 Hz, 1H), 4.77 (s, 2H), 3.88 (bs, 1H), 3.75-3.63 (m, 1H), 3.43-3.35 (m, 1H), 2.13-2.05 (m, 1H), 2.05-1.95 (m, 1H), 1.80-1.72 (m, 2H), 1.43-1.20 (m, 4H); Mass (m/z): 381.3 (M + H)⁺. |
| 88 | N-(cis-1S,2S)-2-Hydroxycyclohexyl)-4-{4-methoxybenzyl}-4H-benzo[1,4]thiazine-2-carboxamide | ¹H-NMR (400 MHz, DMSO-d₆): δ 7.42-7.20 (m, 4H), 7.0-6.90 (m, 2H), 6.90-6.70 (m, 3H), 6.52 (d, J = 7.4 Hz, 1H), 4.62 (s, 2H), 4.55 (bs, 1H), 3.72 (s, 3H), 3.60-3.20 (m, 2H), 1.92-1.78 (m, 2H), 1.70-1.55 (m, 2H), 1.45-1.20 (m, 4H); Mass (m/z): 411.1 (M + H)⁺. |

| Example Number | Chemical name and Structure | Characterization data |
|---|---|---|
| 89 | N-(cis-1S,2S-2-Hydroxycyclohexyl)-4-{4-fluorobenzyl}-4H-benzo[1,4]thiazine-2-carboxamide | $^1$H-NMR (400 MHz, CDCl$_3$): δ 7.33 (s, 1H), 7.38-7.28 (m, 2H), 7.10-7.0 (m, 2H), 7.0-6.90 (m, 3H), 6.55 (d, J = 7.8 Hz, 1H), 5.99 (d, J = 6.5 Hz, 1H), 4.73 (s, 2H), 3.90-3.80 (bs, 1H), 3.75-3.62 (m, 2H), 2.10-1.92 (m, 2H), 1.81-1.70 (m, 2H), 1.42-1.18 (m, 4H); Mass (m/z): 399.3 (M + H)$^+$. |
| 90 | N-(cis-1S,2S-2-Hydroxycyclohexyl)-4-{pyridin-4-ylmethyl}-4H-benzo[1,4]thiazine-2-carboxamide | $^1$H-NMR (400 MHz, CDCl$_3$): δ 8.60 (d, J = 5.1 Hz, 2H), 7.38 (s, 1H), 7.29 (d, J = 5.1 Hz, 2H), 7.02-6.90 (m, 3H), 6.43 (d, J = 7.6 Hz, 1H), 6.02 (d, J = 6.6 Hz, 1H), 4.77 (s, 2H), 3.80-3.70 (m, 1H), 3.45-3.37 (m, 1H), 3.25-3.16 (m, 1H), 2.15-2.08 (m, 1H), 2.06-1.96 (m, 1H), 1.83-1.75 (m, 2H), 1.42-1.25 (m, 4H); Mass (m/z): 382.4 (M + H)$^+$. |
| 91 | N-(cis-1S,2S-2-Hydroxycyclohexyl)-4-{2-chloropyridin-5-ylmethyl}-4H-benzo[1,4]thiazine-2-carboxamide | $^1$H-NMR (400 MHz, CDCl$_3$): δ 8.42 (d, J = 1.4 Hz, 1H), 7.69 (dd, J = 1.4, 8.0 Hz, 1H), 7.39 (s, 1H), 7.33 (d, J = 8.3 Hz, 1H), 7.05-6.90 (m, 3H), 6.52 (d, J = 7.8 Hz, 1H), 6.02 (d, J = 6.6 Hz, 1H), 4.77 (s, 2H), 3.78-3.64 (m, 2H), 3.44-3.36 (m, 1H), 2.13-2.05 (m, 1H), 2.05-1.96 (m, 1H), 1.81-1.72 (m, 2H), 1.43-1.20 (m, 4H); Mass (m/z): 416.3, 418.2 (M + H)$^+$. |

| Example Number | Chemical name and Structure | Characterization data |
|---|---|---|
| 92 | N-(cis-1S,2S-2-Hydroxycyclohexyl)-4-{[pyridin-2-ylmethyl}-4H-benzo[1,4]thiazine-2-carboxamide 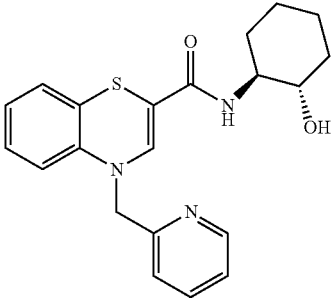 | $^1$H-NMR (400 MHz, CDCl$_3$): δ 8.60 (d, J = 4.3 Hz, 1H), 7.68 (t, J = 7.5 Hz, 1H), 7.46 (s, 1H), 7.41 (d, J = 7.7 Hz, 1H), 7.22 (t, J = 5.9 Hz, 1H), 6.98-6.88 (m, 3H), 6.57 (d, J = 7.7 Hz, 1H), 6.0 (d, J = 6.5 Hz, 1H), 4.87 (s, 2H), 3.84 (bs, 1H), 3.78-3.65 (m, 1H), 3.43-3.33 (m, 1H), 2.15-2.05 (m, 1H), 2.05-1.96 (m, 1H), 1.81-1.70 (m, 2H), 1.42-1.20 (m, 4H); Mass (m/z): 382.4 (M + H)$^+$. |

Example 93

N-(cis-1S,2S-2-Hydroxycyclohexyl)-4-(2,3-difluorobenzyl)-1-oxo-4H-benzo[1,4]thiazine-2-carboxamide

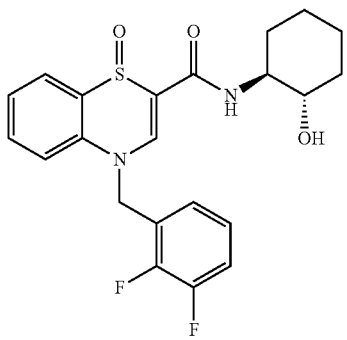 [SMILES: O=C(N[C@H]1CCCC[C@@H]1O)C1=CN(Cc2cccc(F)c2F)c2ccccc2S1=O]

To a stirred solution of compound of example 85 (136.0 mg, 0.33 mmol) in 1:1 mixture of methanol and THF (1.4 mL) at RT, solution of NaIO$_4$ (76.5 mg, 0.36 mmol) in water (1.6 mL) was added over a period of 15 minutes. The reaction mass was stirred for 16 hours at RT and filtered through a pad of celite. The filtrate was evaporated under reduced pressure. The crude mass was dissolved in dichloromethane and washed with water and brine solution. The organic layer was dried over anhydrous Na$_2$SO$_4$ and the solvent was removed under reduced pressure to obtain the title compound.

Yield: 115 mg; $^1$H-NMR (400 MHz, CDCl$_3$): δ 8.33 (s, 1H), 8.02 (d, J=7.7 Hz, 1H), 7.59 (t, J=7.7 Hz, 1H), 7.43 (d, J=7.4 Hz, 1H), 7.20-7.10 (m, 2H), 7.06-6.97 (m, 1H), 6.74 (t, J=6.9 Hz, 1H), 6.57 (d, J=6.4 Hz, 1H), 5.53 (d, J=17.2 Hz, 1H), 5.31 (d, J=17.2 Hz, 1H), 3.95-3.85 (m, 2H), 3.51-3.42 (m, 1H), 2.20-2.06 (m, 2H), 1.83-1.72 (m, 2H), 1.50-1.20 (m, 4H); Mass (m/z): 433.3 (M+H)$^+$.

Examples 94 to 97

The compounds of Examples 94 to 97 were prepared by following the experimental procedures as described in the Example 93 given above, with some noncritical variations.

| Example Number | Chemical name and Structure | Characterization data |
|---|---|---|
| 94 | N-(cis-1S,2S-2-Hydroxycyclohexyl)-4-benzyl-1-oxo-4H-benzo[1,4]thiazine-2-carboxamide 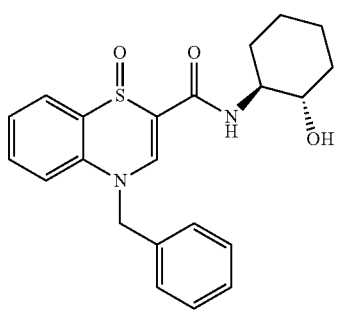 | $^1$H-NMR (400 MHz, CDCl$_3$): δ 8.28 (s, 1H), 8.01 (d, J = 7.2 Hz, 1H), 7.53 (t, J = 7.5 Hz, 1H), 7.42-7.22 (m, 5H), 7.21-7.17 (m, 2H), 6.61 (d, J = 7.0 Hz, 1H), 5.39 (d, J = 16.7 Hz, 1H), 5.31 (d, J = 16.7 Hz, 1H), 4.06 (bs, 1H), 3.90-3.80 (m, 1H), 3.60-3.48 (m, 1H), 2.20-2.0 (m, 2H), 1.85-1.73 (m, 2H), 1.49-1.20 (m, 4H); Mass (m/z): 397.3 (M + H)$^+$. |

-continued

| Example Number | Chemical name and Structure | Characterization data |
|---|---|---|
| 95 | N-(cis-1S,2S-2-Hydroxycyclohexyl)-4-{3-fluorobenzyl}-1-oxo-4H-benzo[1,4]thiazine-2-carboxamide | $^1$H-NMR (400 MHz, CDCl$_3$): δ 8.26 (s, 1H), 8.02 (d, J = 7.3 Hz, 1H), 7.55 (t, J = 7.4 Hz, 1H), 7.41 (t, J = 7.5 Hz, 1H), 7.38-7.25 (m, 1H), 7.25-7.20 (m, 1H), 7.00 (t, J = 8.2 Hz, 1H), 6.97 (d, J = 7.6 Hz, 1H), 6.90 (d, J = 9.1 Hz, 1H), 6.64 (d, J = 7.0 Hz, 1H), 5.38 (d, J = 17.0 Hz, 1H), 5.30 (d, J = 17.0 Hz, 1H), 4.10 (bs, 1H), 3.90-3.80 (m, 1H), 3.58-3.46 (m, 1H), 2.20-2.0 (m, 2H), 1.80-1.70 (m, 2H), 1.49-1.20 (m, 4H); Mass (m/z): 415.2 (M + H)$^+$. |
| 96 | N-(cis-1S,2S-2-Hydroxycyclohexyl)-4-{pyridin-2-ylmethyl}-1-oxo-4H-benzo[1,4]thiazine-2-carboxamide | $^1$H-NMR (400 MHz, CDCl$_3$): δ 8.60 (d, J = 4.0 Hz, 1H), 8.42 (s, 1H), 7.99 (d, J = 7.6 Hz, 1H), 7.64 (t, J = 7.3 Hz, 1H), 7.43-7.34 (m, 2H), 7.30-7.20 (m, 2H), 7.12 (d, J = 7.8 Hz, 1H), 6.61 (d, J = 6.6 Hz, 1H), 5.50 (d, J = 17.0 Hz, 1H), 5.34 (d, J = 17.0 Hz, 1H), 3.92-3.83 (m, 1H), 3.58-3.44 (m, 2H), 2.20-2.05 (m, 2H), 1.82-1.70 (m, 2H), 1.45-1.25 (m, 4H); Mass (m/z): 398.4 (M + H)$^+$. |
| 97 | N-(cis-1S,2S-2-Hydroxycyclohexyl)-4-{2-chloropyridin-5-ylmethyl}-1-oxo-4H-benzo[1,4]thiazine-2-carboxamide | $^1$H-NMR (400 MHz, CDCl$_3$): δ 8.39 (s, 1H), 8.38-8.28 (m, 1H), 8.02 (d, J = 7.4 Hz, 1H), 7.57 (t, J = 7.4 Hz, 1H), 7.50-7.38 (m, 2H), 7.30-7.20 (m, 2H), 6.60-6.50 (m, 1H), 5.44 (d, J = 16.9 Hz, 1H), 5.29 (d, J = 16.9 Hz, 1H), 3.96-3.82 (m, 1H), 3.60-3.42 (m, 1H), 3.23 (d, J = 4.4 Hz, 1H), 2.20-2.06 (m, 2H), 1.85-1.72 (m, 2H), 1.45-1.20 (m, 4H); Mass (m/z): 432.2, 434.3 (M + H)$^+$. |

Examples 98 to 101

The compounds of Example 98 to 101 can be prepared easily from the Examples 77 to 80 respectively by following the experimental procedures as described in Example 81, with some non-critical variations.

Example 98

N-(3-Hydroxypiperidin-4-yl)-4-(4-fluorobenzyl)-8-fluoro-4H-benzo[1,4]oxazine-2-carboxamide.

Example 99

N-(3-Hydroxypiperidin-4-yl)-4-(4-fluorobenzyl)-4H-benzo[1,4]oxazine-2-carboxamide

Example 100

N-(3-Hydroxypiperidin-4-yl)-4-(2,3-difluorobenzyl)-4H-benzo[1,4]oxazine-2-carboxamide

Example 101

N-(3-Hydroxypiperidin-4-yl)-4-(2-fluorobenzyl)-8-fluoro-4H-benzo[1,4]oxazine-2-carboxamide

Example 102

Determination of Allosteric Potency $EC_{50}$ Values for Muscarinic M1 Receptor:

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50% in presence of $EC_{20}$ of acetylcholine.

| Example | $EC_{50}$ (nM) |
| --- | --- |
| 1 | 422 |
| 2 | 134 |
| 3 | 1154 |
| 4 | 1431 |
| 5 | 135 |
| 6 | 1511 |
| 7 | 891 |
| 8 | 2894 |
| 9 | 699 |
| 10 | 1553 |
| 11 | 498 |
| 12 | 1510 |
| 13 | 907 |
| 14 | 1356 |
| 15 | 591 |
| 16 | 1347 |
| 17 | 149 |
| 18 | 331 |
| 19 | 120 |
| 20 | 1251 |
| 21 | 369 |
| 22 | 353 |
| 23 | 323 |
| 24 | 514 |
| 25 | 911 |
| 26 | 159 |
| 27 | 1374 |
| 28 | 250 |
| 29 | 140 |
| 30 | 955 |
| 31 | 1000 |
| 33 | 1183 |
| 34 | 1517 |
| 35 | 1576 |
| 36 | 1545 |
| 37 | 534 |
| 38 | 262 |
| 39 | 1553 |
| 40 | 1532 |
| 41 | 168 |
| 42 | 686 |
| 43 | 1625 |
| 44 | 1275 |
| 45 | 1578 |
| 46 | 1084 |
| 47 | 1316 |
| 48 | 143 |
| 51 | 420 |
| 52 | 1354 |
| 53 | 230 |
| 54 | 88 |
| 55 | 828 |
| 56 | 1485 |
| 57 | 179 |
| 58 | 1336 |
| 59 | 1009 |
| 61 | 219 |
| 73 | 2370 |
| 74 | 2100 |
| 75 | 160 |
| 76 | 412 |
| 85 | 117 |
| 86 | 936 |
| 87 | 131 |
| 88 | 145 |
| 89 | 460 |
| 90 | 599 |
| 91 | 141 |
| 92 | 1470 |
| 93 | 906 |
| 94 | 1395 |
| 95 | 1518 |
| 96 | 2162 |
| 97 | 1060 |

Example 103

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) for 1 hour in the absence of any objects on day 1.

One group of 12 rats received vehicle and another set of animals received test compounds or test compounds and Donepezil, before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 hours after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch. $T_1$ is the total time spent exploring the familiar objects (a1+a2).

$T_2$ is the total time spent exploring the familiar object and novel object (a3+b).

Discriminative index=Time spent with novel object/
(time spent with novel and familiar object).

The object recognition test was performed as described in *Behavioural Brain Research*, 1988, 31, 47-59.

| Example Number | Dose | Exploration time mean ± S.E.M (sec) | | Inference |
|---|---|---|---|---|
| | | Familiar object | Novel object | |
| 1 | 1 mg/kg, p.o. | 10.93 ± 1.98 | 19.27 ± 2.94 | Active |
| 4 | 10 mg/kg, p.o. | 7.43 ± 0.67 | 11.21 ± 1.26 | Active |
| 7 | 3 mg/kg, p.o. | 9.23 ± 1.53 | 13.92 ± 1.99 | Active |
| 9 | 1 mg/kg, p.o. | 8.64 ± 0.82 | 18.55 ± 1.70 | Active |
| 11 | 1 mg/kg, p.o. | 10.05 ± 1.66 | 16.92 ± 1.86 | Active |
| 18 | 1 mg/kg, p.o. | 8.74 ± 1.49 | 16.47 ± 1.82 | Active |
| 20 | 10 mg/kg, p.o. | 12.17 ± 1.84 | 19.94 ± 3.02 | Active |
| 21 | 1 mg/kg, p.o. | 9.18 ± 1.63 | 17.67 ± 2.89 | Active |
| 23 | 1 mg/kg, p.o. | 13.15 ± 1.55 | 17.99 ± 2.53 | Active |

Effect of Example 18 in Combination with Donepezil

Procognitive effects observed with combination of test compound, example 18 and donepezil is better than the either treatment. The results are shown in FIGS. 1 and 2.

Example 104

Object Recognition Task Model—Scopolamine Challenge

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) for 1 hour in the absence of any objects on day 1.

Rats received vehicle or vehicle and scopolamine or compound of the formula (I) and scopolamine, before the familiar ($T_1$). During the familiarization phase, ($T_1$), the rats were placed individually in the arena for 3 minutes, in which two identical objects ($a_1$ and $a_2$) were positioned 10 cm from the wall. 3 minutes after $T_1$, trial for memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch. $T_1$ is the total time spent exploring the familiar objects (a1+a2).

$T_2$ is the total time spent exploring the familiar object and novel object (a3+b).

Discriminative index=Time spent with novel object/
(time spent with novel and familiar object).

| Example Number | Dose | Exploration time mean ± S.E.M (sec) | | Inference |
|---|---|---|---|---|
| | | Familiar object | Novel object | |
| 1 | 0.3 mg/kg, p.o. | 11.57 ± 1.51 | 22.66 ± 2.90 | Active |

Example 105

Contextual Fear Conditioning Task

Experiment was carried out over a period of two days. On day 1, rats were placed in the operant behavior chamber and allowed to acclimatize for 2 minutes. Rats received an unavoidable foot shock (unconditioned stimulus (US): electric shock of 0.5-0.7 mA for 3 sec). Following a 1 minute interval, shocks were repeated to deliver a total of three US. Rats were administered with vehicle or test compound post training. Scopolamine (0.3 mg/kg, s.c.) was administered 120 minutes after training.

On day 2, rats were placed in the operant behavior chamber and total freezing time was scored for a period of 5 minutes. Test compound, example 18 reversed the scopolamine induced memory deficit and the result is shown in FIG. 3.

Example 106

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (1 mg/kg) dosing (n=3/group) and fasted overnight before oral dosing (p.o.). However, rats allocated to intravenous (i.v.) dosing food and water was provided ad libitum.

At pre-determined point, blood was collected through jugular vein and replenished with an equivalent volume of normal saline. Collected blood was transferred into a labeled eppendorf tube containing 10 μL of heparin as an anticoagulant. Typically blood samples were collected at following time points: 0.08, 0.25, 0.5, 1, 2, 4, 6, 8, and 24 hours post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$, clearance, Vz and bioavailability were calculated by non-compartmental model using standard non-compartmental model by using Phoenix WinNonlin 6.0.2 or 6.0.3 version Software package.

| Ex. No | Dose (mg/kg) | ROA | $C_{max}$ (ng/mL) | $T_{max}$ (hr) | $AUC_{0-t}$ (ng/hr/mL) | $T_{1/2}$ (hr) | Clearance (mL/min/kg) | Vz (L/kg) | Bioavailability (%) |
|---|---|---|---|---|---|---|---|---|---|
| 1 | 3 | oral (gavage) | 419 ± 162 | 0.5 ± 0 | 989 ± 386 | 2.3 ± 1.1 | — | — | 40 ± 15 |
|   | 1 | i.v. (bolus) | — | — | 834 ± 101 | 2.3 ± 0.7 | 19 ± 2 | 4.0 ± 1.4 |   |
| 4 | 3 | oral (gavage) | 245 ± 27 | 0.58 ± 0.38 | 607 ± 62 | 1.5 ± 0.3 | — | — | 49 ± 5 |
|   | 1 | i.v. (bolus) | — | — | 415 ± 17 | 1.4 ± 0.1 | 40 ± 2 | 4.7 ± 0.1 |   |
| 5 | 3 | oral (gavage) | 430 ± 35 | 2.83 ± 2.02 | 3982 ± 533 | 3.9 ± 0.1 | — | — | 115 ± 15 |
|   | 1 | i.v. (bolus) | — | — | 1150 ± 62 | 4.5 ± 0.2 | 14 ± 1 | 5.6 ± 0.5 |   |
| 7 | 3 | oral (gavage) | 313 ± 111 | 0.50 ± 0 | 652 ± 227 | 1.8 ± 0.3 | — | — | 39 ± 14 |
|   | 1 | i.v. (bolus) | — | — | 553 ± 42 | 1.7 ± 0.3 | 29 ± 2 | 4.3 ± 0.9 |   |
| 9 | 3 | oral (gavage) | 320 ± 68 | 1.33 ± 0.58 | 1183 ± 245 | 2.9 ± 1.3 | — | — | 55 ± 11 |
|   | 1 | i.v. (bolus) | — | — | 711 ± 137 | 4.2 ± 2.2 | 24 ± 4 | 8.3 ± 4.1 |   |
| 11 | 3 | oral (gavage) | 392 ± 43 | 1.0 ± 0 | 1498 ± 200 | 1.8 ± 0.1 | — | — | 60 ± 8 |
|   | 1 | i.v. (bolus) | — | — | 838 ± 163 | 1.9 ± 0.6 | 20 ± 4 | 3.1 ± 0.3 |   |
|   | 1 | i.v. (bolus) | — | — | 1920 ± 120 | 3.4 ± 0.1 | 8.7 ± 0.5 | 2.5 ± 0.2 |   |
| 17 | 3 | oral (gavage) | 91 ± 38 | 4 ± 0 | 467 ± 169 | 2.6 ± 0.2 | — | — | 26 ± 9 |
|   | 1 | i.v. (bolus) | — | — | 600 ± 74 | 9.2 ± 2.2 | 27 ± 3 | 22 ± 8 |   |
| 18 | 3 | oral (gavage) | 477 ± 96 | 0.42 ± 0.14 | 2069 ± 839 | 3.9 ± 0.8 | — | — | 74 ± 30 |
|   | 1 | i.v. (bolus) | — | — | 929 ± 27 | 2.1 ± 0.1 | 17 ± 1 | 3.2 ± 0.1 |   |
| 19 | 3 | oral (gavage) | 252 ± 17 | 1.67 ± 0.6 | 2488 ± 223 | 3.7 ± 0.1 | — | — | 67 ± 6 |
|   | 1 | i.v. (bolus) | — | — | 1245 ± 84 | 3.8 ± 0.5 | 13 ± 1.0 | 4.4 ± 0.2 |   |
| 21 | 3 | oral (gavage) | 992 ± 150 | 0.67 ± 0.29 | 4271 ± 800 | 2.7 ± 0.3 | — | — | 95 ± 18 |
|   | 1 | i.v. (bolus) | — | — | 1493 ± 149 | 1.7 ± 0.3 | 11 ± 1 | 1.5 ± 0.1 |   |
| 23 | 3 | oral (gavage) | 428 ± 78 | 0.42 ± 0.14 | 437 ± 138 | 1.2 ± 0.6 | — | — | 35 ± 11 |
|   | 1 | i.v. (bolus) | — | — | 419 ± 182 | 1.5 ± 0.9 | 44 ± 21 | 6.8 ± 7.1 |   |
| 33 | 3 | oral (gavage) | 159 ± 26 | 1.50 ± 0.9 | 719 ± 269 | 3.2 ± 2.0 | — | — | 53 ± 20 |
|   | 1 | i.v. (bolus) | — | — | 452 ± 135 | 1.2 ± 0.6 | 39 ± 10 | 3.5 ± 1.0 |   |
| 51 | 3 | oral (gavage) | 132 ± 32 | 1.0 ± 0 | 371 ± 149 | 2.3 ± 0.5 | — | — | 23 ± 9 |
|   | 1 | i.v. (bolus) | — | — | 533 ± 62 | 3.6 ± 3.0 | 31 ± 4 | 9.8 ± 8.0 |   |
| 92 | 3 | oral (gavage) | 195 ± 22 | 0.33 ± 0.14 | 255 ± 32 | 1.7 ± 1.0 | — | — | 32 ± 4 |
|   | 1 | i.v. (bolus) | — | — | 262 ± 50 | 0.8 ± 0.2 | 64 ± 11 | 4.2 ± 0.7 |   |

Example 107

Rodent Brain Penetration Study

Male Wistar rats (260±40 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male Wistar rats were acclimatized and randomly grouped according to their weight. At each time point (0.50, 1 and 2 hours) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$).

| Example | Single dose Rat Brain Penetration ($C_b/C_p$) at 3 mg/kg, p.o. |
|---|---|
| 1 | 1.18 ± 0.38 |
| 4 | 1.43 ± 0.01 |
| 5 | 0.90 ± 0.15 |
| 7 | 1.04 ± 0.16 |
| 9 | 0.65 ± 0.20 |
| 11 | 1.44 ± 0.16 |
| 17 | 1.92 ± 0.24 |
| 18 | 2.27 ± 0.64 |
| 20 | 0.82 ± 0.25 |
| 21 | 0.25 ± 0.08 |
| 23 | 0.32 ± 0.02 |
| 33 | 1.96 ± 0.91 |
| 51 | 1.93 ± 0.37 |

Example 108

Modulation of Soluble Amyloid Precursor Protein α (sAPPα) Levels in Cortex

In addition to providing symptomatic treatment for cognitive deficits in Alzheimer's disease, activation of the M1 receptor also has disease modifying effects in AD patients. Positive allosteric modulators at M1 receptor have demonstrated to increase the generation of sAPPα in-vitro indicating processing of amyloid precursor protein through the non-amyloidogenic pathway.

Experimental Procedure

Estimation of Cortical sAPPα Levels in Rat Brain

Male Wistar rats (250±40 grams) were randomly divided (n=8 group) into different treatment groups. Control group of rats were intraperitoneally (i.p.) administered with vehicle (99.75% of 0.25% HEC HHX+0.25% tween 80). Rats from treatment groups received a single intraperitoneal injection of test compound (dose volume of 2 mL/kg). Rats were sacrificed by cervical dislocation at 60 minutes after administration of test compound. Brains were quickly isolated and the cortex was dissected at −20° C. The cortex was immediately kept on a dry ice and weighed before being stored at −80° C. until quantification of sAPPα using Enzyme-linked immunosorbent assay (ELISA).

Estimation of Cortical sAPPα Levels in Mice Brain

Male C57BL/6J mice (250±40 grams) were randomly divided (n=8 group) into five groups. Control group of mice were intraperitoneally (i.p.) administered with vehicle (99.75% of 0.25% HEC HHX+0.25% tween 80) and the treatment group of mice received a single intraperitoneal injection of example 18 (dose volume of 10 mL/kg). Mice were sacrificed by cervical dislocation at 60 minutes after administration of test compound. Brains were quickly isolated and the cortex was dissected at −20° C. The cortex was immediately kept on a dry ice and weighed before being stored at −80° C. until quantification of sAPPα using Enzyme-linked immunosorbent assay (ELISA).

Sample Preparation:
1. Protease inhibitor cocktail tablets (complete mini, Make-Roche; 1 tablet for 8 mL) were added to the Tris Buffer Saline (TBS) prior to using the buffer for the tissue processing.
2. Cortical tissues were thawed and homogenized in five volumes of TBS and the solution was centrifuged at 15,000 rpm at 4° C. for 90 minutes.
3. The supernatant was discarded and homogenized in five volumes of TBS. Samples were centrifuged at 15,000 rpm at 4° C. for 30 minutes.
4. Supernatant was discarded and precipitated was sonicated in ten volumes of 6 M Guanidine-HCl (in 50 mM Tris buffer, pH: 7.6). Sonication was repeated four times with duration of five seconds every time.
5. Resulting mixture was incubated at the room temperature for 30 minutes and centrifuged at 15,000 rpm at 4° C. for 30 minutes. Supernatant was diluted 100 times with EIA buffer prior to addition in the pre-coated ELISA plates.

Measurement of sAPPα by ELISA Kit:

To investigate the role of an acute treatment of test compound on sAPPα levels, the expression of this protein was measured in homogenates obtained from the cortex of treated and untreated rats by employing ELISA assay. The entire procedure was followed as described in the ELISA kit manual (Mouse/Rat sAPPα ELISA, Catalog Number: JP27419, Immuno-Biological Laboratories, Hamburg, Germany).

Statistical Analysis:

Statistical analyses were performed using the Graph Pad Prism (Version 4). Results are expressed as Mean±SEM levels of sAPPα expressed as percentage of control values (rats treated with vehicle). Statistical significance after treatment was assessed using One-Way ANOVA followed by Dunnett's post test and the significance level was set below p value less than 0.05.

REFERENCES

*Neurotherapeutics*, 2008, 5, 433-442
*Current Alzheimer Research*, 2009, 6, 112-117
*The Journal of Neuroscience*, 2009, 29, 14271-14286
*Journal of Pharmacology and Experimental Therapeutics*, 2003, 305, 864-871

Result:

After sixty minutes post treatment, the test compound, example 18 produced significant increases in the cortical sAPPα levels in mice brain with mean increase of 38% observed at a dose 10 mg/kg, i.p. and the result are shown in FIG. 4. Similarly, Example 18 produced dose-dependent increase in the rat brain cortical sAPPα levels with mean maximum increase of 26% observed at a dose 10 mg/kg, i.p. and the result is shown in FIG. 5.

Example 109

Modulation of Cerebral Blood Flow in Frontal Cortex:

The effect of test compound on modulation of cerebral blood flow was evaluated using rats.

Rats were acclimatized to the laboratory environment for at least 7 days. Rats (300-350 grams) were housed in a group of four in a controlled environment (Temp=21±3° C.;

Humidity=30-70%) and maintained on a 12-hour light/dark cycle with lights on at 07:00 AM. Food and water was provided ad libitum.

Rats were anaesthetized with 12% urethane (i.p.). Animal's body core temperature was maintained at 37° C. via a heating pad and rectal temperature probe. A small incision was made at one of the ventral side of the hind limb and the femoral vein was cannulated with PE10 tubing for drug application. Then animal was placed into a stereotaxic frame and a midline incision was made to expose the skull. A burr hole was drilled over the frontal cortex (stereotaxic coordinates 1 mm anterior and 4 mm lateral to bregma). Oxygen was supplied through the nose cone of the seterotaxic apparatus which was connected to the controlled gaseous supplier with a flow of 200 mL/minute. Laser Doppler probe (AD Instruments Inc) was placed over the hole to monitor cerebral blood flow. The Laser Doppler probe was connected to a computerized data acquisition system (PowerLab 16/30, AD Instruments Inc). Vehicle or test compound were administered intravenously after cerebral blood flow was stable for 30 minutes. The cerebral blood flow was collected for further 90 minutes. Data obtained was calculated as percent increase relative to resting basal blood flow level. Test compound data was compared with the control group using one-way ANOVA followed by the Bonferroni post test.

REFERENCES

Psychopharmacology (Berl). 2013, 225, 21-30.

Result:

Example 18 significantly increased the cerebral blood flow as shown in FIG. 6.

We claim:

1. A compound of formula (I),

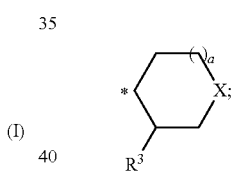

(I)

wherein:
$A^1$ and $A^2$ are each independently represents CH, CF or N;
W is O, S, S(O) or S(O)$_2$;
$R^1$ is

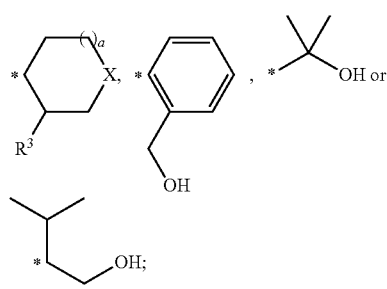

$R^2$ is

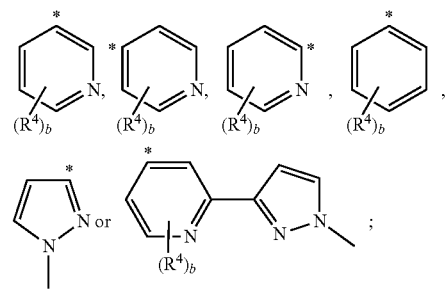

wherein * represents point of attachment;
$R^3$ is OH, F, NH$_2$ or H;
$R^4$ at each occurrence is independently selected from halogen, —O—CH$_3$; —S—CH$_3$, —N(CH$_3$)$_2$, —CH$_3$, —CF$_3$, —CHF$_2$, —CH$_2$F, —OH, —CN, phenyl, pyridyl and hydrogen; wherein phenyl and pyridyl are optionally substituted with one or more substituents selected from the group consisting of halogen or CH$_3$;
X is CH$_2$, O or NH; and
a is 0 or 1; and b is 1 or 2;
or an isotopic form, a stereoisomer, a tautomer or a pharmaceutically acceptable salt thereof.

2. The compound of formula (I) as claimed in claim 1, wherein:
W is O;
$A^1$ and $A^2$ are CH;
$R^1$ is

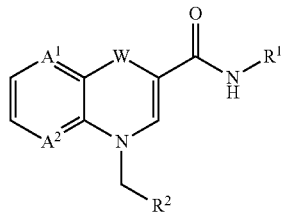

and
$R^2$ is

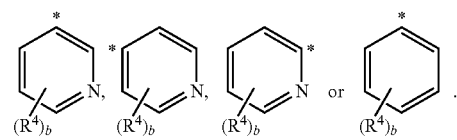

3. The compound of formula (I) as claimed in claim 1, wherein:
W is S;
$A^1$ and $A^2$ are CH;
$R^1$ is

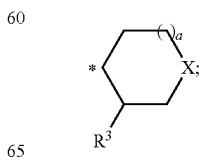

and

R² is

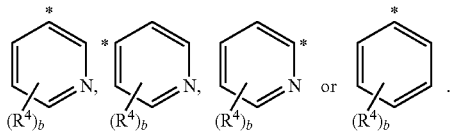

4. The compound of formula (I) as claimed in claim 1, wherein:
W is O;
A¹ and A² are CH;
R¹ is

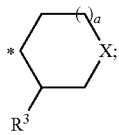

R² is

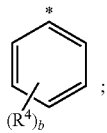

and
X is $CH_2$.

5. The compound of formula (I) as claimed in claim 1, wherein:
W is S;
A¹ and A² are CH;
R¹ is

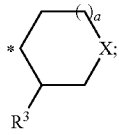

R² is

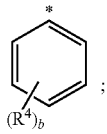

and
X is $CH_2$.

6. The compound according to claim 1, wherein the compound is selected from the group consisting of:
N-(cis-1S, 2S-2-Hydroxycyclohexyl)-4-(2-fluorobenzyl)-4H-benzo[1,4]oxazine-2-carboxamide;
N-(cis-1S, 2S-2-Hydroxycyclohexyl)-8-fluoro-4-(2-fluorobenzyl)-4H-benzo[1,4]oxazine-2-carboxamide;
N-(cis-1S, 2S-2-Hydroxycyclohexyl)-4-{2-fluorobenzyl}-4H-pyrido[3,2-b][1,4]oxazine-2-carboxamide;
N-(cis-1S, 2S-2-Hydroxycyclohexyl)-4-benzyl-4H-benzo[1,4]oxazine-2-carboxamide;
N-(cis-1S, 2S-2-Hydroxycyclohexyl)-4-(4-methoxybenzyl)-4H-benzo[1,4]oxazine-2-carboxamide;
N-(2-Hydroxy-2-methylpropyl)-4-(4-methoxybenzyl)-4H-benzo[1,4]oxazine-2-carboxamide;
N-(cis-1S, 2S-2-Hydroxycyclohexyl)-4-(3-fluorobenzyl)-4H-benzo[1,4]oxazine-2-carboxamide;
N-(2-Hydroxy-2-methylpropyl)-4-(3-fluorobenzyl)-4H-benzo[1,4]oxazine-2-carboxamide;
N-(cis-1S, 2S-2-Hydroxycyclohexyl)-4-(3-methoxybenzyl)-4H-benzo[1,4]oxazine-2-carboxamide;
N-(2-Hydroxy-2-methylpropyl)-4-(3-methoxybenzyl)-4H-benzo[1,4]oxazine-2-carboxamide;
N-(cis-1S, 2S-2-Hydroxycyclohexyl)-4-(2-methoxypyridin-4-ylmethyl)-4H-benzo[1,4]oxazine-2-carboxamide;
N-(2-Hydroxy-2-methylpropyl)-4-(2-methoxypyridin-4-yl methyl)-4H-benzo[1,4]oxazine-2-carboxamide;
N-(cis-1S, 2S-2-Hydroxycyclohexyl)-4-(4-fluorobenzyl)-4H-benzo[1,4]oxazine-2-carboxamide;
N-(2-Hydroxy-2-methylpropyl)-4-(4-fluorobenzyl)-4H-benzo[1,4]oxazine-2-carboxamide;
N-(cis-1S, 2S-2-Hydroxycyclohexyl)-4-(2-methoxy pyridin-5-ylmethyl)-4H-benzo[1,4]oxazine-2-carboxamide;
N-(2-Hydroxy-2-methylpropyl)-4-(2-methoxypyridin-5-ylmethyl)-4H-benzo[1,4]oxazine-2-carboxamide;
N-(cis-1S, 2S-2-Hydroxycyclohexyl)-4-(3-trifluoromethylbenzyl)-4H-benzo[1,4]oxazine-2-carboxamide;
N-(cis-1S, 2S-2-Hydroxycyclohexyl)-4-(2,3-difluoro benzyl)-4H-benzo[1,4]oxazine-2-carboxamide;
N-(cis-1S, 2S-2-Hydroxycyclohexyl)-4-(3,4-difluoro benzyl)-4H-benzo[1,4]oxazine-2-carboxamide;
N-(3-Hydroxytetrahydrpyran-4-yl)-4-(2,3-difluoro benzyl)-4H-benzo[1,4]oxazine-2-carboxamide;
N-(cis-1S, 2S-2-Hydroxycyclohexyl)-4-(2-chloropyridin-5-ylmethyl)-4H-benzo[1,4]oxazine-2-carboxamide;
N-(cis-1S, 2S-2-Hydroxycyclohexyl)-4-(pyridin-3-ylmethyl)-4H-benzo[1,4]oxazine-2-carboxamide;
N-(cis-1S, 2S-2-Hydroxycyclohexyl)-4-(pyridin-4-ylmethyl)-4H-benzo[1,4]oxazine-2-carboxamide;
N-(cis-1S, 2S-2-Hydroxycyclohexyl)-4-(2-chloropyridin-4-ylmethyl)-4H-benzo[1,4]oxazine-2-carboxamide;
N-(cis-1S, 2S-2-Hydroxycyclohexyl)-4-(pyridin-2-ylmethyl)-4H-benzo[1,4]oxazine-2-carboxamide;
N-(cis-1S, 2S-2-Hydroxycyclohexyl)-4-(3,4-dichloro benzyl)-4H-benzo[1,4]oxazine-2-carboxamide;
N-(cis-1S, 2S-2-Hydroxycyclohexyl)-4-(2-methylpyridin-3-ylmethyl)-4H-benzo[1,4]oxazine-2-carboxamide;
N-(cis-1S, 2S-2-Hydroxycyclohexyl)-4-(2,4-dichlorobenzyl)-4H-benzo[1,4]oxazine-2-carboxamide;
N-(cis-1S, 2S-2-Hydroxycyclohexyl)-8-fluoro-4-(2,3-difluorobenzyl)-4H-benzo[1,4]oxazine-2-carboxamide;
N-(cis-1S, 2S-2-Hydroxycyclohexyl)-4-benzyl-4H-pyrido[3,2-b][1,4]oxazine-2-carboxamide;
N-(cis-1S, 2S-2-Hydroxycyclohexyl)-1-Benzyl-1H-pyrido[2,3-b][1,4]oxazine-3-carboxamide;
N-(cis-1S, 2S-2-Hydroxycyclohexyl)-1-{2,3-difluorobenzyl}-1H-pyrido[2,3-b][1,4]oxazine-3-carboxamide;
N-(cis-1S, 2S-2-Hydroxycyclohexyl)-4-(2,3-difluorobenzyl)-4H-pyrido[3,2-b][1,4]oxazine-2-carboxamide;
N-(cis-1S, 2S-2-Hydroxycyclohexyl)-4-(3-fluoropyridin-4-ylmethyl)-4H-benzo[1,4]oxazine-2-carboxamide;

N-(cis-1S, 2S-2-Hydroxycyclohexyl)-4-(4-fluorobenzyl)-4H-pyrido[3,2-b][1,4]oxazine-2-carboxamide;
N-(cis-1S, 2S-2-Hydroxycyclohexyl)-1-(3-fluorobenzyl)-1H-pyrido[2,3-b][1,4]oxazine-3-carboxamide;
N-(cis-1S, 2S-2-Hydroxycyclohexyl)-4-(2-trifluoromethylbenzyl)-4H-benzo[1,4]oxazine-2-carboxamide;
N-(cis-1S, 2S-2-Hydroxycyclohexyl)-4-(2-chlorobenzyl)-8-fluoro-4H-benzo[1,4]oxazine-2-carboxamide;
N-(trans-1R,2R-2-Hydroxycyclopentyl)-4-(2,3-difluorobenzyl)-4H-benzo[1,4]oxazine-2-carboxamide;
N-(trans-1R,2R-2-Hydroxycyclopentyl)-4-(2-fluorobenzyl)-4H-benzo[1,4]oxazine-2-carboxamide;
N-(cis-1S, 2S-2-Hydroxycyclohexyl)-4-(2-chlorobenzyl)-4H-benzo[1,4]oxazine-2-carboxamide;
N-(trans-1R, 2R-2-Hydroxycyclopentyl)-4-(2,3-difluorobenzyl)-8-fluoro-4H-benzo[1,4]oxazine-2-carboxamide;
N-(2-Hydroxymethylphenyl)-4-(2-fluorobenzyl)-4H-benzo[1,4]oxazine-2-carboxamide;
N-(2-Hydroxymethylphenyl)-4-(2,3-difluorobenzyl)-8-fluoro-4H-benzo[1,4]oxazine-2-carboxamide;
N-(2-Hydroxymethylphenyl)-4-(2,3-difluorobenzyl)-4H-benzo[1,4]oxazine-2-carboxamide;
N-(2-Hydroxymethylphenyl)-4-(2-fluorobenzyl)-8-fluoro-4H-benzo[1,4]oxazine-2-carboxamide;
N-(1-Hydroxymethyl-2-methylpropyl)-8-fluoro-4-(2-fluorobenzyl)-4H-benzo[1,4]oxazine-2-carboxamide;
N-(cis-1S, 2S-2-Hydroxycyclohexyl)-4-benzyl-8-fluoro-4H-benzo[1,4]oxazine-2-carboxamide;
N-(cis-1R, 2R-2-Hydroxycyclohexyl)-4-{2-fluorobenzyl}-4H-benzo[1,4]oxazine-2-carboxamide;
N-(cis-1R, 2R-2-Hydroxycyclohexyl)-4-{2-fluorobenzyl}-8-fluoro-4H-benzo[1,4]oxazine-2-carboxamide;
N-(cis-1S, 2S-2-Hydroxycyclohexyl)-4-{3-fluorobenzyl}-8-fluoro-4H-benzo[1,4]oxazine-2-carboxamide;
N-(cis-1S, 2S-2-Hydroxycyclohexyl)-4-(2-phenylpyridin-4-ylmethyl)-4H-benzo[1,4]oxazine-2-carboxamide;
N-(cis-1S, 2S-2-Hydroxycyclohexyl)-8-fluoro-4-(2-phenylpyridin-4-ylmethyl)-4H-benzo[1,4]oxazine-2-carboxamide;
N-(cis-1S, 2S-2-Hydroxycyclohexyl)-4-(2-chloropyridin-4-ylmethyl)-8-fluoro-4H-benzo[1,4]oxazine-2-carboxamide;
N-(cis-1S, 2S-2-Hydroxycyclohexyl)-4-(2-fluorobenzyl)-5-fluoro-4H-benzo[1,4]oxazine-2-carboxamide;
N-(cis-1S, 2S-2-Hydroxycyclohexyl)-4-(pyridine-2-ylmethyl)-5-fluoro-4H-benzo[1,4]oxazine-2-carboxamide;
N-(cis-1S, 2S-2-Hydroxycyclohexyl)-4-(pyridine-4-ylmethyl)-8-fluoro-4H-benzo[1,4]oxazine-2-carboxamide;
N-(cis-1S, 2S-2-Hydroxycyclohexyl)-4-(6'-Fluoro-5'-methyl-[2,3']bipyridinyl-4-ylmethyl)-4H-benzo[1,4]oxazine-2-carboxamide;
N-(cis-1S, 2S-2-Hydroxycyclohexyl)-4-[2-(1-methyl-1H-pyrazol-3-yl)-pyridin-4-ylmethyl]-4H-benzo[1,4]oxazine-2-carboxamide;
N-(cis-1S, 2S-2-Hydroxycyclohexyl)-4-(1-methyl-1H-pyrazol-3-ylmethyl)-4H-benzo[1,4]oxazine-2-carboxamide;
N-(cis-1S, 2S-2-Hydroxycyclohexyl)-4-(2-fluorobenzyl)-5,8-difluoro-4H-benzo[1,4]oxazine-2-carboxamide;
N-(cis-1S, 2S-2-Hydroxycyclohexyl)-8-fluoro-4-(3-fluoropyridin-4-ylmethyl)-4H-benzo[1,4]oxazine-2-carboxamide;
N-(cis-1S, 2S-2-Hydroxycyclohexyl)-8-fluoro-4-(2-methylpyridin-4-ylmethyl)-4H-benzo[1,4]oxazine-2-carboxamide;
N-(cis-1S, 2S-2-Hydroxycyclohexyl)-8-fluoro-4-(2-methylpyridin-5-ylmethyl)-4H-benzo[1,4]oxazine-2-carboxamide;
N-(cis-1S, 2S-2-Hydroxycyclohexyl)-4-(2-methylpyridin-4-ylmethyl)-4H-benzo[1,4]oxazine-2-carboxamide;
N-(cis-1S, 2S-2-Hydroxycyclohexyl)-4-(2-methylpyridin-5-ylmethyl)-4H-benzo[1,4]oxazine-2-carboxamide;
N-(cis-1S, 2S-2-Hydroxycyclohexyl)-5,8-difluoro-4-(pyridin-4-ylmethyl)-4H-benzo[1,4]oxazine-2-carboxamide;
N-(3-Hydroxytetrahydropyran-4-yl)-4-(3-fluorobenzyl)-4H-benzo[1,4]oxazine-2-carboxamide;
N-(3-Hydroxytetrahydropyran-4-yl)-4-(4-fluorobenzyl)-8-fluoro-4H-benzo[1,4]oxazine-2-carboxamide;
N-(3-Hydroxytetrahydropyran-4-yl)-4-(3-trifluoromethylbenzyl)-4H-benzo[1,4]oxazine-2-carboxamide;
N-(3-Hydroxytetrahydropyran-4-yl)-4-(2-methoxypyridin-5-ylmethyl)-4H-benzo[1,4]oxazine-2-carboxamide;
N-(3-Hydroxytetrahydropyran-4-yl)-4-(pyridin-4-ylmethyl)-8-fluoro-4H-benzo[1,4]oxazine-2-carboxamide;
N-(3-Fluoropiperidin-4-yl)-4-(2-fluorobenzyl)-8-fluoro-4H-benzo[1,4]oxazine-2-carboxamide;
N-(3-Fluoropiperidin-4-yl)-4-(2,3-difluorobenzyl)-8-fluoro-4H-benzo[1,4]oxazine-2-carboxamide;
N-(3-Hydroxypiperidin-4-yl)-4-(2,3-difluorobenzyl)-8-fluoro-4H-benzo[1,4]oxazine-2-carboxamide;
N-(3-Hydroxypiperidin-4-yl)-4-(2-fluorobenzyl)-4H-benzo[1,4]oxazine-2-carboxamide;
N-(cis-1S, 2S-2-hydroxy cyclohexyl)-4-(2,3-difluorobenzyl)-4H-benzo[1,4]thiazine-2-carboxamide;
N-(cis-1S, 2S-2-Hydroxycyclohexyl)-4-(3-fluorobenzyl)-4H-benzo[1,4]thiazine-2-carboxamide;
N-(cis-1S, 2S-2-Hydroxycyclohexyl)-4-benzyl-4H-benzo[1,4]thiazine-2-carboxamide;
N-(cis-1S, 2S-2-Hydroxycyclohexyl)-4-{4-methoxybenzyl}-4H-benzo[1,4]thiazine-2-carboxamide;
N-(cis-1S, 2S-2-Hydroxycyclohexyl)-4-{4-fluorobenzyl}-4H-benzo[1,4]thiazine-2-carboxamide;
N-(cis-1S, 2S-2-Hydroxycyclohexyl)-4-{pyridin-4-ylmethyl}-4H-benzo[1,4]thiazine-2-carboxamide;
N-(cis-1S, 2S-2-Hydroxycyclohexyl)-4-{2-chloropyridin-5-yl-methyl}-4H-benzo[1,4]thiazine-2-carboxamide;
N-(cis-1S, 2S-2-Hydroxycyclohexyl)-4-{pyridin-2-ylmethyl}-4H-benzo[1,4]thiazine-2-carboxamide;
N-(cis-1S, 2S-2-Hydroxycyclohexyl)-4-(2,3-difluorobenzyl)-1-oxo-4H-benzo[1,4]thiazine-2-carboxamide;
N-(cis-1S, 2S-2-Hydroxycyclohexyl)-4-benzyl-1-oxo-4H-benzo[1,4]thiazine-2-carboxamide;
N-(cis-1S, 2S-2-Hydroxycyclohexyl)-4-{3-fluorobenzyl}-1-oxo-4H-benzo[1,4]thiazine-2-carboxamide;
N-(cis-1S, 2S-2-Hydroxycyclohexyl)-4-{pyridin-2-ylmethyl}-1-oxo-4H-benzo[1,4]thiazine-2-carboxamide;
N-(cis-1S, 2S-2-Hydroxycyclohexyl)-4-{2-chloropyridin-5-yl-methyl}-1-oxo-4H-benzo[1,4]thiazine-2-carboxamide;
N-(3-Hydroxypiperidin-4-yl)-4-(4-fluorobenzyl)-8-fluoro-4H-benzo[1,4]oxazine-2-carboxamide;
N-(3-Hydroxypiperidin-4-yl)-4-(4-fluorobenzyl)-4H-benzo[1,4]oxazine-2-carboxamide;
N-(3-Hydroxypiperidin-4-yl)-4-(2,3-difluorobenzyl)-4H-benzo[1,4]oxazine-2-carboxamide; and
N-(3-Hydroxypiperidin-4-yl)-4-(2-fluorobenzyl)-8-fluoro-4H-benzo[1,4]oxazine-2-carboxamide;

or a pharmaceutically acceptable salt thereof.

7. The compound according to claim 6, wherein the pharmaceutically acceptable salt is selected from the group consisting of:
- N-(3-Fluoropiperidin-4-yl)-4-(2-fluorobenzyl)-8-fluoro-4H-benzo[1,4]oxazine-2-carboxamide hydrochloride;
- N-(3-Fluoropiperidin-4-yl)-4-(2,3-difluorobenzyl)-8-fluoro-4H-benzo[1,4]oxazine-2-carboxamide hydrochloride;
- N-(3-Hydroxypiperidin-4-yl)-4-(2,3-difluorobenzyl)-8-fluoro-4H-benzo[1,4]oxazine-2-carboxamide trifluoroacetate;
- N-(3-Hydroxypiperidin-4-yl)-4-(2-fluorobenzyl)-4H-benzo[1,4]oxazine-2-carboxamide trifluoroacetate;
- N-(3-Hydroxypiperidin-4-yl)-4-(4-fluorobenzyl)-8-fluoro-4H-benzo[1,4]oxazine-2-carboxamide trifluoroacetate;
- N-(3-Hydroxypiperidin-4-yl)-4-(4-fluorobenzyl)-4H-benzo[1,4]oxazine-2-carboxamide trifluoroacetate;
- N-(3-Hydroxypiperidin-4-yl)-4-(2,3-difluorobenzy)-4H-benzo[1,4]oxazine-2-carboxamide trifluoroacetate; and
- N-(3-Hydroxypiperidin-4-yl)-4-(2-fluorobenzy)-8-fluoro-4H-benzo[1,4]oxazine-2-carboxamide trifluoroacetate.

8. A pharmaceutical composition comprising a compound according to claim 1, and pharmaceutically acceptable excipients or carriers.

9. A method for treating a disorder related to muscarinic M1 receptor selected from the group consisting of Alzheimer's disease, schizophrenia, cognitive disorders, pain, and sleep disorders, comprising administering to a patient in need thereof a therapeutically effective amount of a compound, or a pharmaceutically acceptable salt thereof, according to claim 1.

10. The method according to claim 9, wherein the compound is selected from the group consisting of:
- N-(cis-1S, 2S-2-Hydroxycyclohexyl)-4-(2-fluorobenzyl)-4H-benzo[1,4]oxazine-2-carboxamide;
- N-(cis-1S, 2S-2-Hydroxycyclohexyl)-8-fluoro-4-(2-fluorobenzyl)-4H-benzo[1,4]oxazine-2-carboxamide;
- N-(cis-1S, 2S-2-Hydroxycyclohexyl)-4-{2-fluorobenzyl}-4H-pyrido[3,2-b][1,4]oxazine-2-carboxamide;
- N-(cis-1S, 2S-2-Hydroxycyclohexyl)-4-benzyl-4H-benzo[1,4]oxazine-2-carboxamide;
- N-(cis-1S, 2S-2-Hydroxycyclohexyl)-4-(4-methoxybenzyl)-4H-benzo[1,4]oxazine-2-carboxamide;
- N-(2-Hydroxy-2-methylpropyl)-4-(4-methoxybenzyl)-4H-benzo[1,4]oxazine-2-carboxamide;
- N-(cis-1S, 2S-2-Hydroxycyclohexyl)-4-(3-fluorobenzyl)-4H-benzo[1,4]oxazine-2-carboxamide;
- N-(2-Hydroxy-2-methylpropyl)-4-(3-fluorobenzyl)-4H-benzo[1,4]oxazine-2-carboxamide;
- N-(cis-1S, 2S-2-Hydroxycyclohexyl)-4-(3-methoxybenzyl)-4H-benzo[1,4]oxazine-2-carboxamide;
- N-(2-Hydroxy-2-methylpropyl)-4-(3-methoxybenzyl)-4H-benzo[1,4]oxazine-2-carboxamide;
- N-(cis-1S, 2S-2-Hydroxycyclohexyl)-4-(2-methoxypyridin-4-ylmethyl)-4H-benzo[1,4]oxazine-2-carboxamide;
- N-(2-Hydroxy-2-methylpropyl)-4-(2-methoxypyridin-4-yl methyl)-4H-benzo[1,4]oxazine-2-carboxamide;
- N-(cis-1S, 2S-2-Hydroxycyclohexyl)-4-(4-fluorobenzyl)-4H-benzo[1,4]oxazine-2-carboxamide;
- N-(2-Hydroxy-2-methylpropyl)-4-(4-fluorobenzyl)-4H-benzo[1,4]oxazine-2-carboxamide;
- N-(cis-1S, 2S-2-Hydroxycyclohexyl)-4-(2-methoxy pyridin-5-ylmethyl)-4H-benzo[1,4]oxazine-2-carboxamide;
- N-(2-Hydroxy-2-methylpropyl)-4-(2-methoxypyridin-5-ylmethyl)-4H-benzo[1,4]oxazine-2-carboxamide;
- N-(cis-1S, 2S-2-Hydroxycyclohexyl)-4-(3-trifluoromethylbenzyl)-4H-benzo[1,4]oxazine-2-carboxamide;
- N-(cis-1S, 2S-2-Hydroxycyclohexyl)-4-(2,3-difluoro benzyl)-4H-benzo[1,4]oxazine-2-carboxamide;
- N-(cis-1S, 2S-2-Hydroxycyclohexyl)-4-(3,4-difluoro benzyl)-4H-benzo[1,4]oxazine-2-carboxamide;
- N-(3-Hydroxytetrahydrpyran-4-yl)-4-(2,3-difluoro benzyl)-4H-benzo[1,4]oxazine-2-carboxamide;
- N-(cis-1S, 2S-2-Hydroxycyclohexyl)-4-(2-chloropyridin-5-ylmethyl)-4H-benzo[1,4]oxazine-2-carboxamide;
- N-(cis-1S, 2S-2-Hydroxycyclohexyl)-4-(pyridin-3-ylmethyl)-4H-benzo[1,4]oxazine-2-carboxamide;
- N-(cis-1S, 2S-2-Hydroxycyclohexyl)-4-(pyridin-4-ylmethyl)-4H-benzo[1,4]oxazine-2-carboxamide;
- N-(cis-1S, 2S-2-Hydroxycyclohexyl)-4-(2-chloropyridin-4-ylmethyl)-4H-benzo[1,4]oxazine-2-carboxamide;
- N-(cis-1S, 2S-2-Hydroxycyclohexyl)-4-(pyridin-2-ylmethyl)-4H-benzo[1,4]oxazine-2-carboxamide;
- N-(cis-1S, 2S-2-Hydroxycyclohexyl)-4-(3,4-dichloro benzyl)-4H-benzo[1,4]oxazine-2-carboxamide;
- N-(cis-1S, 2S-2-Hydroxycyclohexyl)-4-(2-methylpyridin-3-ylmethyl)-4H-benzo[1,4]oxazine-2-carboxamide;
- N-(cis-1S, 2S-2-Hydroxycyclohexyl)-4-(2,4-dichlorobenzyl)-4H-benzo[1,4]oxazine-2-carboxamide;
- N-(cis-1S, 2S-2-Hydroxycyclohexyl)-8-fluoro-4-(2,3-difluorobenzyl)-4H-benzo[1,4]oxazine-2-carboxamide;
- N-(cis-1S, 2S-2-Hydroxycyclohexyl)-4-benzyl-4H-pyrido[3,2-b][1,4]oxazine-2-carboxamide;
- N-(cis-1S, 2S-2-Hydroxycyclohexyl)-1-Benzyl-1H-pyrido[2,3-b][1,4]oxazine-3-carboxamide;
- N-(cis-1S, 2S-2-Hydroxycyclohexyl)-1-{2,3-difluorobenzyl}-1H-pyrido[2,3-b][1,4]oxazine-3-carboxamide;
- N-(cis-1S, 2S-2-Hydroxycyclohexyl)-4-(2,3-difluorobenzyl)-4H-pyrido[3,2-b][1,4]oxazine-2-carboxamide;
- N-(cis-1S, 2S-2-Hydroxycyclohexyl)-4-(3-fluoropyridin-4-ylmethyl)-4H-benzo[1,4]oxazine-2-carboxamide;
- N-(cis-1S, 2S-2-Hydroxycyclohexyl)-4-(4-fluorobenzyl)-4H-pyrido[3,2-b][1,4]oxazine-2-carboxamide;
- N-(cis-1S, 2S-2-Hydroxycyclohexyl)-1-(3-fluorobenzyl)-1H-pyrido[2,3-b][1,4]oxazine-3-carboxamide;
- N-(cis-1S, 2S-2-Hydroxycyclohexyl)-4-(2-trifluoromethylbenzyl)-4H-benzo[1,4]oxazine-2-carboxamide;
- N-(cis-1S, 2S-2-Hydroxycyclohexyl)-4-(2-chlorobenzyl)-8-fluoro-4H-benzo[1,4]oxazine-2-carboxamide;
- N-(trans-1R,2R-2-Hydroxycyclopentyl)-4-(2,3-difluorobenzyl)-4H-benzo[1,4]oxazine-2-carboxamide;
- N-(trans-1R,2R-2-Hydroxycyclopentyl)-4-(2-fluorobenzyl)-4H-benzo[1,4]oxazine-2-carboxamide;
- N-(cis-1S, 2S-2-Hydroxycyclohexyl)-4-(2-chlorobenzyl)-4H-benzo[1,4]oxazine-2-carboxamide;
- N-(trans-1R, 2R-2-Hydroxycyclopentyl)-4-(2,3-difluorobenzyl)-8-fluoro-4H-benzo[1,4]oxazine-2-carboxamide;
- N-(2-Hydroxymethylphenyl)-4-(2-fluorobenzyl)-4H-benzo[1,4]oxazine-2-carboxamide;
- N-(2-Hydroxymethylphenyl)-4-(2,3-difluorobenzyl)-8-fluoro-4H-benzo[1,4]oxazine-2-carboxamide;
- N-(2-Hydroxymethylphenyl)-4-(2,3-difluorobenzyl)-4H-benzo[1,4]oxazine-2-carboxamide;

N-(2-Hydroxymethylphenyl)-4-(2-fluorobenzyl)-8-fluoro-4H-benzo[1,4]oxazine-2-carboxamide;
N-(1-Hydroxymethyl-2-methylpropyl)-8-fluoro-4-(2-fluorobenzyl)-4H-benzo[1,4]oxazine-2-carboxamide;
N-(cis-1S, 2S-2-Hydroxycyclohexyl)-4-benzyl-8-fluoro-4H-benzo[1,4]oxazine-2-carboxamide;
N-(cis-1R, 2R-2-Hydroxycyclohexyl)-4-{2-fluorobenzyl}-4H-benzo[1,4]oxazine-2-carboxamide;
N-(cis-1R, 2R-2-Hydroxycyclohexyl)-4-{2-fluorobenzyl}-8-fluoro-4H-benzo[1,4]oxazine-2-carboxamide;
N-(cis-1S, 2S-2-Hydroxycyclohexyl)-4-{3-fluorobenzyl}-8-fluoro-4H-benzo[1,4]oxazine-2-carboxamide;
N-(cis-1S, 2S-2-Hydroxycyclohexyl)-4-(2-phenylpyridin-4-ylmethyl)-4H-benzo[1,4]oxazine-2-carboxamide;
N-(cis-1S, 2S-2-Hydroxycyclohexyl)-8-fluoro-4-(2-phenylpyridin-4-ylmethyl)-4H-benzo[1,4]oxazine-2-carboxamide;
N-(cis-1S, 2S-2-Hydroxycyclohexyl)-4-(2-chloropyridin-4-ylmethyl)-8-fluoro-4H-benzo[1,4]oxazine-2-carboxamide;
N-(cis-1S, 2S-2-Hydroxycyclohexyl)-4-(2-fluorobenzyl)-5-fluoro-4H-benzo[1,4]oxazine-2-carboxamide;
N-(cis-1S, 2S-2-Hydroxycyclohexyl)-4-(pyridine-2-ylmethyl)-5-fluoro-4H-benzo[1,4]oxazine-2-carboxamide;
N-(cis-1S, 2S-2-Hydroxycyclohexyl)-4-(pyridine-4-ylmethyl)-8-fluoro-4H-benzo[1,4]oxazine-2-carboxamide;
N-(cis-1S, 2S-2-Hydroxycyclohexyl)-4-(6'-Fluoro-5'-methyl-2,3'bipyridinyl-4-ylmethyl)-4H-benzo[1,4]oxazine-2-carboxamide;
N-(cis-1S, 2S-2-Hydroxycyclohexyl)-4-[2-(1-methyl-1H-pyrazol-3-yl)-pyridin-4-ylmethyl]-4H-benzo[1,4]oxazine-2-carboxamide;
N-(cis-1S, 2S-2-Hydroxycyclohexyl)-4-(1-methyl-1H-pyrazol-3-ylmethyl)-4H-benzo[1,4]oxazine-2-carboxamide;
N-(cis-1S, 2S-2-Hydroxycyclohexyl)-4-(2-fluorobenzyl)-5,8-difluoro-4H-benzo[1,4]oxazine-2-carboxamide;
N-(cis-1S, 2S-2-Hydroxycyclohexyl)-8-fluoro-4-(3-fluoropyridin-4-ylmethyl)-4H-benzo[1,4]oxazine-2-carboxamide;
N-(cis-1S, 2S-2-Hydroxycyclohexyl)-8-fluoro-4-(2-methylpyridin-4-ylmethyl)-4H-benzo[1,4]oxazine-2-carboxamide;
N-(cis-1S, 2S-2-Hydroxycyclohexyl)-8-fluoro-4-(2-methylpyridin-5-ylmethyl)-4H-benzo[1,4]oxazine-2-carboxamide;
N-(cis-1S, 2S-2-Hydroxycyclohexyl)-4-(2-methylpyridin-4-ylmethyl)-4H-benzo[1,4]oxazine-2-carboxamide;
N-(cis-1S, 2S-2-Hydroxycyclohexyl)-4-(2-methylpyridin-5-ylmethyl)-4H-benzo[1,4]oxazine-2-carboxamide;
N-(cis-1S, 2S-2-Hydroxycyclohexyl)-5,8-difluoro-4-(pyridin-4-ylmethyl)-4H-benzo[1,4]oxazine-2-carboxamide;
N-(3-Hydroxytetrahydropyran-4-yl)-4-(3-fluorobenzyl)-4H-benzo[1,4]oxazine-2-carboxamide;
N-(3-Hydroxytetrahydropyran-4-yl)-4-(4-fluorobenzyl)-8-fluoro-4H-benzo[1,4]oxazine-2-carboxamide;
N-(3-Hydroxytetrahydropyran-4-yl)-4-(3-trifluoromethylbenzyl)-4H-benzo[1,4]oxazine-2-carboxamide;
N-(3-Hydroxytetrahydropyran-4-yl)-4-(2-methoxypyridin-5-ylmethyl)-4H-benzo[1,4]oxazine-2-carboxamide;
N-(3-Hydroxytetrahydropyran-4-yl)-4-(pyridin-4-ylmethyl)-8-fluoro-4H-benzo[1,4]oxazine-2-carboxamide;
N-(3-Fluoropiperidin-4-yl)-4-(2-fluorobenzyl)-8-fluoro-4H-benzo[1,4]oxazine-2-carboxamide;
N-(3-Fluoropiperidin-4-yl)-4-(2,3-difluorobenzyl)-8-fluoro-4H-benzo[1,4]oxazine-2-carboxamide;
N-(3-Hydroxypiperidin-4-yl)-4-(2,3-difluorobenzyl)-8-fluoro-4H-benzo[1,4]oxazine-2-carboxamide;
N-(3-Hydroxypiperidin-4-yl)-4-(2-fluorobenzyl)-4H-benzo[1,4]oxazine-2-carboxamide;
N-(cis-1S, 2S-2-hydroxy cyclohexyl)-4-(2,3-difluorobenzyl)-4H-benzo[1,4]thiazine-2-carboxamide;
N-(cis-1S, 2S-2-Hydroxycyclohexyl)-4-(3-fluorobenzyl)-4H-benzo[1,4]thiazine-2-carboxamide;
N-(cis-1S, 2S-2-Hydroxycyclohexyl)-4-benzyl-4H-benzo[1,4]thiazine-2-carboxamide;
N-(cis-1S, 2S-2-Hydroxycyclohexyl)-4-{4-methoxybenzyl}-4H-benzo[1,4]thiazine-2-carboxamide;
N-(cis-1S, 2S-2-Hydroxycyclohexyl)-4-{4-fluorobenzyl}-4H-benzo[1,4]thiazine-2-carboxamide;
N-(cis-1S, 2S-2-Hydroxycyclohexyl)-4-{pyridin-4-ylmethyl}-4H-benzo[1,4]thiazine-2-carboxamide;
N-(cis-1S, 2S-2-Hydroxycyclohexyl)-4-{2-chloropyridin-5-yl-methyl}-4H-benzo[1,4]thiazine-2-carboxamide;
N-(cis-1S, 2S-2-Hydroxycyclohexyl)-4-{pyridin-2-ylmethyl}-4H-benzo[1,4]thiazine-2-carboxamide;
N-(cis-1S, 2S-2-Hydroxycyclohexyl)-4-(2,3-difluorobenzyl)-1-oxo-4H-benzo[1,4]thiazine-2-carboxamide;
N-(cis-1S, 2S-2-Hydroxycyclohexyl)-4-benzyl-1-oxo-4H-benzo[1,4]thiazine-2-carboxamide;
N-(cis-1S, 2S-2-Hydroxycyclohexyl)-4-{3-fluorobenzyl}-1-oxo-4H-benzo[1,4]thiazine-2-carboxamide;
N-(cis-1S, 2S-2-Hydroxycyclohexyl)-4-{pyridin-2-ylmethyl}-1-oxo-4H-benzo[1,4]thiazine-2-carboxamide;
N-(cis-1S, 2S-2-Hydroxycyclohexyl)-4-{2-chloropyridin-5-yl-methyl}-1-oxo-4H-benzo[1,4]thiazine-2-carboxamide;
N-(3-Hydroxypiperidin-4-yl)-4-(4-fluorobenzyl)-8-fluoro-4H-benzo[1,4]oxazine-2-carboxamide;
N-(3-Hydroxypiperidin-4-yl)-4-(4-fluorobenzyl)-4H-benzo[1,4]oxazine-2-carboxamide;
N-(3-Hydroxypiperidin-4-yl)-4-(2,3-difluorobenzyl)-4H-benzo[1,4]oxazine-2-carboxamide; and
N-(3-Hydroxypiperidin-4-yl)-4-(2-fluorobenzyl)-8-fluoro-4H-benzo[1,4]oxazine-2-carboxamide;
or a pharmaceutically acceptable salt thereof.

11. The method according to claim 10, wherein the pharmaceutically acceptable salt is selected from the group consisting of:
N-(3-Fluoropiperidin-4-yl)-4-(2-fluorobenzyl)-8-fluoro-4H-benzo[1,4]oxazine-2-carboxamide hydrochloride;
N-(3-Fluoropiperidin-4-yl)-4-(2,3-difluorobenzyl)-8-fluoro-4H-benzo[1,4]oxazine-2-carboxamide hydrochloride;
N-(3-Hydroxypiperidin-4-yl)-4-(2,3-difluorobenzyl)-8-fluoro-4H-benzo[1,4]oxazine-2-carboxamide trifluoroacetate;
N-(3-Hydroxypiperidin-4-yl)-4-(2-fluorobenzyl)-4H-benzo[1,4]oxazine-2-carboxamide trifluoroacetate;
N-(3-Hydroxypiperidin-4-yl)-4-(4-fluorobenzyl)-8-fluoro-4H-benzo[1,4]oxazine-2-carboxamide trifluoroacetate;
N-(3-Hydroxypiperidin-4-yl)-4-(4-fluorobenzyl)-4H-benzo[1,4]oxazine-2-carboxamide trifluoroacetate;
N-(3-Hydroxypiperidin-4-yl)-4-(2,3-difluorobenzyl)-4H-benzo[1,4]oxazine-2-carboxamide trifluoroacetate; and N-(3-Hydroxypiperidin-4-yl)-4-(2-fluorobenzyl)-8-fluoro-4H-benzo[1,4]oxazine-2-carboxamide trifluoroacetate.

12. The method according to claim 9, wherein the disorder related to muscarinic M1 receptor is Alzheimer's disease.

13. The method according to claim 9, wherein the disorder related to muscarinic M1 receptor is schizophrenia.

14. The method according to claim 9, wherein the disorder related to muscarinic M1 receptor is a cognitive disorder.

15. The method according to claim 9, wherein the disorder related to muscarinic M1 receptor is pain.

16. The method according to claim 9, wherein the disorder related to muscarinic M1 receptor is a sleep disorder.

* * * * *